United States Patent
Bakthavatchalam et al.

(10) Patent No.: US 7,329,664 B2
(45) Date of Patent: Feb. 12, 2008

(54) SUBSTITUTED (7-PYRIDYL-4-PHENYL-AMINO-QUINAZOLIN-2-YL)-METHANOL ANALOGUES

(75) Inventors: Rajagopal Bakthavatchalam, Madison, CT (US); Charles A. Blum, Westbrook, CT (US); Harry Brielmann, Guilford, CT (US); Stéphane De Lombaert, Madison, CT (US); Xiaozhang Zheng, Branford, CT (US)

(73) Assignee: Neurogen Corporation, Branford, CT (US)

( * ) Notice: Subject to any disclaimer, the term of this patent is extended or adjusted under 35 U.S.C. 154(b) by 80 days.

(21) Appl. No.: 10/892,741

(22) Filed: Jul. 16, 2004

(65) Prior Publication Data

US 2005/0215575 A1    Sep. 29, 2005

Related U.S. Application Data

(60) Provisional application No. 60/488,551, filed on Jul. 16, 2003.

(51) Int. Cl.
- *A61K 31/517* (2006.01)
- *A61K 31/519* (2006.01)
- *C07D 401/04* (2006.01)
- *C07D 405/14* (2006.01)
- *C07D 487/04* (2006.01)

(52) U.S. Cl. ............ 514/266.21; 514/264.11; 544/279; 544/284

(58) Field of Classification Search ........... 514/266.21, 514/264.11; 544/284, 279
See application file for complete search history.

(56) References Cited

U.S. PATENT DOCUMENTS

| | | | |
|---|---|---|---|
| 5,064,833 A | 11/1991 | Ife et al. | |
| 5,814,630 A | 9/1998 | Barker et al. | |
| 5,939,421 A | 8/1999 | Palanki et al. | |
| 6,169,091 B1 | 1/2001 | Cockerill et al. | |
| 6,174,889 B1 | 1/2001 | Cockerill et al. | |
| 6,207,669 B1 | 3/2001 | Cockerill et al. | |
| 6,225,318 B1 | 5/2001 | Sobolov-Jaynes et al. | |
| 6,248,771 B1 | 6/2001 | Shenoy et al. | |
| 6,251,912 B1 | 6/2001 | Wissner et al. | |
| 6,391,874 B1 | 5/2002 | Cockerill et al. | |
| 6,399,602 B1 | 6/2002 | Barker et al. | |
| 6,413,971 B1 | 7/2002 | Arnold et al. | |
| 2004/0142958 A1* | 7/2004 | Herzberg et al. ........... 514/282 |

FOREIGN PATENT DOCUMENTS

| | | |
|---|---|---|
| EP | 1 229 025 A1 | 8/2002 |
| WO | WO89/05297 | 6/1989 |
| WO | WO95/15758 | 6/1995 |
| WO | WO96/09294 | 3/1996 |
| WO | WO99/35146 | 7/1999 |
| WO | WO 00/23444 | 4/2000 |
| WO | WO 01/04111 A1 | 1/2001 |
| WO | WO 01/21594 A1 | 3/2001 |
| WO | WO 01/21595 A1 | 3/2001 |
| WO | WO 01/21596 A1 | 3/2001 |
| WO | WO 01/21597 A1 | 3/2001 |
| WO | WO 02/22601 A1 | 3/2002 |
| WO | WO 03/62209 | 7/2003 |
| WO | WO 2004/055003 A1 | 7/2004 |

OTHER PUBLICATIONS

Temple, et al., "Synthesis of Potential Antimalarial Agents. II. 6,8-Disubstituted Pyrido[2,3-b]pyrazines," J. Med. Chem. 11:1216-1218 (1968).

Johansen, M.E. et al., "TRPV1 Antagonists Elevate Cell Surface Populations of Receptor Protein and Exacerbate TRPV1-Mediated Toxicities in Human Lung Epithelial Cells", *Toxicological Sciences* 89(1), 278-286 (2006) (Advance Access publication Aug. 24, 2005).

Thomas, Karen C. et al., "Transient Receptor Potential Vanilloid 1 Agonists Cause Endoplasmic Reticulum Stress and Cell Death in Human Lung Cells," *The Journal of Pharmacology and Experimental Therapeutics* 321(3), 830-838 (2007).

Bolcskei, Kata et al., "Investigation of the role of TRPV1 receptors in acute and chronic nociceptive processes using gene-deficient mice," *Pain* 117, 368-376 (2005).

Helyes, Zsuzsanna et al., "Role of transient receptor potential vanilloid 1 receptors in endotoxin-induced airway inflammation in the mouse," *Am J Physiol Lung Cell Mol Physiol.* 292(5):L1173-81 (2007).

Banvolgyi, Agnes et al., "Evidence for a novel protective role of the vanilloid TRPV1 receptor in a cutaneous contact allergic dermatitis model," *J Neuroimmunol.* 169, 86-96 (2005).

\* cited by examiner

*Primary Examiner*—Emily Bernhardt
*Assistant Examiner*—Tamthom N. Truong
(74) *Attorney, Agent, or Firm*—Edwards Angell Palmer & Dodge LLP; Peter F. Corless; Mark D. Russett

(57) ABSTRACT

Substituted (7-pyridyl-4-phenylamino-quinazolin-2-yl)-methanol analogues are provided. Such compounds are ligands that may be used to modulate specific receptor activity in vivo or in vitro, and are particularly useful in the treatment of conditions associated with pathological receptor activation in humans, domesticated companion animals and livestock animals. Pharmaceutical compositions and methods for using them to treat such disorders are provided, as are methods for using such ligands for receptor localization studies

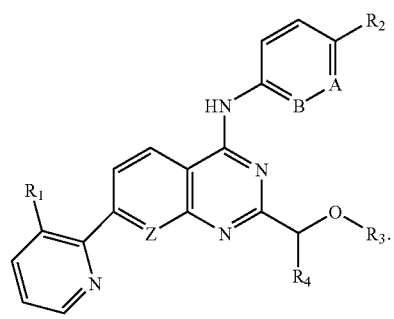

39 Claims, No Drawings

SUBSTITUTED (7-PYRIDYL-4-PHENYL-AMINO-QUINAZOLIN-2-YL)-METHANOL ANALOGUES

CROSS-REFERENCE TO RELATED APPLICATIONS

This application claims priority to U.S. Provisional Application 60/488,551, filed Jul. 16, 2003.

FIELD OF THE INVENTION

This invention relates generally to substituted (7-pyridyl-4-phenylamino-quinazolin-2-yl)-methanol analogues that are modulators of capsaicin receptors, and to the use of such compounds for treating conditions related to capsaicin receptor activation. The invention further relates to the use such compounds as probes for detecting and localizing capsaicin receptors.

BACKGROUND OF THE INVENTION

Pain perception, or nociception, is mediated by the peripheral terminals of a group of specialized sensory neurons, termed "nociceptors." A wide variety of physical and chemical stimuli induce activation of such neurons in mammals, leading to recognition of a potentially harmful stimulus. Inappropriate or excessive activation of nociceptors, however, can result in debilitating acute or chronic pain.

Neuropathic pain involves pain signal transmission in the absence of stimulus, and typically results from damage to the nervous system. In most instances, such pain is thought to occur because of sensitization in the peripheral and central nervous systems following initial damage to the peripheral system (e.g., via direct injury or systemic disease). Neuropathic pain is typically burning, shooting and unrelenting in its intensity and can sometimes be more debilitating that the initial injury or disease process that induced it.

Existing treatments for neuropathic pain are largely ineffective. Opiates, such as morphine, are potent analgesics, but their usefulness is limited because of adverse side effects, such as physical addictiveness and withdrawal properties, as well as respiratory depression, mood changes, and decreased intestinal motility with concomitant constipation, nausea, vomiting, and alterations in the endocrine and autonomic nervous systems. In addition, neuropathic pain is frequently non-responsive or only partially responsive to conventional opioid analgesic regimens. Treatments employing the N-methyl-D-aspartate antagonist ketamine or the alpha(2)-adrenergic agonist clonidine can reduce acute or chronic pain, and permit a reduction in opioid consumption, but these agents are often poorly tolerated due to side effects.

Topical treatment with capsaicin has been used to treat chronic and acute pain, including neuropathic pain. Capsaicin is a pungent substance derived from the plants of the Solanaceae family (which includes hot chili peppers) and appears to act selectively on the small diameter afferent nerve fibers (A-delta and C fibers) that are believed to mediate pain. The response to capsaicin is characterized by persistent activation of nociceptors in peripheral tissues, followed by eventual desensitization of peripheral nociceptors to one or more stimuli. From studies in animals, capsaicin appears to trigger C fiber membrane depolarization by opening cation selective channels for calcium and sodium.

Similar responses are also evoked by structural analogues of capsaicin that share a common vanilloid moiety. One such analogue is resiniferatoxin (RTX), a natural product of *Euphorbia* plants. The term vanilloid receptor (VR) was coined to describe the neuronal membrane recognition site for capsaicin and such related irritant compounds. The capsaicin response is competitively inhibited (and thereby antagonized) by another capsaicin analog, capsazepine, and is also inhibited by the non-selective cation channel blocker ruthenium red. These antagonists bind to VR with no more than moderate affinity (typically with $K_i$ values of no lower than 140 μM).

Rat and human vanilloid receptors have been cloned from dorsal root ganglion cells. The first type of vanilloid receptor to be identified is known as vanilloid receptor type 1 (VR1), and the terms "VR1" and "capsaicin receptor" are used interchangeably herein to refer to rat and/or human receptors of this type, as well as mammalian homologues. The role of VR1 in pain sensation has been confirmed using mice lacking this receptor, which exhibit no vanilloid-evoked pain behavior, and impaired responses to heat and inflammation. VR1 is a nonselective cation channel with a threshold for opening that is lowered in response to elevated temperatures, low pH, and capsaicin receptor agonists. For example, the channel usually opens at temperatures higher than about 45° C. Opening of the capsaicin receptor channel is generally followed by the release of inflammatory peptides from neurons expressing the receptor and other nearby neurons, increasing the pain response. After initial activation by capsaicin, the capsaicin receptor undergoes a rapid desensitization via phosphorylation by cAMP-dependent protein kinase.

Because of their ability to desensitize nociceptors in peripheral tissues, VR1 agonist vanilloid compounds have been used as topical anesthetics. However, agonist application may itself cause burning pain, which limits this therapeutic use. Recently, it has been reported that VR1 antagonists, including nonvanilloid compounds, are also useful for the treatment of pain (see PCT International Application Publication Number WO 02/08221, which published Jan. 31, 2002).

Thus, compounds that interact with VR1, but do not elicit the initial painful sensation of VR1 agonist vanilloid compounds, are desirable for the treatment of chronic and acute pain, including neuropathic pain. Antagonists of this receptor are particularly desirable for the treatment of pain, as well as conditions such as tear gas exposure, itch and urinary tract conditions such as urinary incontinence and overactive bladder. The present invention fulfills this need, and provides further related advantages.

SUMMARY OF THE INVENTION

The present invention provides compounds that modulate, preferably inhibit, VR1 activation. Within certain aspects, compounds provided herein are substituted (7-pyridyl-4-phenylamino-quinazolin-2-yl)-methanol analogues of Formula I:

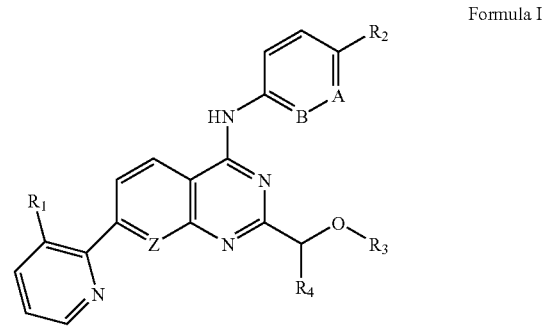

Formula I as well as pharmaceutically acceptable forms thereof. Within Formula I:

A, B and Z are independently CH or N, such that at least one of A and B is CH;

$R_1$ is halogen or methyl substituted with from 0 to 3 halogen;

$R_2$ is: (i) halogen or cyano; or (ii) $C_1$-$C_4$alkyl or $C_3$-$C_4$cycloalkyl, each of which is optionally substituted with cyano, methoxy, ethanoyl or from 1 to 3 halogen;

$R_3$ is: (i) hydrogen; (ii) $C_1$-$C_4$alkyl, substituted with from 0 to 2 substituents independently selected from methoxy and ethoxy; or (iii) benzyl or a group of the formula:

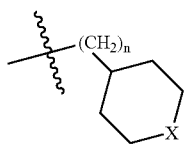

wherein n is 0 or 1 and X is NH or O; each of which benzyl or group is substituted with from 0 to 2 substituents independently selected from halogen and methyl; and $R_4$ is hydrogen or methyl.

Within certain aspects, compounds as described herein exhibit a $K_i$ of no greater than 10 nanomolar, 1 nanomolar, 0.5 nanomolar, 0.25 nanomolar or 0.1 nanomolar in a capsaicin receptor binding assay and/or have an $IC_{50}$ value of no greater than 10 nanomolar, 1 nanomolar, 0.5 nanomolar, 0.25 nanomolar or 0.1 nanomolar in an assay for determination of capsaicin receptor antagonist activity. Preferred compounds are generally those with higher potency (i.e., lower $K_i$ or lower $IC_{50}$).

In certain embodiments, VR1 modulators as described herein are VR1 antagonists and exhibit no detectable agonist activity in an in vitro assay of capsaicin receptor activation.

Within certain aspects, VR1 modulators as described herein are labeled with a detectable marker (e.g., radiolabeled or fluorescein conjugated).

Within certain aspects, VR1 modulators and pharmaceutically acceptable forms thereof as described herein are labeled with a detectable marker (e.g., radiolabeled or fluorescein conjugated).

The present invention further provides, within other aspects, pharmaceutical compositions comprising at least one VR1 modulator as described herein (i.e., a compound as provided herein or a pharmaceutically acceptable form thereof) in combination with a physiologically acceptable carrier or excipient.

Within further aspects, methods are provided for reducing calcium conductance of a cellular capsaicin receptor, comprising contacting a cell (e.g., neuronal) expressing a capsaicin receptor with a capsaicin receptor modulatory amount of at least one VR1 modulator as described herein. Such contact may occur in vivo or in vitro.

Methods are further provided for inhibiting binding of vanilloid ligand to a capsaicin receptor. Within certain such aspects, the inhibition takes place in vitro. Such methods comprise contacting a capsaicin receptor with at least one VR1 modulator as described herein, under conditions and in an amount sufficient to detectably inhibit vanilloid ligand binding to the capsaicin receptor. Within other such aspects, the capsaicin receptor is in a patient. Such methods comprise contacting cells expressing a capsaicin receptor in a patient with at least one VR1 modulator as described herein in an amount sufficient to detectably inhibit vanilloid ligand binding to cells expressing a cloned capsaicin receptor in vitro, and thereby inhibiting binding of vanilloid ligand to the capsaicin receptor in the patient.

The present invention further provides methods for treating a condition responsive to capsaicin receptor modulation in a patient, comprising administering to the patient a capsaicin receptor modulatory amount of at least one VR1 modulator as described herein.

Within other aspects, methods are provided for treating pain in a patient, comprising administering to a patient suffering from pain a capsaicin receptor modulatory amount of at least one VR1 modulator as described herein.

Methods are further provided for treating itch, urinary incontinence, overactive bladder, cough and/or hiccup in a patient, comprising administering to a patient suffering from one or more of the foregoing conditions a capsaicin receptor modulatory amount of at least one VR1 modulator as described herein.

The present invention further provides methods for promoting weight loss in an obese patient, comprising administering to an obese patient a capsaicin receptor modulatory amount of at least one VR1 modulator as described herein.

Within further aspects, the present invention provides methods for determining the presence or absence of capsaicin receptor in a sample, comprising: (a) contacting a sample with a VR1 modulator as described herein under conditions that permit binding of the VR1 modulator to capsaicin receptor; and (b) detecting a level of the VR1 modulator bound to capsaicin receptor.

The present invention also provides packaged pharmaceutical preparations, comprising: (a) a pharmaceutical composition as described herein in a container; and (b) instructions for using the composition to treat one or more conditions responsive to capsaicin receptor modulation, such as pain, itch, urinary incontinence, overactive bladder, cough, hiccup and/or obesity.

In yet another aspect, the invention provides methods of preparing the compounds disclosed herein, including the intermediates.

These and other aspects of the present invention will become apparent upon reference to the following detailed description.

DETAILED DESCRIPTION

As noted above, the present invention provides substituted (7-pyridyl-4-phenylamino-quinazolin-2-yl)-methanol analogues. Such compounds may be used in vitro or in vivo, to modulate (preferably inhibit) capsaicin receptor activity in a variety of contexts.

Terminology

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that includes variables (e.g., $R_1$-$R_4$, A, B, Z). Unless otherwise specified, each variable within such a formula is defined independently of any other variable, and any variable that occurs more than one time in a formula is defined independently at each occurrence.

The term "(7-pyridyl-4-phenylamino-quinazolin-2-yl)-methanol analogues," as used herein, encompasses all compounds of Formula I, as well as pharmaceutically acceptable forms of such compounds.

"Pharmaceutically acceptable forms" of the compounds recited herein are pharmaceutically acceptable salts, hydrates, solvates, crystal forms, polymorphs, chelates, non-covalent complexes, esters, clathrates and prodrugs of such compounds. As used herein, a pharmaceutically acceptable salt is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences*, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred.

A "prodrug" is a compound that may not fully satisfy the structural requirements of the compounds provided herein, but is modified in vivo, following administration to a patient, to produce a compound of Formula I, or other formula provided herein. For example, a prodrug may be an acylated derivative of a compound as provided herein. Prodrugs include compounds wherein hydroxy, amine or sulflhydryl groups are bonded to any group that, when administered to a mammalian subject, cleaves to form a free hydroxy, amino, or sulflhydryl group, respectively. Examples of prodrugs include, but are not limited to, acetate, formate and benzoate derivatives of alcohol and amine functional groups within the compounds provided herein. Prodrugs of the compounds provided herein may be prepared by modifying functional groups present in the compounds in such a way that the modifications are cleaved to the parent compounds.

As used herein, the term "alkyl" refers to a straight or branched chain, saturated aliphatic hydrocarbon. Alkyl groups include groups having from 1 to 4 carbon atoms ($C_1$-$C_4$alkyl), such as methyl, ethyl, propyl, isopropyl, n-butyl, sec-butyl, tert-butyl. "$C_0$-$C_2$alkyl" refers to a single covalent bond ($C_0$) or an alkyl group having 1 or 2 carbon atoms; "$C_0$-$C_1$alkyl" refers to a single covalent bond or a methylene group.

A "cycloalkyl" is a saturated cyclic group in which all ring members are carbon, such as cyclopropyl or cyclobutyl. Certain cycloalkyl groups are $C_3$-$C_4$cycloalkyl (i.e., cyclopropyl or cyclobutyl).

Similarly, "alkenyl" refers to straight or branched chain alkene groups, in which at least one unsaturated carbon-carbon double bond is present. Alkenyl groups include, for example, $C_2$-$C_4$alkenyl, which have from 2 to 4 carbon atoms, respectively, such as ethenyl, allyl or isopropenyl. "Alkynyl" refers to straight or branched chain alkyne groups, which have one or more unsaturated carbon-carbon bonds, at least one of which is a triple bond. Alkynyl groups include, for example, $C_2$-$C_4$alkynyl groups, which have from 2 to 4 carbon atoms.

The term "halogen" refers to fluorine, chlorine, bromine or iodine.

A "haloalkyl" is a branched, straight-chain or cyclic alkyl group, substituted with 1 or more halogen atoms (e.g., "$C_1$-$C_4$haloalkyl" groups have from 1 to 4 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl. Typical haloalkyl groups are trifluoromethyl and difluoromethyl.

A dash ("-") that is not between two letters or symbols is used to indicate a point of attachment for a substituent. For example, —$CONH_2$ is attached through the carbon atom.

A "heteroatom," as used herein, is oxygen, sulfur or nitrogen.

A "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution.

Groups that are "optionally substituted" are unsubstituted or are substituted by other than hydrogen at one or more available positions, typically 1, 2, 3, 4 or 5 positions, by one or more suitable groups (which may be the same or different). Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substitutents).

The terms "VR1" and "capsaicin receptor" are used interchangeably herein to refer to a type 1 vanilloid receptor. Unless otherwise specified, these terms encompass both rat and human VR1 receptors (e.g., GenBank Accession Numbers AF327067, AJ277028 and NM_018727; sequences of certain human VR1 cDNAs and the encoded amino acid sequences are recited in U.S. Pat. No. 6,482,611), as well as homologues thereof found in other species.

A "VR1 modulator," also referred to herein as a "modulator," is a compound that modulates VR1 activation and/or VR1-mediated signal transduction. VR1 modulators specifically provided herein are compounds of Formula I and pharmaceutically acceptable forms of compounds of Formula I. A VR1 modulator may be a VR1 agonist or antagonist. A modulator binds with "high affinity" if the $K_i$ at VR1 is less than 1 micromolar, preferably less than 100 nanomolar, 10 nanomolar or 1 nanomolar. A representative assay for determining $K_i$ at VR1 is provided in Example 5, herein.

A modulator is considered an "antagonist" if it detectably inhibits vanilloid ligand binding to VR1 and/or VR1-mediated signal transduction (using, for example, the representative assay provided in Example 6); in general, such an antagonist inhibits VR1 activation with a $IC_{50}$ value of less than 1 micromolar, preferably less than 100 nanomolar, and more preferably less than 10 nanomolar or 1 nanomolar within the assay provided in Example 6. VR1 antagonists include neutral antagonists and inverse agonists. In certain embodiments, capsaicin receptor antagonists provided herein are not vanilloids.

An "inverse agonist" of VR1 is a compound that reduces the activity of VR1 below its basal activity level in the absence of added vanilloid ligand. Inverse agonists of VR1 may also inhibit the activity of vanilloid ligand at VR1, and/or may also inhibit binding of vanilloid ligand to VR1. The ability of a compound to inhibit the binding of vanilloid ligand to VR1 may be measured by a binding assay, such as the binding assay given in Example 5. The basal activity of VR1, as well as the reduction in VR1 activity due to the presence of VR1 antagonist, may be determined from a calcium mobilization assay, such as the assay of Example 6.

A "neutral antagonist" of VR1 is a compound that inhibits the activity of vanilloid ligand at VR1, but does not significantly change the basal activity of the receptor (i.e., within a calcium mobilization assay as described in Example 6 performed in the absence of vanilloid ligand, VR1 activity is reduced by no more than 10%, more preferably by no more than 5%, and even more preferably by no more than 2%; most preferably, there is no detectable reduction in activity). Neutral antagonists of VR1 may inhibit the binding of vanilloid ligand to VR1.

As used herein a "capsaicin receptor agonist" or "VR1 agonist" is a compound that elevates the activity of the receptor above the basal activity level of the receptor (i.e., enhances VR1 activation and/or VR1-mediated signal transduction). Capsaicin receptor agonist activity may be identified using the representative assay provided in Example 6. In general, such an agonist has an $EC_{50}$ value of less than 1 micromolar, preferably less than 100 nanomolar, and more preferably less than 10 nanomolar within the assay provided in Example 6. In certain embodiments, capsaicin receptor agonists provided herein are not vanilloids.

A "vanilloid" is capsaicin or any capsaicin analogue that comprises a phenyl ring with two oxygen atoms bound to adjacent ring carbon atoms (one of which carbon atom is located para to the point of attachment of a third moiety that is bound to the phenyl ring). A vanilloid is a "vanilloid ligand" if it binds to VR1 with a $K_i$ (determined as described herein) that is no greater than 10 μM. Vanilloid ligand agonists include capsaicin, olvanil, N-arachidonoyl-dopamine and resiniferatoxin (RTX). Vanilloid ligand antagonists include capsazepine and iodo-resiniferatoxin.

A "capsaicin receptor modulatory amount" is an amount that, upon administration to a patient, achieves a concentration of VR1 modulator at a capsaicin receptor within the patient that is sufficient to alter the binding of vanilloid ligand to VR1 in vitro (using the assay provided in Example 5) and/or VR1-mediated signal transduction (using an assay provided in Example 6). The capsaicin receptor may be present, or example, in a body fluid such as blood, plasma, serum, CSF, synovial fluid, lymph, cellular interstitial fluid, tears or urine.

A "therapeutically effective amount" is an amount that, upon administration, is sufficient to provide detectable patient relief from a condition being treated. Such relief may be detected using any appropriate criteria, including alleviation of one or more symptoms such as pain.

A "patient" is any individual treated with a VR1 modulator as provided herein. Patients include humans, as well as other animals such as companion animals (e.g., dogs and cats) and livestock. Patients may be experiencing one or more symptoms of a condition responsive to capsaicin receptor modulation (e.g., pain, exposure to vanilloid ligand, itch, urinary incontinence, overactive bladder, respiratory disorders, cough and/or hiccup), or may be free of such symptom(s) (i.e., treatment may be prophylactic).

VR1 Modulators

As noted above, the present invention provides VR1 modulators that may be used in a variety of contexts, including in the treatment of pain (e.g., neuropathic or peripheral nerve-mediated pain); exposure to capsaicin; exposure to acid, heat, light, tear gas air pollutants, pepper spray or related agents; respiratory conditions such as asthma or chronic obstructive pulmonary disease; itch; urinary incontinence or overactive bladder; cough or hiccup; and/or obesity. VR1 modulators may also be used within in vitro assays (e.g., assays for receptor activity), as probes for detection and localization of VR1 and as standards in ligand binding and VR1-mediated signal transduction assays.

VR1 modulators provided herein are substituted (7-pyridyl-4-phenylamino-quinazolin-2-yl)-methanol analogues that detectably modulate the binding of capsaicin to VR1 at nanomolar (i.e., submicromolar) concentrations, preferably at subnanomolar concentrations, more preferably at concentrations below 100 picomolar, 20 picomolar, 10 picomolar or 5 picomolar. Such modulators are preferably not capsaicin analogs (i.e., they do not comprise a phenyl ring with two oxygen atoms bound to adjacent ring carbons). Preferred modulators are VR1 antagonists and have no detectable agonist activity in the assay described in Example 6. In certain embodiments, such modulators further bind with high affinity to VR1, and do not substantially inhibit activity of human EGF receptor tyrosine kinase.

The present invention is based, in part, on the discovery that small molecules having the general Formula I (as well as pharmaceutically acceptable forms thereof) are highly active modulators of VR1 activity.

Formula I

Within Formula I, A, B and Z are independently CH or N, such that at least one of A and B is CH. In certain embodiments, A, B and Z have the values shown below:

| Embodiment | A | B | Z |
|---|---|---|---|
| 1 | N | CH | CH |
| 2 | CH | N | CH |
| 3 | CH | CH | CH |
| 4 | N | CH | N |
| 5 | CH | N | N |
| 6 | CH | CH | N |

R₁ of Formula I is halogen or methyl substituted with from 0 to 3 halogen. Representative R₁ groups include chloro, methyl and trifluoromethyl.

R₂ of Formula I is: (i) halogen or cyano; or (ii) $C_1$-$C_4$alkyl or $C_3$-$C_4$cycloalkyl, each of which is optionally substituted with a single cyano, methoxy or ethanoyl group, or with from 1 to 3 halogen. In certain embodiments, R₂ is methyl, mono-, di- or tri-fluoromethyl, isopropyl (optionally substituted with cyano, ethanoyl or trifluoro), tert-butyl (optionally substituted with methoxy), sec-butyl, di- or tri-fluoromethyl, cyclopropyl or cyclobutyl (optionally substituted with cyano).

R₃ of Formula I is: (i) hydrogen; (ii) $C_1$-$C_4$alkyl, substituted with from 0 to 2 substituents independently selected from methoxy and ethoxy; or (iii) benzyl or a group of the formula:

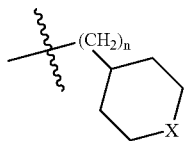

wherein n is 0 or 1 and X is NH or O; each of which benzyl or group is substituted with from 0 to 2 substituents independently selected from halogen and methyl. Representative R₃ groups include, for example, hydrogen, methyl, ethyl (optionally substituted with methoxy or ethoxy), isopropyl, isobutyl, cyclopropylmethyl, benzyl and tetrahydropyran-4-yl. In certain embodiments, R₃ is methyl, ethyl or isobutyl.

R₄ of Formula I is hydrogen or methyl; in certain embodiments, R₄ is hydrogen.

In certain embodiments, VR1 modulators provided herein satisfy Formula II, III, IV, V VI or VII:

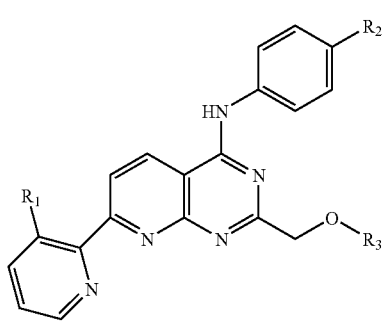

Formula II

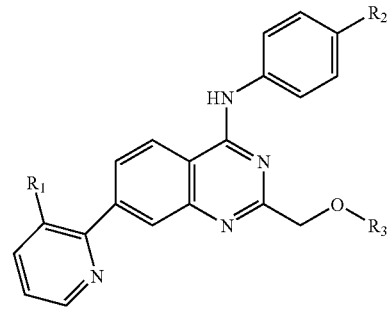

Formula III

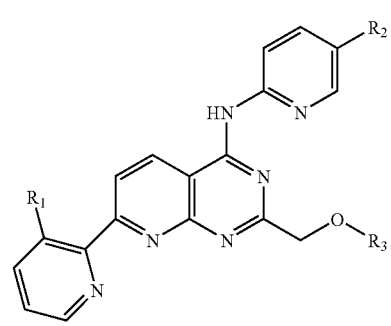

Formula IV

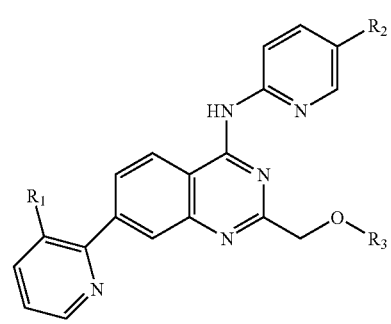

Formula V

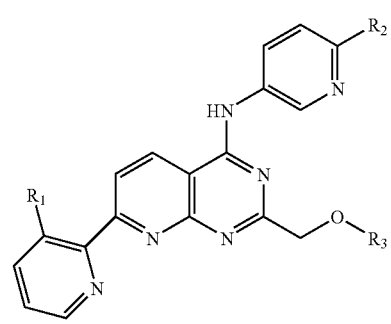

Formula VI

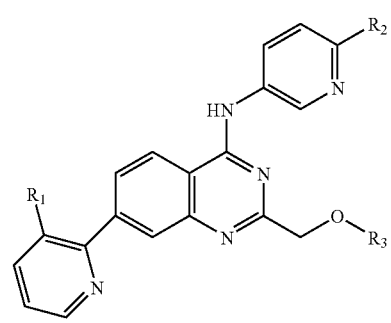

Formula VII wherein $R_1$ is chloro, methyl or trifluoromethyl; $R_2$ is $C_1$-$C_4$alkyl (such as isopropyl and tert-butyl), halo$C_1$-$C_4$alkyl (such as trifluoromethyl) or cyano$C_1$-$C_4$alkyl; and $R_3$ is hydrogen or $C_1$-$C_4$alkyl, and preferably $R_3$ is $C_1$-$C_4$alkyl. In certain embodiments, $R_3$ is methyl, ethyl or isobutyl.

Representative compounds of the above Formulas include, but are not limited to, those specifically described in Examples 1-3. It will be apparent that the specific compounds recited therein are representative only, and are not intended to limit the scope of the present invention. Further, as noted above, all compounds of the present invention may be present as a pharmaceutically acceptable form, such as a prodrug, hydrate, free base or a pharmaceutically acceptable acid addition salt.

Substituted (7-pyridyl-4-phenylamino-quinazolin-2-yl)-methanol analogues provided herein detectably alter (modulate) VR1 activity, as determined using an in vitro VR1 ligand binding assay and/or a functional assay such as a calcium mobilization assay, dorsal root ganglion assay or in vivo pain relief assay. References herein to a "VR1 ligand binding assay" are intended to refer to a standard in vitro receptor binding assay such as that provided in Example 5, and a "calcium mobilization assay" (also referred to herein as a "signal transduction assay") may be performed as described in Example 6. Briefly, to assess binding to VR1, a competition assay may be performed in which a VR1 preparation is incubated with labeled (e.g., $^{125}$I or $^3$H) compound that binds to VR1 (e.g., a capsaicin receptor agonist such as RTX) and unlabeled test compound. Within the assays provided herein, the VR1 used is preferably mammalian VR1, more preferably human or rat VR1. The receptor may be recombinantly expressed or naturally expressed. The VR1 preparation may be, for example, a membrane preparation from HEK293 or CHO cells that recombinantly express human VR1. Incubation with a compound that detectably modulates vanilloid ligand binding to VR1 results in a decrease or increase in the amount of label bound to the VR1 preparation, relative to the amount of label bound in the absence of the compound. This decrease or increase may be used to determine the $K_i$ at VR1 as described herein. In general, compounds that decrease the amount of label bound to the VR1 preparation within such an assay are preferred.

As noted above, compounds that are VR1 antagonists are preferred within certain embodiments. $IC_{50}$ values for such compounds may be determined using a standard in vitro VR1-mediated calcium mobilization assay, as provided in Example 6. Briefly, cells expressing capsaicin receptor are contacted with a compound of interest and with an indicator of intracellular calcium concentration (e.g., a membrane permeable calcium sensitivity dye such as Fluo-3 or Fura-2 (both of which are available, for example, from Molecular Probes, Eugene, Oreg.), each of which produce a fluorescent signal when bound to $Ca^{++}$). Such contact is preferably carried out by one or more incubations of the cells in buffer or culture medium comprising either or both of the compound and the indicator in solution. Contact is maintained for an amount of time sufficient to allow the dye to enter the cells (e.g., 1-2 hours). Cells are washed or filtered to remove excess dye and are then contacted with a vanilloid receptor agonist (e.g., capsaicin, RTX or olvanil), typically at a concentration equal to the $EC_{50}$ concentration, and a fluorescence response is measured. When agonist-contacted cells are contacted with a compound that is a VR1 antagonist the fluorescence response is generally reduced by at least 20%, preferably at least 50% and more preferably at least 80%, as compared to cells that are contacted with the agonist in the absence of test compound. The $IC_{50}$ for VR1 antagonists provided herein is preferably less than 1 micromolar, less than 100 nM, less than 10 nM or less than 1 nM.

In other embodiments, compounds that are capsaicin receptor agonists are preferred. Capsaicin receptor agonist activity may generally be determined as described in Example 6. When cells are contacted with 1 micromolar of a compound that is a VR1 agonist, the fluorescence response is generally increased by an amount that is at least 30% of the increase observed when cells are contacted with 100 nM capsaicin. The $EC_{50}$ for VR1 agonists provided herein is preferably less than 1 micromolar, less than 100 nM or less than 10 nM.

VR1 modulating activity may also, or alternatively, be assessed using a cultured dorsal root ganglion assay as provided in Example 9 and/or an in vivo pain relief assay as provided in Example 10. Compounds provided herein preferably have a statistically significant specific effect on VR1 activity within one or more functional assays provided herein.

Within certain embodiments, VR1 modulators provided herein do not substantially modulate ligand binding to other cell surface receptors, such as EGF receptor tyrosine kinase or the nicotinic acetylcholine receptor. In other words, such modulators do not substantially inhibit activity of a cell surface receptor such as the human epidermal growth factor (EGF) receptor tyrosine kinase or the nicotinic acetylcholine receptor (e.g., the $IC_{50}$ or $IC_{40}$ at such a receptor is preferably greater than 1 micromolar, and most preferably greater than 10 micromolar). Preferably, a modulator does not detectably inhibit EGF receptor activity or nicotinic acetylcholine receptor activity at a concentration of 0.5 micromolar, 1 micromolar or more preferably 10 micromolar. Assays for determining cell surface receptor activity are commercially available, and include the tyrosine kinase assay kits available from Panvera (Madison, Wis.).

Preferred VR1 modulators provided herein are non-sedating. In other words, a dose of VR1 modulator that is twice the minimum dose sufficient to provide analgesia in an animal model for determining pain relief (such as a model provided in Example 10, herein) causes only transient (i.e., lasting for no more than ½ the time that pain relief lasts) or preferably no statistically significant sedation in an animal model assay of sedation (using the method described by Fitzgerald et al. (1988) *Toxicology* 49(2-3):433-9). Preferably, a dose that is five times the minimum dose sufficient to provide analgesia does not produce statistically significant sedation. More preferably, a VR1 modulator provided herein does not produce sedation at intravenous doses of less than 25 mg/kg (preferably less than 10 mg/kg) or at oral doses of less than 140 mg/kg (preferably less than 50 mg/kg, more preferably less than 30 mg/kg).

If desired, VR1 modulators provided herein may be evaluated for certain pharmacological properties including, but not limited to, oral bioavailability (preferred compounds are orally bioavailable to an extent allowing for therapeutically effective concentrations of the compound to be achieved at oral doses of less than 140 mg/kg, preferably less than 50 mg/kg, more preferably less than 30 mg/kg, even more preferably less than 10 mg/kg, still more preferably less than 1 mg/kg and most preferably less than 0.1 mg/kg), toxicity (a preferred VR1 modulator is nontoxic when a capsaicin receptor modulatory amount is administered to a subject), side effects (a preferred VR1 modulator produces side effects comparable to placebo when a therapeutically effective amount of the compound is administered to a subject), serum protein binding and in vitro and in vivo half-life (a preferred VR1 modulator exhibits an in vitro half-life that is equal to an in vivo half-life allowing for Q.I.D. dosing, preferably T.I.D. dosing, more preferably B.I.D. dosing, and most preferably once-a-day dosing). In addition, differential penetration of the blood brain barrier may be desirable for VR1 modulators used to treat pain by modulating CNS VR1 activity such that total daily oral doses as described above provide such modulation to a therapeutically effective extent, while low brain levels of VR1 modulators used to treat peripheral nerve mediated pain may be preferred (i.e., such doses do not provide brain (e.g., CSF) levels of the compound sufficient to significantly modulate VR1 activity). Routine assays that are well known in the art may be used to assess these properties, and identify superior compounds for a particular use. For example, assays used to predict bioavailability include transport across human intestinal cell monolayers, including Caco-2 cell monolayers. Penetration of the blood brain barrier of a compound in humans may be predicted from the brain levels of the compound in laboratory animals given the compound (e.g., intravenously). Serum protein binding may be predicted from albumin binding assays. Compound half-life is inversely proportional to the frequency of dosage of a compound. In vitro half-lives of compounds may be predicted from assays of microsomal half-life as described within Example 7, herein.

As noted above, preferred VR1 modulators provided herein are nontoxic. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, and (4) does not cause substantial release of liver enzymes.

As used herein, a VR1 modulator that "does not substantially inhibit cellular ATP production" is a compound that satisfies the criteria set forth in Example 8, herein. In other words, cells treated as described in Example 8 with 100 µM of such a compound exhibit ATP levels that are at least 50% of the ATP levels detected in untreated cells. In more highly preferred embodiments, such cells exhibit ATP levels that are at least 80% of the ATP levels detected in untreated cells.

A VR1 modulator that "does not significantly prolong heart QT intervals" is a compound that does not result in a statistically significant prolongation of heart QT intervals (as determined by electrocardiography) in guinea pigs, minipigs or dogs upon administration of twice the minimum dose yielding a therapeutically effective in vivo concentration. In certain preferred embodiments, a dose of 0.01, 0.05. 0.1, 0.5, 1, 5, 10, 40 or 50 mg/kg administered parenterally or orally does not result in a statistically significant prolongation of heart QT intervals. By "statistically significant" is meant results varying from control at the $p<0.1$ level or more preferably at the $p<0.05$ level of significance as measured using a standard parametric assay of statistical significance such as a student's T test.

A VR1 modulator "does not cause substantial liver enlargement" if daily treatment of laboratory rodents (e.g., mice or rats) for 5-10 days with twice the minimum dose that yields a therapeutically effective in vivo concentration results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05. 0.1, 0.5, 1, 5, 10, 40 or 50 mg/kg administered parenterally or orally.

Similarly, a VR1 modulator "does not promote substantial release of liver enzymes" if administration of twice the minimum dose yielding a therapeutically effective in vivo concentration does not elevate serum levels of ALT, LDH or AST in laboratory rodents by more than 100% over matched mock-treated controls. In more highly preferred embodiments, such doses do not elevate such serum levels by more than 75% or 50% over matched controls. Alternatively, a VR1 modulator "does not promote substantial release of liver enzymes" if, in an in vitro hepatocyte assay, concentrations (in culture media or other such solutions that are contacted and incubated with hepatocytes in vitro) equivalent to two-fold the minimum in vivo therapeutic concentration of the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the minimum in vivo therapeutic concentration of the compound.

In other embodiments, certain preferred VR1 modulators do not inhibit or induce microsomal cytochrome P450 enzyme activities, such as CYP1A2 activity, CYP2A6 activity, CYP2C9 activity, CYP2C 19 activity, CYP2D6 activity, CYP2E1 activity or CYP3A4 activity at a concentration equal to the minimum therapeutically effective in vivo concentration.

Certain preferred VR1 modulators are not clastogenic (e.g., as determined using a mouse erythrocyte precursor cell micronucleus assay, an Ames micronucleus assay, a spiral micronucleus assay or the like) at a concentration equal to the minimum therapeutically effective in vivo concentration. In other embodiments, certain preferred VR1 modulators do not induce sister chromatid exchange (e.g., in Chinese hamster ovary cells) at such concentrations.

For detection purposes, as discussed in more detail below, VR1 modulators provided herein may be isotopically-labeled or radiolabeled. For example, compounds recited in Formulas I-III may have one or more atoms replaced by an atom of the same element having an atomic mass or mass number different from the atomic mass or mass number usually found in nature. Examples of isotopes that can be present in the compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Preparation of VR1 Modulators

Substituted (7-pyridyl-4-phenylamino-quinazolin-2-yl)-methanol analogues may generally be prepared using standard synthetic methods. Starting materials are commercially available from suppliers such as Sigma-Aldrich Corp. (St. Louis, Mo.), or may be synthesized from commercially available precursors using established protocols. By way of example, a synthetic route similar to that shown in any of Schemes 1-3 may be used, together with synthetic methods known in the art of synthetic organic chemistry, or variations thereon as appreciated by those skilled in the art. Each variable in the following schemes refers to any group consistent with the description of the compounds provided herein.

In the Schemes that follow, the term "catalyst" refers to a suitable transition metal catalyst such as, but not limited to, tetrakis(triphenylphosphine)palladium(0) or palladium(II) acetate. In addition, the catalytic systems may include ligands such as, but not limited to, 2-(Dicyclohexylphosphino)biphenyl and tri-tert-butylphosphine, and may also include a base such as $K_3PO_4$, $Na_2CO_3$ or sodium or potassium tert-butoxide. Transition metal-catalyzed reactions can be carried out at ambient or elevated temperatures using various inert solvents including, but not limited to, toluene, dioxane, DMF, N-methylpyrrolidinone, ethyleneglycol, dimethyl ether, diglyme and acetonitrile. When used in conjunction with suitable metallo-aryl reagents, transition metal-catalyzed (hetero)aryl-aryl coupling reactions can be used to prepare the compounds encompassed in general structures 1C (Scheme 1) and 2A (Scheme 2). Commonly employed reagent/catalyst pairs include aryl boronic acid/palladium(0) (Suzuki reaction; Miyaura and Suzuki (1995) *Chemical Reviews* 95:2457) and aryl trialkylstannane/palladium(0) (Stille reaction; T. N. Mitchell, (1992) *Synthesis* 9:803-815), arylzinc/palladium(0) and aryl Grignard/nickel (II).

The term "reduce" refers to the process of reducing a nitro functionality to an amino functionality. This transformation can be carried out in a number of ways well known to those skilled in the art of organic synthesis including, but not limited to, catalytic hydrogenation, reduction with $SnCl_2$ and reduction with titanium trichloride. For an overview of reduction methods see: Hudlicky, M. *Reductions in Organic Chemistry*, ACS Monograph 188, 1996.

The term "activate" refers to a synthetic transformation in which a carbonyl of an amide moiety is converted to a suitable leaving group (L). Such a transformation can be used to prepare compounds of general structure II (Scheme 1), 2G (Scheme 2) and 3H (Scheme 3). Reagents suitable for carrying out this transformation are well known to those skilled in the art of organic synthesis and include, but are not limited to, $SOCl_2$, $POCl_3$ and triflic anhydride.

The term "oxidize" refers to a synthetic transformation wherein a methyl group is converted to a carboxylic acid functionality. Such a transformation can be used to prepare compounds such as 1E (Scheme 1). Various reagents familiar to those skilled in the art of organic synthesis may be used to carry out this transformation including, but not limited to, $KMnO_4$ in basic media (e.g., NaOH solution or aqueous pyridine) and $K_2Cr_2O_7$ in acidic media (e.g., $H_2SO_4$).

Scheme 1

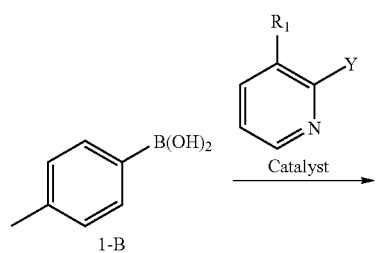

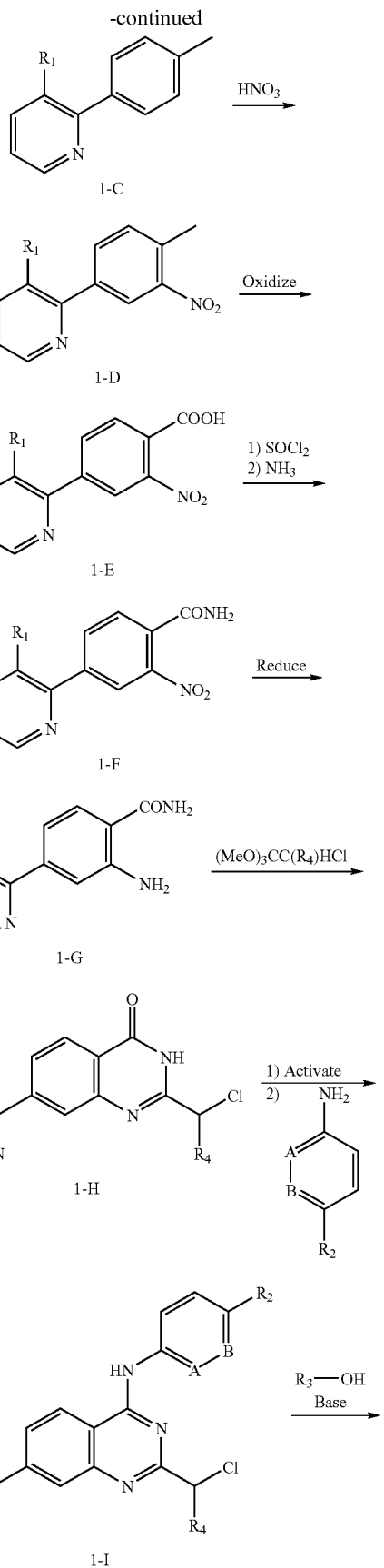

-continued
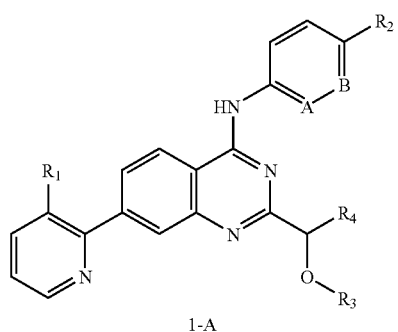
1-A
Scheme 2
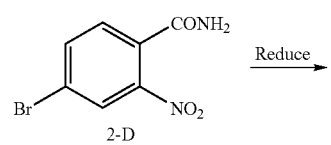
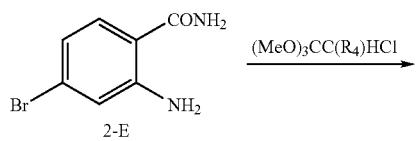
-continued
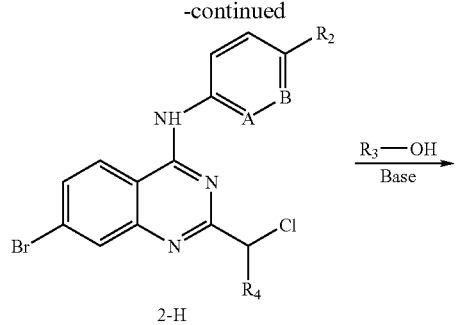
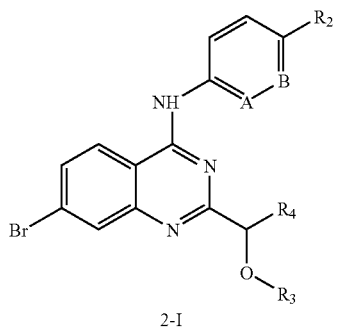
2-A
Scheme 3
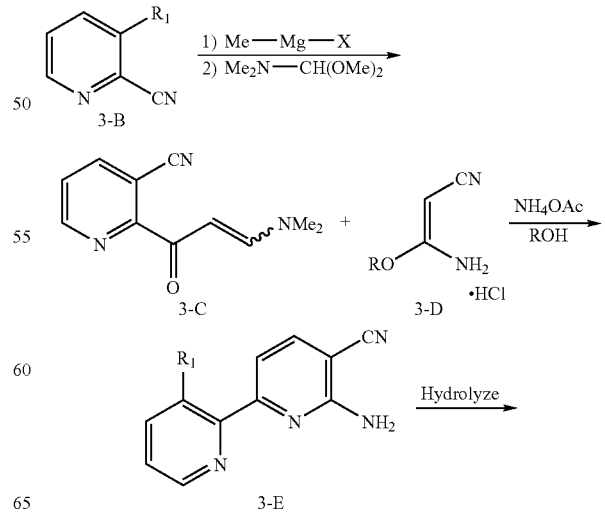
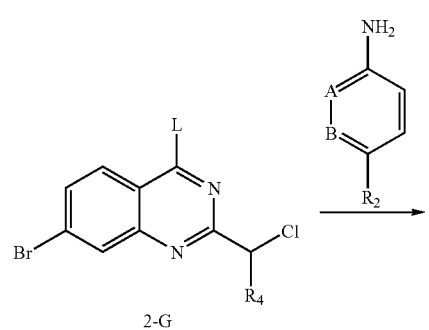
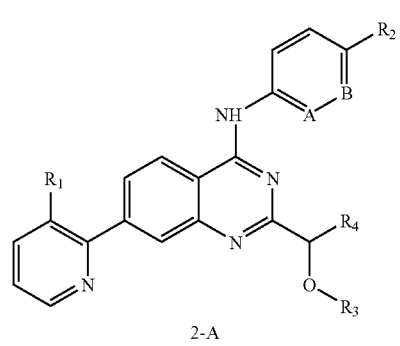

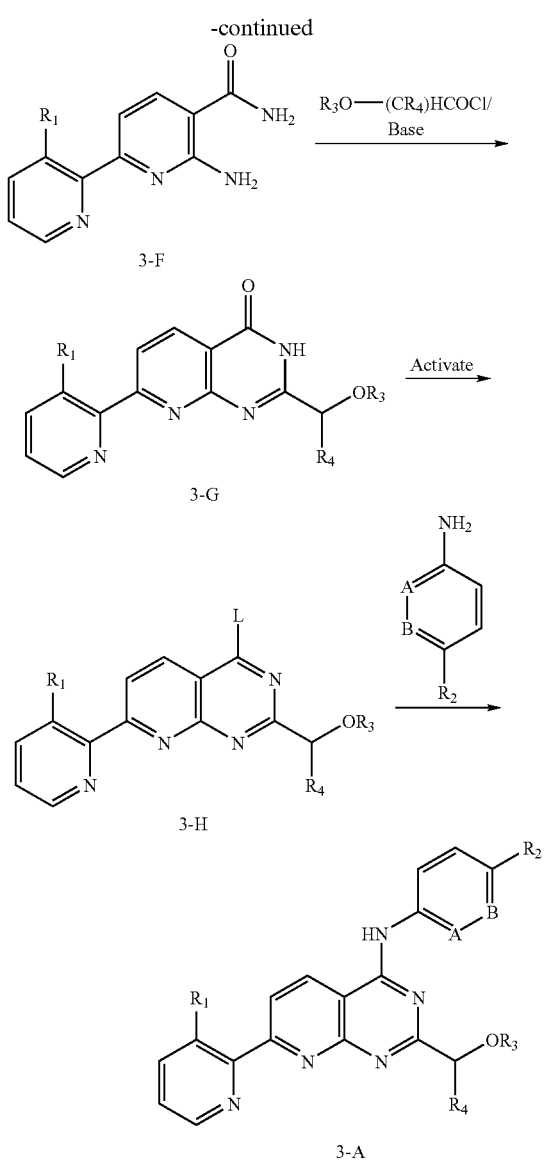

In certain embodiments, a VR1 modulator may contain one or more asymmetric carbon atoms, so that the compound can exist in different stereoisomeric forms. Such forms can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column.

Compounds may be radiolabeled by carrying out their synthesis using precursors comprising at least one atom that is a radioisotope. Each radioisotope is preferably carbon (e.g., $^{14}C$), hydrogen (e.g., $^{3}H$), sulfur (e.g., $^{35}S$), or iodine (e.g., $^{125}I$). Tritium labeled compounds may also be prepared catalytically via platinum-catalyzed exchange in tritiated acetic acid, acid-catalyzed exchange in tritiated trifluoroacetic acid, or heterogeneous-catalyzed exchange with tritium gas using the compound as substrate. In addition, certain precursors may be subjected to tritium-halogen exchange with tritium gas, tritium gas reduction of unsaturated bonds, or reduction using sodium borotritide, as appropriate. Preparation of radiolabeled compounds may be conveniently performed by a radioisotope supplier specializing in custom synthesis of radiolabeled probe compounds.

Pharmaceutical Compositions

The present invention also provides pharmaceutical compositions comprising one or more VR1 modulators, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. In addition, other active ingredients may (but need not) be included in the pharmaceutical compositions provided herein.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions suitable for oral use are preferred. Such compositions include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate. Formulation for topical administration may be preferred for certain conditions (e.g., in the treatment of skin conditions such as burns or itch). Formulation for direct administration into the bladder (intravesicular administration) may be preferred for treatment of urinary incontinence and overactive bladder.

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, such as ethyl or n-propyl p-hydroxybenzoate, one or more coloring agents, one or more flavoring agents, and one or more sweetening agents, such as sucrose or saccharin.

Oily suspensions may be formulated by suspending the active ingredient(s) in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be formulated as oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids and emulsions. The physical appearance and viscosity of such pharmaceutically acceptable forms can be governed by the presence and amount of emulsifier(s) and viscosity adjuster(s) present in the formulation. Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations. Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included a topical formulation include, but are not limited to, abrasives, absorbents, anti-caking agents, anti-foaming agents, anti-static agents, astringents (e.g., witch hazel, alcohol and herbal extracts such as chamomile extract), binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quatemium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying (including mist, aerosol or foam spraying); dropper application; sprinkling; soaking; and rinsing. Controlled release vehicles can also be used.

A pharmaceutical composition may be prepared as a sterile injectable aqueous or oleaginous suspension. The modulator, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions, and adjuvants such as local anesthetics, preservatives and/or buffering agents can be dissolved in the vehicle.

Modulators may also be formulated as suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In addition to or together with the above modes of administration, a modulator may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Modulators are generally administered in a capsaicin receptor modulatory amount, and preferably a therapeutically effective amount. Preferred systemic doses are no higher than 50 mg per kilogram of body weight per day (e.g., ranging from about 0.001 mg to about 50 mg per kilogram of body weight per day), with oral doses generally being about 5-20 fold higher than intravenous doses (e.g., ranging from 0.01 to 40 mg per kilogram of body weight per day).

The amount of active ingredient that may be combined with the carrier materials to produce a single dosage unit will vary depending, for example, upon the patient being treated and the particular mode of administration. Dosage units will generally contain between from about 10 μg to about 500 mg of an active ingredient. Optimal dosages may be established using routine testing, and procedures that are well known in the art.

Pharmaceutical compositions may be packaged for treating conditions responsive to VR1 modulation (e.g., treatment of exposure to vanilloid ligand, pain, itch, obesity or urinary incontinence). Packaged pharmaceutical compositions may include a container holding a therapeutically effective amount of at least one VR1 modulator as described herein and instructions (e.g., labeling) indicating that the contained composition is to be used for treating a condition responsive to VR1 modulation in the patient.

Methods of Use

VR1 modulators provided herein may be used to alter activity and/or activation of capsaicin receptors in a variety of contexts, both in vitro and in vivo. Within certain aspects, VR1 antagonists may be used to inhibit the binding of vanilloid ligand agonist (such as capsaicin and/or RTX) to capsaicin receptor in vitro or in vivo. In general, such methods comprise the step of contacting a capsaicin receptor with a capsaicin receptor modulatory amount of one or more VR1 modulators provided herein, in the presence of vanilloid ligand in aqueous solution and under conditions otherwise suitable for binding of the ligand to capsaicin receptor. The capsaicin receptor may be present in solution or suspension (e.g., in an isolated membrane or cell preparation), or in a cultured or isolated cell. Within certain embodiments, the capsaicin receptor is expressed by a neuronal cell present in a patient, and the aqueous solution is a body fluid. Preferably, one or more VR1 modulators are administered to an animal in an amount such that the analogue is present in at least one body fluid of the animal at a therapeutically effective concentration that is 1 micromolar or less; preferably 500 nanomolar or less; more preferably 100 nanomolar or less, 50 nanomolar or less, 20 nanomolar or less, or 10 nanomolar or less. For example, such compounds may be administered at a dose that is less than 20 mg/kg body weight, preferably less than 5 mg/kg and, in some instances, less than 1 mg/kg.

Also provided herein are methods for modulating, preferably reducing, the signal-transducing activity (i.e., the calcium conductance) of a cellular capsaicin receptor. Such modulation may be achieved by contacting a capsaicin receptor (either in vitro or in vivo) with a capsaicin receptor modulatory amount of one or more VR1 modulators provided herein under conditions suitable for binding of the modulator(s) to the receptor. The receptor may be present in solution or suspension, in a cultured or isolated cell preparation or in a cell within a patient. For example, the cell may be a neuronal cell that is contacted in vivo in an animal. Alternatively, the cell may be an epithelial cell, such as a urinary bladder epithelial cell (urothelial cell) or an airway epithelial cell that is contacted in vivo in an animal. Modulation of signal tranducing activity may be assessed by detecting an effect on calcium ion conductance (also referred to as calcium mobilization or flux). Modulation of signal transducing activity may alternatively be assessed by detecting an alteration of a symptom (e.g., pain, burning sensation, broncho-constriction, inflammation, cough, hiccup, itch, urinary incontinence or overactive bladder) of a patient being treated with one or more VR1 modulators provided herein.

VR1 modulator(s) provided herein are preferably administered to a patient (e.g., a human) orally or topically, and are present within at least one body fluid of the animal while modulating VR1 signal-transducing activity. Preferred VR1 modulators for use in such methods modulate VR1 signal-transducing activity in vitro at a concentration of 1 nanomolar or less, preferably 100 picomolar or less, more preferably 20 picomolar or less, and in vivo at a concentration of 1 micromolar or less, 500 nanomolar or less, or 100 nanomolar or less in a body fluid such as blood.

The present invention further provides methods for treating conditions responsive to VR1 modulation. Within the context of the present invention, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to VR1 modulation" if it is characterized by inappropriate activity of a capsaicin receptor, regardless of the amount of vanilloid ligand present locally, and/or if modulation of capsaicin receptor activity results in alleviation of the condition or a symptom thereof. Such conditions include, for example, symptoms resulting from exposure to VR1-activating stimuli, pain, respiratory disorders such as asthma and chronic obstructive pulmonary disease, itch, urinary incontinence, overactive bladder, cough, hiccup, and obesity, as described in more detail below. Such conditions may be diagnosed and monitored using criteria that have been established in the art. Patients may include humans, domesticated companion animals and livestock, with dosages as described above.

Treatment regimens may vary depending on the compound used and the particular condition to be treated. However, for treatment of most disorders, a frequency of administration of 4 times daily or less is preferred. In general, a dosage regimen of 2 times daily is more preferred, with once a day dosing particularly preferred. For the treatment of acute pain, a single dose that rapidly reaches effective concentrations is desirable. It will be understood, however, that the specific dose level and treatment regimen for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dose sufficient to provide effective therapy is preferred. Patients may generally be monitored for therapeutic effectiveness using medical or veterinary criteria suitable for the condition being treated or prevented.

Patients experiencing symptoms resulting from exposure to capsaicin receptor-activating stimuli include individuals with burns caused by heat, light, tear gas or acid and those whose mucous membranes are exposed (e.g., via ingestion, inhalation or eye contact) to capsaicin (e.g., from hot peppers or in pepper spray) or a related irritant such as acid, tear gas or air pollutants. The resulting symptoms (which may be treated using VR1 modulators, especially antagonists, provided herein) may include, for example, pain, broncho-constriction and inflammation.

Pain that may be treated using the VR1 modulators provided herein may be chronic or acute and includes, but is not limited to, peripheral nerve-mediated pain (especially neuropathic pain). Compounds provided herein may be used in the treatment of, for example, postmastectomy pain syndrome, stump pain, phantom limb pain, oral neuropathic pain, toothache (dental pain), denture pain, postherpetic neuralgia, diabetic neuropathy, reflex sympathetic dystrophy, trigeminal neuralgia, osteoarthritis, rheumatoid arthritis, fibromyalgia, Guillain-Barre syndrome, meralgia paresthetica, burning-mouth syndrome and/or bilateral peripheral neuropathy. Additional neuropathic pain conditions include causalgia (reflex sympathetic dystrophy—RSD, secondary to injury of a peripheral nerve), neuritis (including, for example, sciatic neuritis, peripheral neuritis, polyneuritis, optic neuritis, postfebrile neuritis, migrating neuritis, segmental neuritis and Gombault's neuritis), neuronitis, neuralgias (e.g., those mentioned above, cervicobrachial neuralgia, cranial neuralgia, geniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia, splenopalatine neuralgia, supraorbital neuralgia and vidian neuralgia), surgery-related pain, musculoskeletal pain, AIDS-related neuropathy, MS-related neuropathy, and spinal cord injury-related pain. Headache, including headaches involving peripheral nerve activity, such as sinus, cluster (i.e., migranous neuralgia) and some tension headaches and migraine, may also be treated as described herein. For example, migraine headaches may be prevented by administration of a compound provided herein as soon as a pre-migrainous aura is experienced by the patient. Further pain conditions that can be treated as described herein include "burning mouth syndrome," labor pains, Charcot's pains, intestinal gas pains, menstrual pain, acute and chronic back pain (e.g., lower back pain), hemorrhoidal pain, dyspeptic pains, angina, nerve root pain, homotopic pain and heterotopic pain—including cancer associated pain (e.g., in patients with bone cancer), pain (and inflammation) associated with venom exposure (e.g., due to snake bite, spider bite, or insect sting) and trauma associated pain (e.g., post-surgical pain, pain from cuts, bruises and broken bones, and burn pain). Additional pain conditions that may be treated as described herein include pain associated with inflammatory bowel disease, irritable bowel syndrome and/or inflammatory bowel disease.

Within certain aspects, VR1 modulators provided herein may be used for the treatment of mechanical pain. As used herein, the term "mechanical pain" refers to pain other than headache pain that is not neuropathic or a result of exposure to heat, cold or external chemical stimuli. Mechanical pain includes physical trauma (other than thermal or chemical burns or other irritating and/or painful exposures to noxious chemicals) such as post-surgical pain and pain from cuts, bruises and broken bones; toothache, denture pain; nerve root pain; osteoartiritis; rheumatoid arthritis; fibromyalgia; meralgia paresthetica; back pain; cancer-associated pain; angina; carpel tunnel syndrome; and pain resulting from bone fracture, labor, hemorrhoids, intestinal gas, dyspepsia, and menstruation.

Itching conditions that may be treated include psoriatic pruritis, itch due to hemodialysis, aguagenic pruritus, and itching associated with vulvar vestibulitis, contact dermatitis, insect bites and skin allergies. Urinary tract conditions that may be treated as described herein include urinary incontinence (including overflow incontinence, urge incontinence and stress incontinence), as well as overactive or unstable bladder conditions (including detrusor hyperflexia of spinal origin and bladder hypersensitivity). In certain such treatment methods, VR1 modulator is administered via a catheter or similar device, resulting in direct injection of VR1 modulator into the bladder. Compounds provided herein may also be used as anti-tussive agents (to prevent, relieve or suppress coughing) and for the treatment of hiccup, and to promote weight loss in an obese patient.

Within other aspects, VR1 modulators provided herein may be used within combination therapy for the treatment of conditions involving inflammatory components. Such conditions include, for example, autoimmune disorders and pathologic autoimmune responses known to have an inflammatory component including, but not limited to, arthritis (especially rheumatoid arthritis), psoriasis, Crohn's disease, lupus erythematosus, irritable bowel syndrome, tissue graft rejection, and hyperacute rejection of transplanted organs. Other such conditions include trauma (e.g., injury to the head or spinal cord), cardio- and cerebo-vascular disease and certain infectious diseases.

Within such combination therapy, a VR1 modulator is administered to a patient along with an anti-inflammatory agent. The VR1 modulator and anti-inflammatory agent may be present in the same pharmaceutical composition, or may be administered separately in either order. Anti-inflammatory agents include, for example, non-steroidal anti-inflammatory drugs (NSAIDs), non-specific and cyclooxygenase-2 (COX-2) specific cyclooxgenase enzyme inhibitors, gold compounds, corticosteroids, methotrexate, tumor necrosis factor (TNF) receptor antagonists, anti-TNF alpha antibodies, anti-C5 antibodies, and interleukin-1 (IL-1) receptor antagonists. Examples of NSAIDs include, but are not limited to ibuprofen (e.g., ADVIL™, MOTRIN™), flurbiprofen (ANSAID™), naproxen or naproxen sodium (e.g., NAPROSYN, ANAPROX, ALEVE™), diclofenac (e.g., CATAFLAM™, VOLTAREN™), combinations of diclofenac sodium and misoprostol (e.g., ARTHROTEC™), sulindac (CLINORIL™), oxaprozin (DAYPRO™), diflunisal (DOLOBID™), piroxicam (FELDENE™), indomethacin (INDOCIN™), etodolac (LODINE™), fenoprofen calcium (NALFON™), ketoprofen (e.g., ORUDIS™, ORUVAIL™), sodium nabumetone (RELAFEN™), sulfasalazine (AZULFIDINE™), tolmetin sodium (TOLECTIN™), and hydroxychloroquine (PLAQUENIL™). A particular class of NSAIDs consists of compounds that inhibit cyclooxygenase (COX) enzymes, such as celecoxib (CELEBREX™) and rofecoxib (VIOXX™). NSAIDs further include salicylates such as acetylsalicylic acid or aspirin, sodium salicylate, choline and magnesium salicylates (TRILISATE™), and salsalate (DISALCID™), as well as corticosteroids such as cortisone (CORTONE™ acetate), dexamethasone (e.g., DECADRON™), methylprednisolone (MEDROL™) prednisolone (PRELONE™), prednisolone sodium phosphate (PEDIAPRED™), and prednisone (e.g., PREDNICEN-M™, DELTASONE™, STERAPRED™).

Suitable dosages for VR1 modulator within such combination therapy are generally as described above. Dosages and methods of administration of anti-inflammatory agents can be found, for example, in the manufacturer's instructions in the *Physician's Desk Reference*. In certain embodiments, the combination administration of a VR1 modulator with an anti-inflammatory agent results in a reduction of the dosage of the anti-inflammatory agent required to produce a therapeutic effect. Thus, preferably, the dosage of anti-inflammatory agent in a combination or combination treatment method of the invention is less than the maximum dose advised by the manufacturer for administration of the anti-inflammatory agent without combination administration of a VR1 antagonist. More preferably this dosage is less than ¾, even more preferably less than ½, and highly preferably, less than ¼ of the maximum dose, while most preferably the dose is less than 10% of the maximum dose advised by the manufacturer for administration of the anti-inflammatory agent(s) when administered without combination administration of a VR1 antagonist. It will be apparent that the dosage amount of VR1 antagonist component of the combination needed to achieve the desired effect may similarly be affected by the dosage amount and potency of the anti-inflammatory agent component of the combination.

In certain preferred embodiments, the combination administration of a VR1 modulator with an anti-inflammatory agent is accomplished by packaging one or more VR1 modulators and one or more anti-inflammatory agents in the same package, either in separate containers within the package or in the same contained as a mixture of one or more VR1 antagonists and one or more anti-inflammatory agents. Preferred mixtures are formulated for oral administration (e.g., as pills, capsules, tablets or the like). In certain embodiments, the package comprises a label bearing indicia indicating that the one or more VR1 modulators and one or more anti-inflammatory agents are to be taken together for the treatment of an inflammatory pain condition. A highly preferred combination is one in which the anti-inflammatory agent(s) include at least one COX-2 specific cyclooxgenase enzyme inhibitor such as valdecoxib (BEXTRA®), lumiracoxib (PREXIGE™), etoricoxib (ARCOXIA®), celecoxib (CELEBREX®) and/or rofecoxib (VIOXX®).

Within further aspects, VR1 modulators provided herein may be used in combination with one or more additional pain relief medications. Certain such medications are also anti-inflammatory agents, and are listed above. Other such medications are narcotic analgesic agents, which typically act at one or more opioid receptor subtypes (e.g., μ, ? and/or d), preferably as agonists or partial agonists. Such agents include opiates, opiate derivatives and opioids, as well as pharmaceutically acceptable salts and hydrates thereof. Specific examples of narcotic analgesics include, within preferred embodiments, alfentanyl, alphaprodine, anileridine, bezitramide, buprenorphine, codeine, diacetyldihydromorphine, diacetylmorphine, dihydrocodeine, diphenoxylate, ethylmorphine, fentanyl, heroin, hydrocodone, hydromorphone, isomethadone, levomethorphan, levorphane, levorphanol, meperidine, metazocine, methadone, methorphan, metopon, morphine, opium extracts, opium fluid extracts, powdered opium, granulated opium, raw opium, tincture of opium, oxycodone, oxymorphone, paregoric, pentazocine, pethidine, phenazocine, piminodine, propoxyphene, racemethorphan, racemorphan, thebaine and pharmaceutically acceptable salts and hydrates of the foregoing agents.

Other examples of narcotic analgesic agents include acetorphine, acetyldihydrocodeine, acetylmethadol, allylprodine, alphracetylmethadol, alphameprodine, alphamethadol, benzethidine, benzylmorphine, betacetylmethadol, betameprodine, betamethadol, betaprodine, butorphanol, clonitazene, codeine methylbromide, codeine-N-oxide, cyprenorphine, desomorphine, dextromoramide, diampromide, diethylthiambutene, dihydromorphine, dimenoxadol, dimepheptanol, dimethylthiamubutene, dioxaphetyl butyrate, dipipanone, drotebanol, ethanol, ethylmethylthiambutene, etonitazene, etorphine, etoxeridine, furethidine, hydromorphinol, hydroxypethidine, ketobemidone, levomoramide, levophenacylmorphan, methyldesorphine, methyldihydromorphine, morpheridine, morphine methylpromide, morphine methylsulfonate, morphine-N-oxide, myrophin, naloxone, nalbuyphine, naltyhexone, nicocodeine, nicomorphine, noracymethadol, norlevorphanol, normethadone, normorphine, norpipanone, pentazocaine, phenadoxone, phenampromide, phenomorphan, phenoperidine, piritramide, pholcodine, proheptazoine, properidine, propiran, racemoramide, thebacon, trimeperidine and the pharmaceutically acceptable salts and hydrates thereof.

Further specific representative analgesic agents include, for example: TALWIN® Nx and DEMEROL® (both available from Sanofi Winthrop Pharmaceuticals; New York, N.Y.); LEVO-DROMORAN®; BUPRENEX® (Reckitt & Coleman Pharmaceuticals, Inc.; Richmond, Va.); MSIR® (Purdue Pharma L. P.; Norwalk, Conn.); DILAUDID® (Knoll Pharmaceutical Co.; Mount Olive, N.J.); SUBLIMAZE®; SUFENTA® (Janssen Pharmaceutica Inc.; Titusville, N.J.); PERCOCET®, NUBAIN® and NUMORPHAN® (all available from Endo Pharmaceuticals Inc.; Chadds Ford, Pa.) HYDROSTAT® IR, MS/S and MS/L (all available from Richwood Pharmaceutical Co. Inc; Florence, Ky.), ORAMORPH® SR and ROXICODONE® (both available from Roxanne Laboratories; Columbus Ohio) and STADOL® (Bristol-Myers Squibb; New York, N.Y.). Still further analgesic agents include CB2-receptor agonists, such as AM1241, and compounds that bind to the a2d subunit, such as Neurontin (Gabapentin) and pregabalin.

Suitable dosages for VR1 modulator within such combination therapy are generally as described above. Dosages and methods of administration of other pain relief medications can be found, for example, in the manufacturer's instructions in the *Physician's Desk Reference*. In certain embodiments, the combination administration of a VR1 modulator with one or more additional pain medications results in a reduction of the dosage of each therapeutic agent required to produce a therapeutic effect (e.g., the dosage or one or both agent may less than ¾, less than ½, less than ¼ or less than 10% of the maximum dose listed above or advised by the manufacturer). In certain preferred embodiments, the combination administration of a VR1 modulator with one or more additional pain relief medications is accomplished by packaging one or more VR1 modulators and one or more additional pain relief medications in the same package, as described above.

Modulators that are VR1 agonists may further be used, for example, in crowd control (as a substitute for tear gas) or personal protection (e.g., in a spray formulation) or as pharmaceutical agents for the treatment of pain, itch, urinary incontinence or overactive bladder via capsaicin receptor desensitization. In general, compounds for use in crowd control or personal protection are formulated and used according to conventional tear gas or pepper spray technology.

Within separate aspects, the present invention provides a variety of non-pharmaceutical in vitro and in vivo uses for the compounds provided herein. For example, such compounds may be labeled and used as probes for the detection and localization of capsaicin receptor (in samples such as cell preparations or tissue sections, preparations or fractions thereof). Compounds may also be used as positive controls in assays for receptor activity, as standards for determining the ability of a candidate agent to bind to capsaicin receptor, or as radiotracers for positron emission tomography (PET) imaging or for single photon emission computerized tomography (SPECT). Such methods can be used to characterize capsaicin receptors in living subjects. For example, a VR1 modulator may be labeled using any of a variety of well known techniques (e.g., radiolabeled with a radionuclide such as tritium, as described herein), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of capsaicin receptor in the sample. Detection assays, including receptor autoradiography (receptor mapping) of capsaicin receptor in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell separation methods. For example, modulators may be linked to the interior surface of a tissue culture plate or other support, for use as affinity ligands for immobilizing and thereby isolating, capsaicin receptors (e.g., isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

The following Examples are offered by way of illustration and not by way of limitation. Unless otherwise specified all reagents and solvent are of standard commercial grade and are used without further purification. Using routine modifications, the starting materials may be varied and additional steps employed to produce other compounds provided herein.

EXAMPLES

The following abbreviations are used herein:

AcCN acetonitrile

AcOH acetic acid d chemical shift

DCM dichloromethane

DMSO dimethylsulfoxide
DME ethylene glycol dimethyl ether
DPPF 1,1'-bis(diphenylphosphino)ferrocene
iPr isopropyl
EtOAc ethyl acetate
$^1$H NMR proton nuclear magnetic resonance
HPLC high pressure liquid chromatography
Hz hertz
LCMS liquid chromatography/mass spectrometry
MS mass spectrometry
(M+1) mass+1
Pd$_2$(dba)$_3$ tris[dibenzylidineacetone]di-palladium
Pd(PPh$_3$)$_4$ tetrakis(triphenylphosphine)palladium (0)
THF tetrahydrofuran
TLC thin layer chromatography
Xantphos 4,5-bis(diphenylphosphino)-9,9-dimethyl-xanthene Example 1

Preparation of [2-Isopropoxymethyl-7-(3-trifluoromethyl-pyridin-2-yl)-quinazolin-4-yl]-(4-trifluoromethyl-phenyl)-amine (Compound 1)

This Example illustrates the preparation of a representative substituted (7-pyridyl-4-phenylamino-quinazolin-2-yl)-methanol analogue.

1. 2-p-tolyl-3-trifluoromethyl-pyridine

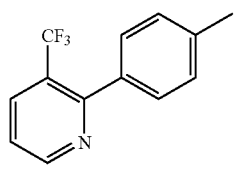

To a de-gassed mixture of 2-chloro-3-(trifluoromethyl)-pyridine (70.1 mmol), p-tolylboronic acid (70.6 mmol), and 2M Na$_2$CO$_3$ (175.0 mmol), in ethylene glycol dimethyl ether (DME; 200 mL) under nitrogen add Pd(PPh$_3$)$_4$ (2.8 mmol). Stir the mixture at 80° C. overnight, concentrate, and extract with EtOAc. Dry over Na$_2$SO$_4$, concentrate under vacuum, and pass through a silica gel pad to give 2-p-tolyl-3-trifluoromethyl-pyridine.

2. 2-(4-methyl-3-nitro-phenyl)-3-(trifluoromethyl)-pyridine

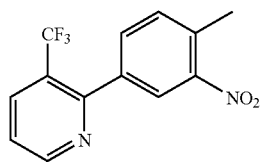

To a solution of 2-p-tolyl-3-trifluoromethyl-pyridine (8.4 mmol) in H$_2$SO$_4$ (6 mL) cautiously add fuming HNO$_3$ (2 ml). Stir the mixture for 60 minutes at room temperature. Pour the mixture onto ice-water (30 mL), extract with EtOAc, neutralize with 1 N NaOH, dry over Na$_2$SO$_4$, and concentrate under vacuum to obtain 2-(4-methyl-3-nitrophenyl)-3-(trifluoromethyl)-pyridine.

3. 2-nitro-4-(3-trifluoromethyl-pyridin-2-yl)-benzoic acid

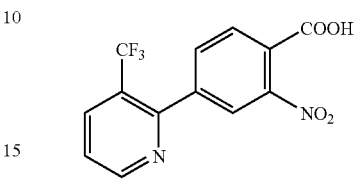

To a solution of 2-(4-methyl-3-nitro-phenyl)-3-(trifluoromethyl)-pyridine (7.1 mmol) in a mixture of pyridine (10 mL) and water (5 ml), add KMnO$_4$ (25.3 mmol) portionwise. Stir the mixture for 4 hours at 110° C., and then add another 25.3 mmol of KMnO$_4$ with 10 ml of water. Stir the mixture at 110° C. over night. Cool to room temperature, and filter through celite pad. Concentrate the filtrate under vacuum, dilute with water, and wash the aqueous solution with EtOAc. Neutralize the aqueous solution with 2 N HCl and collect the precipitate to give 2-nitro-4(3-trifluoromethyl-pyridin-2-yl)-benzoic acid.

4. 2-nitro-4-(3-trifluoromethyl-pyridin-2-yl)-benzamide

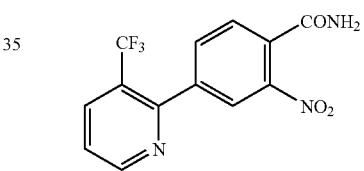

Reflux a mixture of 2-amino-4(3-trifluoromethyl-pyridin-2-yl)-benzoic acid (25 g) with SOCl$_2$ (50 ml) for 4 hours and concentrate. Dissolve the residue in DCM, cool with ice-water bath, pass NH$_3$ gas through the solution for 30 minutes, and stir for 15 minutes at room temperature. Concentrate and wash with water to give 2-nitro-4-(3-trifluoromethyl-pyridin-2-yl)-benzamide.

5. 2-amino-4-(3-trifluoromethyl-pyridin-2-yl)-benzamide

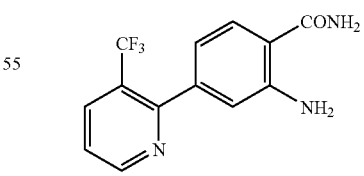

Hydrogenate 2-nitro-4-(3-trifluoromethyl-pyridin-2-yl)-benzamide (1.0 g, 0.0032 mol) with 50 psi of H$_2$ and 100 mg of 10% Pd/C in ethanol. After 16 hours, filter the mixture through celite and concentrate under reduced pressure to give 2-amino-4-(3-trifluoromethyl-pyridin-2-yl)-benzamide as a solid.

6. 2-chloromethyl-7-(3-trifluoromethyl-pyridin-2-yl)-3H-quinazolin-4-one

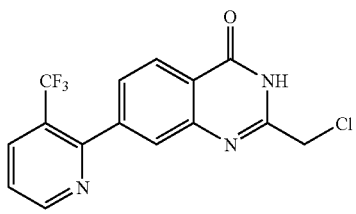

Heat a solution of 2-amino-4-(3-trifluoromethyl-pyridin-2-yl)-benzamide (100 mg, 0.356 mmol) in 2-chloro-1,1,1-trimethoxyethane (bp 138° C.) at 130° C. for 4 hours. Concentrate the mixture under reduced pressure to give 2-chloromethyl-7-(3-trifluoromethyl-pyridin-2-yl)-3H-quinazolin-4-one as an oil which crystallizes on standing.

7. 4-chloro-2-chloromethyl-7-(3-trifluoromethyl-pyridin-2-yl)-quinazoline

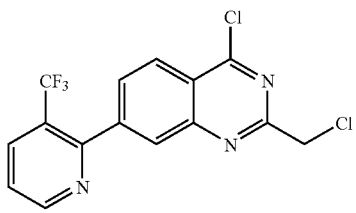

Reflux a mixture of 2-chloromethyl-7-(3-trifluoromethyl-pyridin-2-yl)-3H-quinazolin-4-one (obtained from the reaction above) and POCl$_3$ for 16 hours. Cool the mixture and concentrate under reduced pressure. Partition the residue between EtOAc and saturated NaHCO$_3$ solution. Wash the EtOAc portion with additional NaHCO$_3$ and then dry (Na$_2$SO$_4$) and concentrate under reduced pressure. Filter the brown residue through 2 inches of silica gel (1:1 EtOAc/hexanes eluent) and concentrate under reduced pressure to give 4-chloro-2-chloromethyl-7-(3-trifluoromethyl-pyridin-2-yl)-quinazoline.

8. [2-chloromethyl-7-(3-trifluoromethyl-pyridin-2-yl)-quinazolin-4-yl]-(4-trifluoro methyl-phenyl)-amine

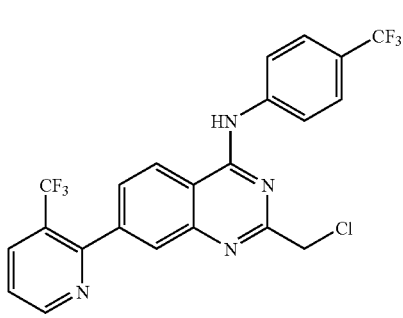

Heat a mixture of 4-chloro-2-chloromethyl-7-(3-trifluoromethyl-pyridin-2-yl)-quinazoline (42 mg, 0.117 mmol) and 4-trifluoromethyl-aniline (19 mg, 0.117 mmol) in isopropyl alcohol (1 mL) at 75° C. for 4 hours. Cool the mixture and wash the precipitate with isopropyl alcohol followed by ether to give [2-chloromethyl-7-(3-trifluoromethyl-pyridin-2-yl)-quinazolin-4-yl]-(4-trifluoromethyl-phenyl)-amine as the mono-HCl salt.

9. [2-Isopropoxymethyl-7-(3-trifluoromethyl-pyridin-2-yl)-quinazolin-4-yl]-(4-trifluoromethyl-phenyl)-amine

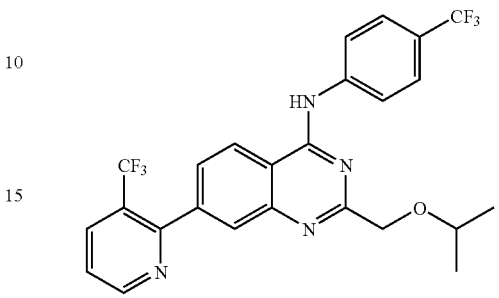

To a suspension of [2-chloromethyl-7-(3-trifluoromethyl-pyridin-2-yl)-quinazolin-4-yl]-(4-trifluoromethyl-phenyl)-amine hydrochloride (1.9 g, 0.0037 mol) in dry isopropanol (100 mL), add 20 equivalents of NaO-iPr (prepared from Na and isopropanol). Stir the pale yellow mixture at 60° C. for 5 hours, cool and evaporate the solvent under reduced pressure. Partition the residue between ethyl acetate and water and wash the organic layer with water (1×). Dry the organic layer (Na$_2$SO$_4$) and concentrate to give [2-isopropoxymethyl-7-(3-trifluoromethyl-pyridin-2-yl)-quinazolin-4-yl]-(4-trifluoromethyl-phenyl)-amine as a foam. IC$_{50}$ in standard assay of capsaicin receptor activity is less than 10 nanomolar.

Example 2

Preparation of Additional Representative Compounds

This Example illustrates the preparation of additional representative substituted (7-pyridyl-4-phenylamino-quinazolin-2-yl)-methanol analogues.

A. [7-(3-Chloro-pyridin-2-yl)-2-methoxymethyl-pyrido[2,3-d]pyrimidin-4-yl]-(4-trifluoromethyl-phenyl)-amine (Compound 2)

1. 2-Acetyl-3-chloropyridine

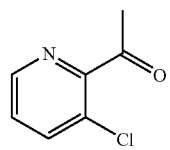

Dissolve 3-chloro-2-cyanopyridine (10.0 g, 0.072 mol, Chem. Pharm. Bull. (1985) 33:565-571) in anhydrous THF (200 mL) under N$_2$ atmosphere and cool in an ice bath. Add drop wise 3.0 M MeMgI in diethyl ether (48 ml, 0.14 mol) to the reaction mixture and stir in an ice bath for 2 hours. Pour the reaction mixture over ice cold water, acidify the mixture with 2.0 N aq. HCl to pH 2 to 3. Extract the reaction mixture with EtOAc (3×100 mL) and dry over anhydrous MgSO$_4$. Filter, concentrate under vacuum and then filter through a pad of silica gel using 20% ethyl acetate/hexane as eluent. Removal of solvent under reduced pressure gives pure 2-acetyl-3-chloropyridine as oil.

2. 1-(3-Chloro-pyridin-2-yl)-3-dimethylaminopropenone

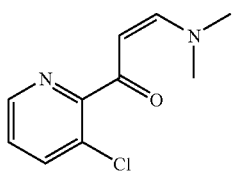

Heat 2-acetyl-3-chloropyridine (0.77 g, 5.0 mmol) with N,N-dimethylformamide dimetylacetal (3.0 g) at 105° C. for 20 hours. Concentrate under reduced pressure to give 1-(3-chloro-pyridin-2-yl)-3-dimethylaminopropenone as oil.

3. 2-Amino-4-(3-chloro-pyridin-2-yl)-benzonitrile

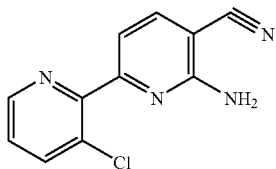

Heat a solution of 1-(3-Chloro-pyridin-2-yl)-3-dimethylaminopropenone (1.05 g, 5 mmol), 3-amino-3-methoxyacrylonitrile hydrochloride (1.35 g, 10 mmol) and ammonium acetate (2.2 g, 15.0 mmol) in ethanol (25 mL) at reflux for 20 hours. Cool the mixture and concentrate under reduced pressure to give dark oil. Dissolve the residue in EtOAc/water (100 mL). Extract the aqueous solution with EtOAc, wash the EtOAc with brine, dry (MgSO$_4$) and concentrate under reduced pressure to give 2-amino-4-(3-chloro-pyridin-2-yl)-benzonitrile as a brown solid.

4. 6-Amino-3'-chloro-[2,2']bipyridinyl-5-carboxylic acid amide

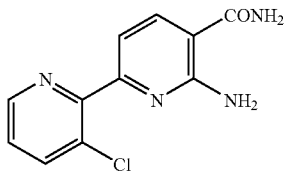

Cool concentrated sulfuric acid (10 mL) in an ice bath under nitrogen atmosphere. Add in portions 2-amino-4-(3-chloro-pyridin-2-yl)-benzonitrile (1.0 g, 4.3 mmol) over a period of 15 minutes. Stir at room temperature overnight. Pour the reaction mixture over ice, adjust the pH to 10 using 10 N aq. NaOH, filter the solid, wash the solid with water and dry under vacuum to give 6-amino-3'-chloro-[2,2']bipyridinyl-5-carboxylic acid amide as a yellow solid.

5. 7-(3-Chloro-pyridin-2-yl)-2-methoxymethyl-3H-pyrido[2,3-d]pyrimidin-4-one

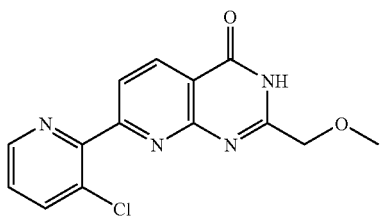

Dissolve 6-amino-3'-chloro-[2,2']bipyridinyl-5-carboxylic acid amide (0.5 g, 2.02 mmol) in anhydrous THF (10 mL) under N$_2$ atmosphere. Add drop wise pyridine (0.36 g, 4.04 mmol) and methoxyacetyl chloride (0.48 g, 4.04 mmol) to the reaction mixture and stir at room temperature overnight. Add 10% aq. NaOH (10 mL) and reflux for 4 hours. Concentrate in vacuum, adjust the pH to 6.0 using AcOH, collect the solid by filtration and dry under vacuum to give 7-(3-chloro-pyridin-2-yl)-2-methoxymethyl-3H-pyrido[2,3-d]pyrimidin-4-one as a white solid.

6. 4-Chloro-7-(3-chloro-pyridin-2-yl)-2-methoxymethyl-pyrido[2,3-d]pyrimidine

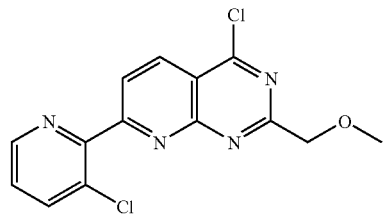

Reflux a mixture of 7-(3-chloro-pyridin-2-yl)-2-methoxymethyl-3H-pyrido[2,3-d]pyrimidin-4-one (0.25 g), 2,6-lutidine (0.44 g), and POCl$_3$ (0.51 g) in CHCl$_3$ (5 mL) for 20 hours. Cool the mixture and concentrate under reduced pressure. Partition the residue between EtOAc and saturated NaHCO$_3$ solution. Wash the EtOAc portion with additional NaHCO$_3$ and then dry (Na$_2$SO$_4$) and concentrate under reduced pressure. Filter the brown residue through 2 inches of silica gel (1:1 EtOAc/hexanes eluent) and concentrate under reduced pressure to give 4-chloro-7-(3-chloro-pyridin-2-yl)-2-methoxymethyl-pyrido[2,3-d]pyrimidine.

7. [7-(3-Chloro-pyridin-2-yl)-2-methoxymethyl-pyrido[2,3-d]pyrimidin-4-yl]-(4-trifluoromethyl-phenyl)-amine

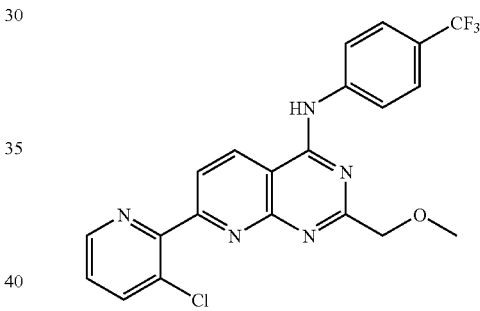

Heat a mixture of 4-chloro-7-(3-chloro-pyridin-2-yl)-2-methoxymethyl-pyrido[2,3-d]pyrimidine (0.1 mmol) and 4-trifluoromethyl-aniline (16.1 mg, 0.1 mmol) in AcCN (1 mL) at 80° C. for 24 hours. Cool the mixture and wash the precipitate with ether to give the title product as the mono-HCl salt. IC$_{50}$ in standard assay of capsaicin receptor activity is less than 10 nanomolar.

B. [2-Methoxymethyl-7-(3-methylpyridin-2-yl)-quinazolin-4-yl)-(4-trifluoromethylphenyl)-amine (Compound 3)

1. 7-bromo-2-methoxymethylquinazolin-4-yl)-(4-trifluoromethylphenyl)-amine

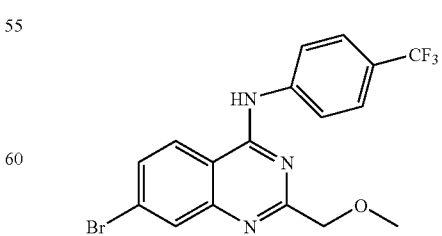

Heat a mixture of 7-bromo-2-chloromethylquinazolin-4-yl)-(4-trifluoromethylphenyl)-amine (from Example C, 200 mg, 0.48 mmol), 4.4M sodium methoxide in methanol (2.4 mL), and methanol (1 mL) to 60° C. for 4 hours. Cool to room temperature and evaporate the mixture. Dilute with EtOAc (10 mL) and wash 2× with water (10 mL each). Dry the organic layer (Na₂SO₄) and evaporate. Purify by preparative TLC (3:1 hexanes:EtOAc) to obtain 2-methoxymethyl-7-pyridin-4-yl-quinazolin-4-yl)-(4-trifluoromethylphenyl)-amine (225 mg) as a yellow solid.

2. [2-Methoxymethyl-7-(3-methylpyridin-2-yl)-quinazolin-4-yl)-(4-trifluoromethyl phenyl)-amine

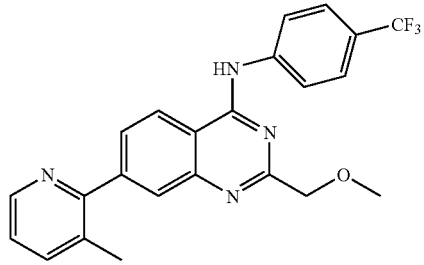

Heat a mixture of 2-methoxymethyl-7-pyridin-4-yl-quinazolin-4-yl)-(4-trifluoromethylphenyl)-amine (100 mg, 0.243 mmol), 3-methyl-2-pyridylzinc bromide (1 mL of a 0.5M THF solution), tetrakis(triphenylphosphinepalladium (0) (50 mg, 0.043 mmol) in 1,2-dimethoxymethane (5 mL) for 3 hours at 80° C. under nitrogen. Cool to room temperature and dilute with EtOAc (10 mL). Wash with water (2×10 mL) and dry the organic layer (Na₂SO₄) and evaporate. Purify by preparative TLC to obtain [2-methoxymethyl-7-(3-methylpyridin-2-yl)-quinazolin-4-yl)-(4-trifluoromethylphenyl)-amine (38 mg) as an off-white solid. IC₅₀ in standard assay of capsaicin receptor activity is less than 10 nanomolar.

C. [2-Isobutoxymethyl-7-(3-trifluoromethyl-pyridin-2-yl)-pyrido[2,3-d]pyrimidin-4-yl]-(5-trifluoromethyl-pyridin-2-yl)-amine 1. 2-Cyano-3-trifluoromethylpyridine

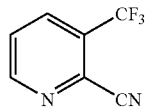

Dissolve 2-chloro-3-trifluoromethylpyridine (36.2 g, 0.2 moles) in DMF (350 mL) at room temperature. Add water (3.5 mL) and zinc cyanide (14 g, 0.12 moles) to the reaction mixture and degas with nitrogen for 15 minutes. Add catalyst Pd₂(dba)₃ (5.5 g, 3 mol %) and ligand DPPF (6.5 g, 6 mol %) to the mixture and then heat at 120° C. with stirring for 1 hour. Cool the reaction mixture in an ice bath and then add saturated ammonium chloride (200 mL), 28% ammonium hydroxide (50 mL) and water (50 mL). Stir the resulting reaction mixture in the ice bath for 1 hour and then dilute it EtOAc (300 mL). Separate the organic layer, extract the aqueous layer with EtOAc (3×300 mL), wash the combined organic layers with brine (2×200 mL) and dry (MgSO₄). Filter the dried extract and concentrate under vacuum to afford crude product as dark brown oil. Purify the crude product by vacuum distillation to afford pure product as colorless oil.

2. 2-Acetyl-3-3-trifluoromethylpyridine

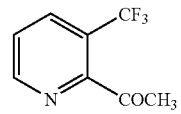

Dissolve 2-cyano-3-trifluoromethylpyridine (30.0 g, 0.174 moles) in anhydrous THF (200 mL) under N₂ atmosphere and cool in an ice bath. Add drop wise 3.0 M MeMgI in diethyl ether (120 ml, 0.348 mol) to the reaction mixture and stir in an ice bath for 30 minutes. Pour the reaction mixture over ice cold water, acidify the mixture with 2.0 N aq. HCl to pH 2 to 3. Extract the reaction mixture with EtOAc (3×300 mL) and dry over anhydrous MgSO₄. Filter, concentrate under vacuum to afford crude product. Purify the crude product by vacuum distillation to afford desired 2-acetyl-3-trifluoromethylpyridine as colorless oil.

3. 3-Dimethylamino-1-(3-trifluoromethyl-pyridin-2-yl)-propenone

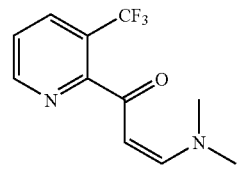

Heat 2-acetyl-3-trifluoromethylpyridine (27 g, 0.143 moles) with N,N-dimethylformamide dimetylacetal (40.0 g) at 105° C. for 4 hours. Concentrate under reduced pressure to give 3-dimethylamino-1-(3-trifluoromethyl-pyridin-2-yl)-propenone.

4. 6-Amino-3'-trifluoromethyl-[2 2']bipyridinyl-5-carbonitrile

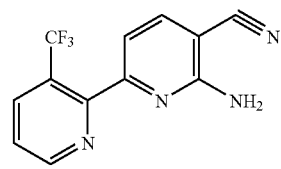

Heat a solution of 3-dimethylamino-1-(3-trifluoromethyl-pyridin-2-yl)-propenone (34.9 g, 0.143 moles), 3-amino-3-methoxy-acrylonitrile hydrochloride (38.5 g, 0.286 moles) and ammonium acetate (55 g, 0.715 moles) in ethanol (400 mL) at reflux for 7 hours. Cool the mixture and concentrate under reduced pressure to give dark oil. Dissolve the residue in EtOAc/water (1000 mL). Extract the aqueous solution with EtOAc (3×300 mL), wash the EtOAc with brine, dry (MgSO₄) and concentrate under reduced pressure to give 6-amino-3'-trifluoromethyl[2,2']bipyridinyl-5-carbonitrile as a brick colored solid.

5. 6-Amino-3'-trifluoromethyl-[2,2']bipyridinyl-5-carboxylic acid amide

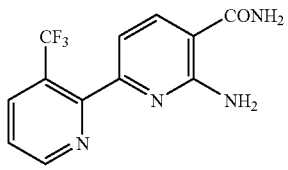

Cool concentrated sulfuric acid (120 mL) in an ice bath under nitrogen atmosphere. Add in portions 6-amino-3'-trifluoromethyl[2,2']bipyridinyl-5-carbonitrile (19.8 g) over a period of 15 minutes. Stir at room temperature 48 hours. Pour the reaction mixture over ice, adjust the pH to 10 using 10 N aqueous NaOH, filter the solid, wash the solid with water and dry under vacuum to give 6-amino-3'-trifluoromethyl-[2,2']bipyridinyl-5-carboxylic acid amide as a light pink solid.

6. 2-Isobutoxymethyl-7-(3-trifluoromethyl-pyridin-2-yl)-3H-pyrido[2,3-d]pyrimidin-4-one

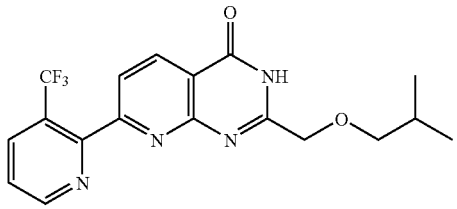

Dissolve 6-amino-3'-trifluoromethyl-[2,2']bipyridinyl-5-carboxylic acid amide (0.5 g, 1.75 mmol) in anhydrous THF (25 mL) under $N_2$ atmosphere. Add dropwise pyridine (0.325 mL, 4.0 mmol) and isobutoxyacetyl chloride (0.2 mL, 4.04 mmol) to the reaction mixture and stir at room temperature overnight. Add 10% aq. NaOH (10 mL) and stir at 50° C. for 4 hours. Concentrate in vacuum, adjust the pH to 6.0 using AcOH, collect the solid by filtration and purify by column chromatography to give 2-isobutoxymethyl-7-(3-trifluoromethyl-pyridin-2-yl)-3H-pyrido[2,3-d]pyrimidin-4-one as a white solid.

7. 4-Chloro-2-isobutoxymethyl-7-(3-trifluoromethyl-pyridin-2-yl)-pyrido[2,3-d]pyrimidine

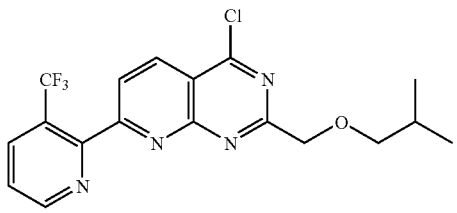

Reflux a mixture of 2-isobutoxymethyl-7-(3-trifluoromethyl-pyridin-2-yl)-3H-pyrido[2,3-d]pyrimidin-4-one (0.510 g, 1.35 mmol), 2,6-lutidine (0.62 mL), and $POCl_3$ (0.50 mL) in $CHCl_3$ (10 mL) for 16 hours. Cool the mixture and concentrate under reduced pressure. Partition the residue between EtOAc and saturated $NaHCO_3$ solution. Wash the EtOAc portion with additional $NaHCO_3$ and then dry ($Na_2SO_4$) and concentrate under reduced pressure. Filter the brown residue through 2 inches of silica gel (1:1 EtOAc/hexanes eluent) and concentrate under reduced pressure to give 4-chloro-2-isobutoxymethyl-7-(3-trifluoromethyl-pyridin-2-yl)-pyrido[2,3-d]pyrimidine as yellow viscous oil.

8. [2-Isobutoxymethyl-7-(3-trifluoromethyl-pyridin-2-yl)-pyrido[2,3-d]pyrimidin-4-yl]-(5-trifluoromethyl-pyridin-2-yl)-amine

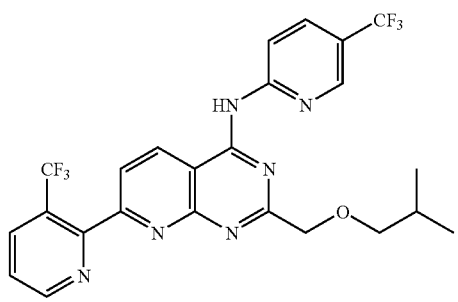

Heat a mixture of 4-chloro-2-isobutoxymethyl-7-(3-trifluoromethyl-pyridin-2-yl)-pyrido[2,3-d]pyrimidine (79.2 mg, 0.2 mmol), 2-amino-5-trifluoromethylpyridine hydrochloride (39.6 mg, 0.2 mmol), xantphos (11.6 mg, 0.1 mmol), $Pd_2(dba)_3$ (18.3 mg, 0.1 mmol) and $Cs_2CO_3$ (130 mg, 0.4 mmol) in dioxane (2.0 mL) at 100° C. for 20 hours. Cool the mixture, concentrate under vacuum, dilute with water (5.0 mL), extract with EtOAc (3×3 mL) and dry with $MgSO_4$. Filter the dried extract and concentrate under vacuum to afford crude product. Purify by flash column chromatography to afford title compound as a yellow solid. $^1H$ NMR (400 MHZ, DMSO-$D_6$) d 0.88 (6H, d, J=1.7), 1.89 (1H, m), 3.37 (2H, d, J=1.6), 4.67 (2H, s), 7.79 (1H, m), 7.96(1H, d, J=2.1), 8.19 (1H, d, J=1.7), 8.42 (1H, d, J=2.0), 8.82(2H, m), 8.98(1H, d, J=1.1), 9.34 (1H, d, J=2.1). MS=523.2 (M+H). $IC_{50}$ in standard assay of capsaicin receptor activity is less than 10 nanomolar.

D. [2-Methoxymethyl-7-(3-trifluoromethyl-pyridin-2-yl)-pyrido[2,3-d]pyrimidin-4-yl]-(5-trifluoromethyl-pyridin-2-yl)-amine 1. 2-Methoxymethyl-7-(3-trifluoromethyl-pyridin-2-yl)-3H-pyrido[2,3-d]pyrimidin-4-one

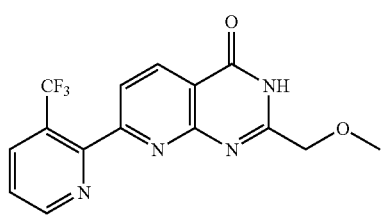

Dissolve 6-amino-3'-trifluoromethyl-[2,2']bipyridinyl-5-carboxylic acid amide (0.564 g, 2.0 mmol) in anhydrous THF (10 mL) under $N_2$ atmosphere. Add dropwise pyridine (0.325 mL, 4.0 mmol) and methoxyacetyl chloride (0.365 mL, 4.0 mmol) to the reaction mixture and stir at room temperature overnight. Add 10% aq. NaOH (10 mL) and stir at 50° C. for 3 hours. Concentrate in vacuum, adjust the pH to 6.0 using AcOH, collect the solid by filtration and purify by column chromatography to give 2-methoxymethyl-7-(3-trifluoromethyl-pyridin-2-yl)-3H-pyrido[2,3-d]pyrimidin-4-one as a white solid.

2. 4-Chloro-2-methoxymethyl-7-(3-trifluoromethyl-pyridin-2-yl)-pyrido[2,3-d]pyrimidine

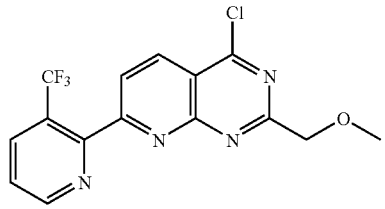

Reflux a mixture of 2-methoxymethyl-7-(3-trifluoromethyl-pyridin-2-yl)-3H-pyrido[2,3-d]pyrimidin-4-one (0.500 g, 1.49 mmol), 2,6-lutidine (0.69 mL), and POCl₃ (0.555 mL) in CHCl₃ (10 mL) for 5 hours. Cool the mixture and concentrate under reduced pressure. Partition the residue between EtOAc and saturated NaHCO₃ solution. Wash the EtOAc portion with additional NaHCO₃ and then dry (MgSO₄) and concentrate under reduced pressure. Purified the crude by flash column chromatography on a silica gel (EtOAc eluent) and concentrate under reduced pressure to give 4-chloro-2-methoxymethyl-7-(3-trifluoromethyl-pyridin-2-yl)-pyrido[2,3-d]pyrimidine as a white solid.

3. [2-Methoxymethyl-7-(3-trifluoromethyl-pyridin-2-yl)-pyrido[2,3-d]pyrimidin-4-yl]-(5-trifluoromethyl-pyridin-2-yl)-amine

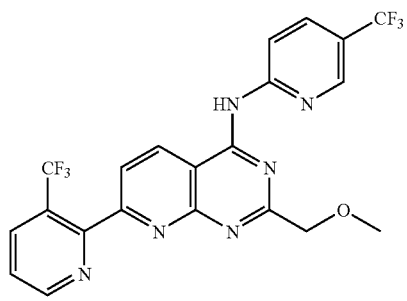

Heat a mixture of 4-chloro-2-methoxymethyl-7-(3-trifluoromethyl-pyridin-2-yl)-pyrido[2,3-d]pyrimidine (115 mg, 0.3 mmol), 2-amino-5-trifluoromethylpyridine hydrochloride (60 mg, 0.3 mmol), xantphos (17.5 mg, 0.03 mmol), Pd₂(dba)₃ (27.3 mg, 0.03 mmol)and Cs₂CO₃ (195 mg, 0.6 mmol) in dioxane (3.0 mL) at 100° C. for 20 hours. Cool the mixture, concentrate under vacuum, dilute with water (5.0 mL), extract with EtOAc (3×3 mL) and dry with MgSO₄. Filter the dried extract and concentrate under vacuum to afford crude product. Purify by flash column chromatography to afford title compound as a yellow solid. ¹H NMR (400 MHZ, DMSO-D₆) d 3.64 (3H, s), 4.63 (2H, s), 7.41 (1H, d, J=2.1), 7.52 (1H, m), 7.81 (1H, d, J=2.1), 7.92(1H, d J=2.0), 8.15 (1H, d, J=2.0), 8.68 (1H, s), 8.88(1H, d, J=1.2), 9.02 (1H, d, J=2.2). MS =481.2 (M+H). IC₅₀ in standard assay of capsaicin receptor activity is less than 10 nanomolar.

Example 3

Representative Substituted (7-Pyridyl-4-Phenylamino-Quinazolin-2-yl)-Methanol Analogues Using routine modifications, the starting materials may be varied and additional steps employed to produce other compounds provided herein. Compounds listed in Table I were prepared using such methods. Mass spectroscopy data in the column labeled "MS" is Electrospray MS, obtained in positive ion mode with a 15V or 30V cone voltage, using a Micromass Time-of-Flight LCT, equipped with a Waters 600 pump, Waters 996 photodiode array detector, Gilson 215 autosampler, and a Gilson 841 microinjector. MassLynx (Advanced Chemistry Development, Inc; Toronto, Canada) version 4.0 software was used for data collection and analysis. Sample volume of 1 microliter was injected onto a 50×4.6 mm Chromolith SpeedROD C18 column, and eluted using a 2-phase linear gradient at 6 ml/min flow rate. Sample was detected using total absorbance count over the 220-340 nm UV range. The elution conditions were: Mobile Phase A-95/5/0.05 Water/Methanol/TFA; Mobile Phase B-5/95/0.025 Water/Methanol/TFA.

| Gradient: | Time(min) | % B |
|---|---|---|
| | 0 | 10 |
| | 0.5 | 100 |
| | 1.2 | 100 |
| | 1.21 | 10 |

The total run time was 2 minutes inject to inject.

For all of the compounds in Table I, the IC₅₀ as determined according to the method recited in Example 6 is 100 nanomolar or less; nearly all have an IC₅₀ below 10 nM; and most have an IC₅₀ below 1 nM.

TABLE I

Representative Substituted (7-Pyridyl-4-Phenylamino-Quinazolin-2-yl)-Methanol Analogues

| Compound | | Name | MS(M + 1)/¹H NMR |
|---|---|---|---|
| 4. | (structure) | (4-Chloro-phenyl)-[2-isobutoxymethyl-7-(3-trifluoromethyl-pyridin-2-yl)-pyrido[2,3-d]pyrimidin-4-yl]-amine | MS 488.2 |

TABLE I-continued

Representative Substituted (7-Pyridyl-4-Phenylamino-Quinazolin-2-yl)-Methanol Analogues

| | Compound | Name | MS(M + 1)/$^1$H NMR |
|---|---|---|---|
| 5. | | (4-Chloro-phenyl)-[2-methoxymethyl-7-(3-trifluoromethyl-pyridin-2-yl)-pyrido[2,3-d]pyrimidin-4-yl]-amine | MS 446.1; $^1$H NMR(DMSO-D6): δ 3.43(3H, s), 4.63(2H, s), 7.55(2H, d, J=2.2), 7.84 (1H, m), 7.87(1H, m), 8.14 (1H, d, J=2.2), 8.46(1H, d, J=1.9), 9.02(1H, d, J=1.2), 9.63 (1H, d, J=2.2), 12.0(1H, bs). |
| 6. | | (4-Chloro-phenyl)-[7-(3-chloro-pyridin-2-yl)-2-isobutoxymethyl-pyrido[2,3-d]pyrimidin-4-yl]-amine | MS 454.2 |
| 7. | | (4-Cyclopropyl-phenyl)-[2-methoxymethyl-7-(3-trifluoromethyl-pyridin-2-yl)-quinazolin-4-yl]-amine | MS 451.4 |
| 8. | | (4-Difluoromethyl-phenyl)-[2-ethoxymethyl-7-(3-trifluoromethyl-pyridin-2-yl)-pyrido[2,3-d]pyrimidin-4-yl]-amine | MS 476.3 |

TABLE I-continued

Representative Substituted (7-Pyridyl-4-Phenylamino-Quinazolin-2-yl)-Methanol Analogues

| Compound | Name | MS(M + 1)/$^1$H NMR |
|---|---|---|
| 9. | (4-Difluoromethyl-phenyl)-[2-isobutoxymethyl-7-(3-trifluoromethyl-pyridin-2-yl)-pyridol[2,3-d]pyrimidin-4-yl]-amine | MS 504.4 |
| 10. | (4-Difluoromethyl-phenyl)-[2-methoxymethyl-7-(3-trifluoromethyl-pyridin-2-yl)-pyrido[2,3-d]pyrimidin-4-yl]-amine | MS 462.3 |
| 11. | (4-Fluoro-phenyl)-[2-isobutoxymethyl-7-(3-trifluoromethyl-pyridin-2-yl)-pyrido[2,3-d]pyrimidin-4-yl]-amine | MS 472.2 |
| 12. | (4-Isopropyl-phenyl)-[2-(tetrahydro-pyran-4-yloxymethyl)-7-(3-trifluoromethyl-pyridin-2-yl)-quinazolin-4-yl]-amine | MS 523.5 |

TABLE I-continued

Representative Substituted (7-Pyridyl-4-Phenylamino-Quinazolin-2-yl)-Methanol Analogues

| | Compound | Name | MS(M + 1)/¹H NMR |
|---|---|---|---|
| 13. | | (4-Isopropyl-phenyl)-[2-methoxymethyl-7-(3-methyl-pyridin-2-yl)-pyrido[2,3-d]pyrimidin-4-yl]-amine | MS 400.3 |
| 14. | | (4-Isopropyl-phenyl)-[2-methoxymethyl-7-(3-methyl-pyridin-2-yl)-quinazolin-4yl]-amine | MS 399.3 |
| 15. | | (4-Isopropyl-phenyl)-[2-methoxymethyl-7-(3-trifluoromethyl-pyridin-2-yl)-qunazolin-4-yl]-amine | MS 453.4 |
| 16. | | (4-Isopropyl-phenyl)-[2-methoxymethyl-7-(3-trifluoromethyl-pyridin-2-yl)-pyrido[2,3-d]pyrimidin-4-yl]-amine | |

TABLE I-continued

Representative Substituted (7-Pyridyl-4-Phenylamino-Quinazolin-2-yl)-Methanol Analogues

| | Compound | Name | MS(M + 1)/$^1$H NMR |
|---|---|---|---|
| 17. | | (4-Isopropyl-phenyl)-[7-(3-methyl-pyridin-2-yl)-2-(tetrahydro-pyran-4-yloxymethyl)-quinazolin-4-yl]-amine | MS 469.5 |
| 18. | | (4-sec-Butyl-phenyl)-[2-methoxymethyl-7-(3-methyl-pyridin-2-yl)-pyrido[2,3-d]pyrimidin-4-yl]-amine | MS 414.3 |
| 19. | | (4-sec-Butyl-phenyl)-[2-methoxymethyl-7-(3-trifluoromethyl-pyridin-2-yl)-pyrido2,3-d]pyrimidin-4-yl]-amine | |
| 20. | | (4-sec-Butyl-phenyl)-[7-(3-chloro-pyridin-2-yl)-2-(2-methoxy-ethoxymethyl)-pyrido[2,3-d]pyrimidin-4-yl]-amine | MS 478.4 |

TABLE I-continued

Representative Substituted (7-Pyridyl-4-Phenylamino-Quinazolin-2-yl)-Methanol Analogues

| | Compound | Name | MS(M + 1)/¹H NMR |
|---|---|---|---|
| 21. | 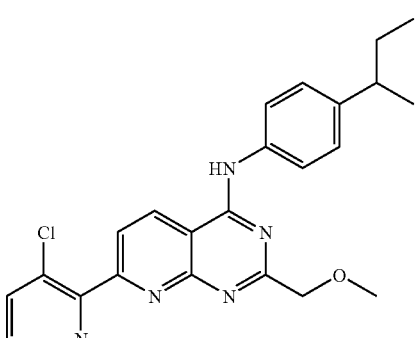 | (4-sec-Butyl-phenyl)-[7-(3-chloro-pyridin-2-yl)-2-methoxymethyl-pyrido[2,3-d]pyrimidin-4-yl]-amine | MS 434.2 |
| 22. | 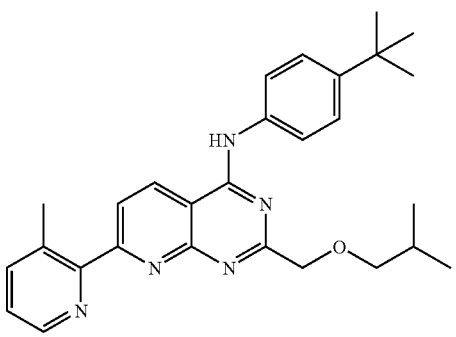 | (4-tert-Butyl-phenyl)-[2-isobutoxymethyl-7-(3-methyl-pyridin-2-yl)-pyrido[2,3-d]pyrimidin-4-yl]-amine | |
| 23. | 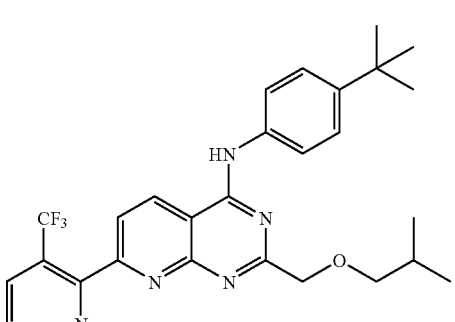 | (4-tert-Butyl-phenyl)-[2-isobutoxymethyl-7-(3-trifluoromethyl-pyridin-2-yl)-pyrido[2,3-d]pyrimidin-4-yl]-amine | MS 510.4 |
| 24. | 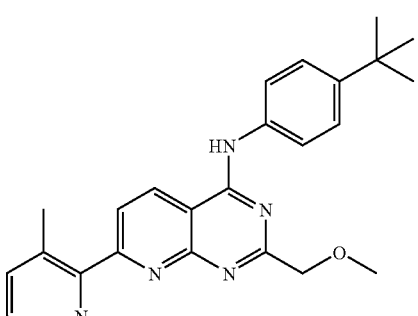 | (4-tert-Butyl-phenyl)-[2-methoxymethyl-7-(3-methyl-pyridin-2-yl)-pyrido[2,3-d]pyrimidin-4-yl]-amine | MS 414.4 |

TABLE I-continued

Representative Substituted (7-Pyridyl-4-Phenylamino-Quinazolin-2-yl)-Methanol Analogues

| | Compound | Name | MS(M + 1)/$^1$H NMR |
|---|---|---|---|
| 25. | | (4-tert-Butyl-phenyl)-[2-methoxymethyl-7-(3-trifluoromethyl-pyridin-2-yl)-quinazolin-4-yl]-amine | MS 467.4 |
| 26. | | (4-tert-Butyl-phenyl)-[2-methoxymethyl-7-(3-trifluoromethyl-pyridin-2-yl)-pyrido[2,3-d]pyrimidin-4-yl]-amine | |
| 27. | | (4-tert-Butyl-phenyl)-[7-(3-chloro-pyridin-2-yl)-2-(2-methoxy-ethoxymethyl)pyrido[2,3-d]pyrimidin-4-yl]-amine | |
| 28. | | (4-tert-Butyl-phenyl)-[7-(3-chloro-pyridin-2-yl)-2-ethoxymethyl-pyrido[2,3-d]pyrimidin-4-yl]-amine | |

TABLE I-continued

Representative Substituted (7-Pyridyl-4-Phenylamino-Quinazolin-2-yl)-Methanol Analogues

| | Compound | Name | MS(M + 1)/$^1$H NMR |
|---|---|---|---|
| 29. | | (4-tert-Butyl-phenyl)-[7-(3-chloro-pyridin-2-yl)-2-ethoxymethyl-quinazolin-4-yl]-amine | MS 447.4 |
| 30. | | (4-tert-Butyl-phenyl)-[7-(3-chloro-pyridin-2-yl)-2-methoxymethyl-pyrido[2,3-d]pyrimidin-4-yl]-amine | MS 434.1 |
| 31. | | (4-tert-Butyl-phenyl)-[7-(3-chloro-pyridin-2-yl)-2-methoxymethyl-quinazolin 4-yl]-amine | MS 433.3 |
| 32. | | (6-tert-Butyl-pyridin-3-yl)-[2-isobutoxymethyl-7-(3-methyl-pyridin-2-yl)-pyrido[2,3-d]pyrimidin-4-yl]-amine | MS 457.3 |

TABLE I-continued

Representative Substituted (7-Pyridyl-4-Phenylamino-Quinazolin-2-yl)-Methanol Analogues

| | Compound | Name | MS(M + 1)/$^1$H NMR |
|---|---|---|---|
| 33. | 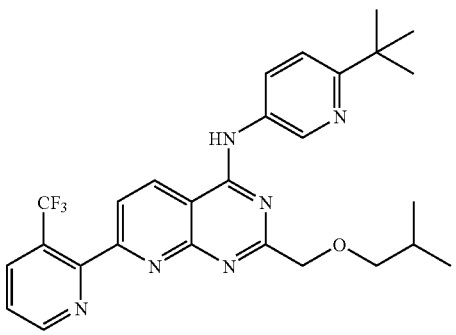 | (6-tert-Butyl-pyridin-3-yl)-[2-isobutoxymethyl-7-(3-trifluoromethy[pyridin-2-yl)-pyrido[2,3-d]pyrimidin-4-yl]-amine | MS 511.3 |
| 34. | 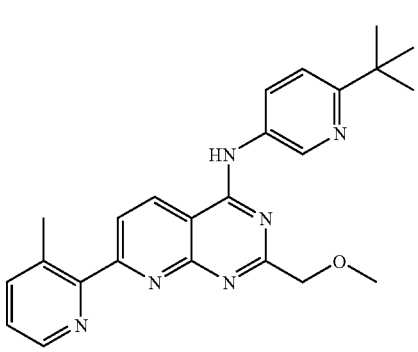 | (6-tert-Butyl-pyridin-3-yl)-[2-methoxymethyl-7-(3-methyl-pyridin-2-yl)-yl)-pyrido[2,3-d]pyrimidin-4-yl]-amine | MS 415.2 |
| 35. | 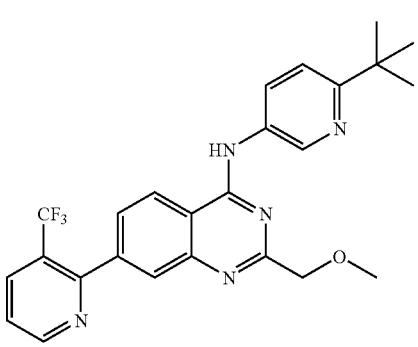 | (6-tert-Butyl-pyridin-3-yl)-[2-methoxymethyl-7-(3-trifluoromethyl-pyridin-2-yl)-quinazolin-4-yl]-amine | MS 468.4; $^1$H NMR(CDCl3): δ 1.40(9H, s), 3.57(3H, s), 4.70(2H, s), 7.41(1H, d, J= 8.8), 7.51(1H, m), 7.66(1H, d, J=8.0), 7.75(1H, br s), 8.03 (1H, d, J=8.5), 8.13(2H, m), 8.34(1H, dd, J=8.8, 2.8), 8.87 (2H, m). |
| 36. | 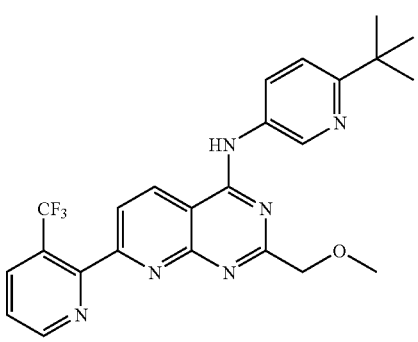 | (6-tert-Butyl-pyridin-3-yl)-[2-methoxymethyl-7-(3-trifluoromethyl-pyridin-2-yl)-pyrido[2,3-d]pyrimidin-4-yl]-amine | MS 469.2 |

TABLE I-continued

Representative Substituted (7-Pyridyl-4-Phenylamino-Quinazolin-2-yl)-Methanol Analogues

| | Compound | Name | MS(M + 1)/$^1$H NMR |
|---|---|---|---|
| 37. | | (6-tert-Butyl-pyridin-3-yl)-[7-(3-chloro-pyridin-2-yl)-2-ethoxymethyl-quinazolin-4-yl]-amine | MS 448.4 |
| 38. | | (6-tert-Butyl-pyridin-3-yl)-[7-(3-chloro-pyridin-2-yl)-2-isobutoxymethyl-pyrido[2,3-d]pyrimidin-4-yl]-amine | MS 477.2 |
| 39. | | (6-tert-Butyl-pyridin-3-yl)-[7-(3-chloro-pyridin-2-yl)-2-methoxymethyl-quinazolin-4-yl]-amine | MS 434.3 |
| 40. | | (6-tert-Butyl-pyridin-3-yl)-[7-(3-chloro-pyridin-2-yl)-2-methoxymethyl-pyrido[2,3-d]pyrimidin-4-yl]-amine | MS 435.2 |

TABLE I-continued

Representative Substituted (7-Pyridyl-4-Phenylamino-Quinazolin-2-yl)-Methanol Analogues

| Compound | Name | MS(M + 1)/$^1$H NMR |
|---|---|---|
| 41. | [2-(Tetrahydro-pyran-4-yloxymethyl)-7-(3-trifluoromethyl-pyridin-2-yl)-quinazolin-4-yl]-(4-trifluoromethyl-phenyl)-amine | MS 549.5 |
| 42. | [2-(Tetrahydro-pyran-4-yloxymethyl)-7-(3-trifluoromethyl-pyridin-2-yl)-quinazolin-4-yl]-(6-trifluoromethyl-pyridin-3-yl)-amine | MS 550.2 |
| 43. | [2-Benzyloxymethyl-7-(3-trifluoromethyl-pyridin-2-yl)-quinazolin-4-yl]-[4-(2,2,2-trifluoro-1-methyl-ethyl)-phenyl]-amine | MS 583.3 |
| 44. | [2-Benzyloxymethyl-7-(3-trifluoromethyl-pyridin-2-yl)-quinazolin-4-yl]-(4-trifluoromethyl-phenyl)-amine | MS 555.3 |
| 45. | [2-Benzyloxymethyl-7-(3-trifluoromethyl-pyridin-2-yl)quinazolin-4-yl]-(6-trifluoromethyl-pyridin-3-yl)-amine | MS 556.3 |

TABLE I-continued

Representative Substituted (7-Pyridyl-4-Phenylamino-Quinazolin-2-yl)-Methanol Analogues

| Compound | Name | MS(M + 1)/$^1$H NMR |
|---|---|---|
| 46. | [2-Benzyloxymethyl-7-(3-trifluoromethyl-pyridin-2-yl)quinazolin-4-yl]-(6-trifluoromethyl-pyridin-2-yl)-amine | MS 556.3 |
| 47. | [2-Benzyloxymethyl-7-(3-trifluoromethyl-pyridin-2-yl)-quinazolin-4-yl]-[4-(2-methoxy-1,1-dimethyl-ethyl)-phenyl]-amine | MS 573.4 |
| 48. | [2-Benzyloxymethyl-7-(3-trifluoromethyl-pyridin-2-yl)-quinazolin-4-yl]-(4-tert-butyl-phenyl)-amine | MS 543.4 |
| 49. | [2-Ethoxymethyl-7-(3-methyl-pyridin-2-yl)-pyrido[2,3-d]pyrimidin-4-yl]-(4-trifluoromethyl-phenyl)-amine | |

TABLE I-continued

Representative Substituted (7-Pyridyl-4-Phenylamino-Quinazolin-2-yl)-Methanol Analogues

| Compound | | Name | MS(M + 1)/$^1$H NMR |
|---|---|---|---|
| 50. | | [2-Ethoxymethyl-7-(3-methyl-pyridin-2-yl)-pyrido[2,3-d]pyrimidin-4-yl]-(4-isopropyl-phenyl)-amine | |
| 51. | | [2-Ethoxymethyl-7-(3-methyl-pyridin-2-yl)-quinazolin-4-yl]-(4-isopropyl-phenyl)-amine | MS 413.4 |
| 52. | | [2-Ethoxymethyl-7-(3-methyl-pyridin-2-yl)-quinazolin-4-yl]-(4-trifluoromethyl-phenyl)-amine | MS 439.4 |
| 53. | | [2-Ethoxymethyl-7-(3-trifluoromethyl-pyridin-2-yl)-pyrido[2,3-d]pyrimidin-4-yl]-(4-trifluoromethyl-phenyl)-amine | MS 494.3 |

TABLE I-continued

Representative Substituted (7-Pyridyl-4-Phenylamino-Quinazolin-2-yl)-Methanol Analogues

| | Compound | Name | MS(M + 1)/$^1$H NMR |
|---|---|---|---|
| 54. | | [2-Ethoxymethyl-7-(3-trifluoromethyl-pyridin-2-yl)-pyrido[2,3-d]pyrimidin-4-yl]-(6-trifluoromethyl-pyridin-3-yl)-amine | MS 495.3 |
| 55. | | [2-Ethoxymethyl-7-(3-trifluoromethyl-pyridin-2-yl)-pyrido[2,3-d]pyrimidin-4-yl]-4-(2,2,2-trifluoro-1-methyl-ethyl)-phenyl]-amine | MS 522.2; $^1$H NMR(DMSO-D6): δ 1.1(3H, t), 1.45(3H, d, J=1.5), 3.60(2H, q), 3.84(1H, m), 4.66(2H, s), 7.48(2H, d, J=1.9), 7.83(3H, m), 8.14(1H, d, J=2.1), 8.45(1H, d, J=2.0), 9.01(1H, s), 9.64(1H, d, J=2.0) |
| 56. | | [2-Ethoxymethyl-7-(3-trifluoromethyl-pyridin-2-yl)-quinazolin-4-yl]-(4-trifluoromethyl-phenyl)-amine | MS 493.3 |
| 57. | | [2-Ethoxymethyl-7-(3-trifluoromethyl-pyridin-2-yl)-quinazolin-4-yl]-(6-trifluoromethyl-pyridin-3-yl)-amine | MS 494.3 |

TABLE I-continued

Representative Substituted (7-Pyridyl-4-Phenylamino-Quinazolin-2-yl)-Methanol Analogues

| Compound | Name | MS(M + 1)/$^1$H NMR |
|---|---|---|
| 58. | [2-Isobutoxymethyl-7-(3-methyl-pyridin-2-yl)-pyrido[2,3-d]pyrimidin-4-yl]-(4-isopropyl-phenyl)-amine | |
| 59. | [2-Isobutoxymethyl-7-(3-methyl-pyridin-2-yl)-pyrido[2,3-d]pyrimidin-4-yl]-(4-trifluoromethyl-phenyl)-amine | MS 468.4 |
| 60. | [2-Isobutoxymethyl-7-(3-methyl-pyridin-2-yl)-pyrido[2,3-d]pyrimidin-4-yl]-[4-(2-methoxy-1,1-dimethyl-ethyl)-phenyl]amine | MS 486.5 |
| 61. | [2-Isobutoxymethyl-7-(3-trifluoromethyl-pyridin-2-yl)-pyrido[2,3-d]pyrimidin-4-yl]-(4-isopropyl-phenyl)-amine | MS 496.4 |

TABLE I-continued

Representative Substituted (7-Pyridyl-4-Phenylamino-Quinazolin-2-yl)-Methanol Analogues

| | Compound | Name | MS(M + 1)/¹H NMR |
|---|---|---|---|
| 62. | 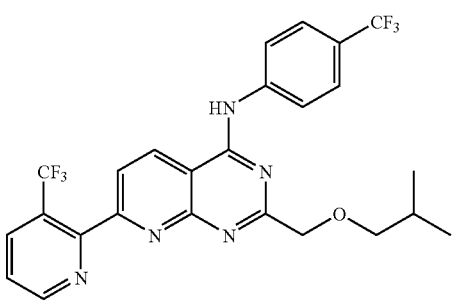 | [2-Isobutoxymethyl-7-(3-trifluoromethyl-pyridin-2-yl)-pyrido[2,3-d]pyrimidin-4-yl]-(4-trifluoromethyl-phenyl)-amine | MS 522.2 |
| 63. | 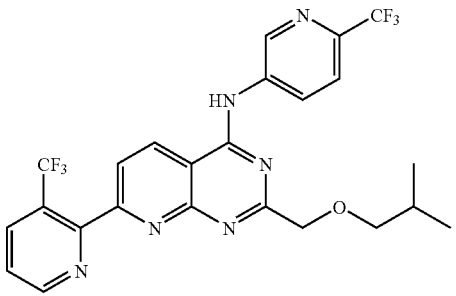 | [2-Isobutoxymethyl-7-(3-trifluoromethyl-pyridin-2-yl)-pyrido[2,3-d]pyrimidin-4-yl]-(6-trifluoromethyl-pyridin-3-yl)-amine | MS 523.3 |
| 64. | 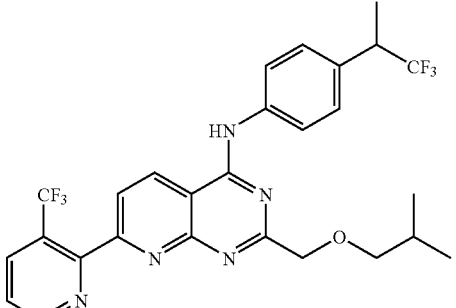 | [2-Isobutoxymethyl-7-(3-trifluoromethyl-pyridin-2-yl)-pyrido[2,3-d]pyrimidin-4-yl]-[4-(2,2,2-trifluoro-1-methyl-ethyl)-phenyl]-amine | MS 550.2; ¹H NMR(DMSO-D6): δ 0.82(6H, d, J=1.7), 1.44 (3H, d, J=1.9), 1.8(1H, m), 3.34(2H, d, J=1.7), 3.85(1H, m), 4.67(2H, s), 7.46(2H, d, J=2.1), 7.88(3H, m), 8.14 (1H, d, J=2.1), 8.47(1H, d, J=1.9), 9.01(1H, s,), 9.64(1H, d, J=2.1) |
| 65. | 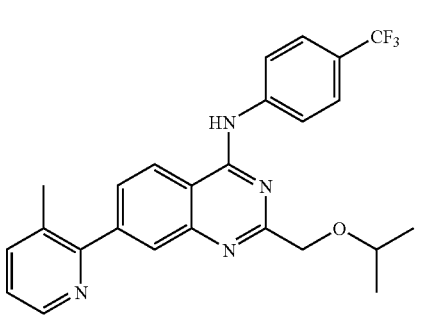 | [2-Isopropoxymethyl-7-(3-methyl-pyridin-2-yl)-quinazolin-4-yl]-(4-trifluoromethyl-phenyl)-amine | MS 453.4 |

TABLE I-continued

Representative Substituted (7-Pyridyl-4-Phenylamino-Quinazolin-2-yl)-Methanol Analogues

| Compound | Name | MS(M + 1)/$^1$H NMR |
|---|---|---|
| 66. | [2-Isopropoxymethyl-7-(3-methyl-pyridin-2-yl)-quinazolin-4-yl]-(4-isopropyl-phenyl)-amine | MS 427.4 |
| 67. | [2-Isopropoxymethyl-7-(3-trifluoromethyl-pyridin-2-yl)-quinazolin-4-yl]-(6-trifluoromethyl-pyridin-3-yl)-amine | MS 508.2 |
| 68. | [2-Methoxymethyl-7-(3-methyl-pyridin-2-yl)-pyrido[2,3-d]pyrimidin-4-phenyl)-amine | MS 426.3 |
| 69. | [2-Methoxymethyl-7-(3-methyl-pyridin-2-yl)-pyrido[2,3-d]pyrimidin-4-yl]-(6-trifluoromethyl-pyridin-3-yl)-amine | |

TABLE I-continued

Representative Substituted (7-Pyridyl-4-Phenylamino-Quinazolin-2-yl)-Methanol Analogues

| Compound | Name | MS(M + 1)/$^1$H NMR |
|---|---|---|
| 70. | [2-Methoxymethyl-7-(3-trifluoromethyl-pyridin-2-yl)-pyrido[2,3-d]pyrimidin-4-yl]-[4-(2,2,2-trifluoro-1-methyl-ethyl)-phenyl]-amine | |
| 71. | [2-Methoxymethyl-7-(3-trifluoromethyl-pyridin-2-yl)-pyrido[2,3-d]pyrimidin-phenyl)-amine | MS 480.3 |
| 72. | [2-Methoxymethyl-7-(3-trifluoromethyl-pyridin-2-yl)-pyrido[2,3-d]pyrimidin-4-yl]-(6-trifluoromethyl-pyridin-3-yl)-amine | |
| 73. | [2-Methoxymethyl-7-(3-trifluoromethyl-pyridin-2-yl)-quinazolin-4-yl]-(4-trifluoromethyl-phenyl)-amine | MS 479.2 |
| 74. | [2-Methoxymethyl-7-(3-trifluoromethyl-pyridin-2-yl)-quinazolin-4-yl]-(5-trifluoromethyl-pyridin-2-yl)-amine | MS 480.2 |

TABLE I-continued

Representative Substituted (7-Pyridyl-4-Phenylamino-Quinazolin-2-yl)-Methanol Analogues

| Compound | Name | MS(M + 1)/$^1$H NMR |
|---|---|---|
| 75. | [2-Methoxymethyl-7-(3-trifluoromethyl-pyridin-2-yl)-quinazolin-4-yl]-(6-trifluoromethyl-pyridin-3-yl)-amine | MS 480.2 |
| 76. | [4-(2-Methoxy-1,1-dimethyl-ethyl)-phenyl]-[2-methoxymethyl-7-(3-trifluoromethyl-pyridin-2-yl)-quinazolin-4-yl]-amine | MS 497.3 |
| 77. | [4-(4-Isopropyl-phenylamino)-7-(3-trifluoromethyl-pyridin-2-yl)-quinazolin-2-yl]-methanol | MS 439.2 |
| 78. | [4-(4-tert-Butyl-phenylamino)-7-(3-chloro-pyridin-2-yl)-quinazolin-2-yl]-methanol | MS 419.2; $^1$H NMR(DMSO-d$_6$): δ 1.29(9H, s), 4.50(2H, d, J=5.6), 4.99(1H, br), 7.38(2H, d, J=8.5), 7.52(1H, m), 7.85 (3H, m), 8.02(1H, s), 8.12(1H, m), 8.69(2H, m), 9.82(1H, br). |

TABLE I-continued

Representative Substituted (7-Pyridyl-4-Phenylamino-Quinazolin-2-yl)-Methanol Analogues

| Compound | Name | MS(M + 1)/¹H NMR |
|---|---|---|
| 79. | [4-(4-tert-Butyl-phenylamino)-7-(3-methyl-pyridin-2-yl)-pyrido[2,3-d]pyrimidin-2-yl]-methanol | MS 400.3 |
| 80. | [4-(4-tert-Butyl-phenylamino)-7-(3-trifluoromethyl-pyridin-2-yl)-quinazolin-2-yl]-methanol | MS 453.2 |
| 81. | [4-(4-Trifluoromethyl-phenylamino)-7-(3-trifluoromethyl-pyridin-2-yl)-quinazolin-2-yl]-methanol | MS 465.2 |
| 82. | [4-(4-Trifluoromethyl-phenylamino)-7-(3-trifluoromethyl-pyridin-2-yl)-pyrido[2,3-d]pyrimidin-2-yl]-methanol | MS 466.3 |

TABLE I-continued

Representative Substituted (7-Pyridyl-4-Phenylamino-Quinazolin-2-yl)-Methanol Analogues

| | Compound | Name | MS(M + 1)/$^1$H NMR |
|---|---|---|---|
| 83. | | [7-(3-Chloro-pyridin-2-yl)-2-(1-methoxy-ethyl)-pyrido[2,3-d]pyrimidin-4-yl]-(4-trifluoromethyl-phenyl)-amine | MS 460.3 |
| 84. | | [7-(3-Chloro-pyridin-2-yl)-(2-methoxy-ethoxymethyl)-pyrido[2,3-d]pyrimidin-4-yl]-(4-trifluoromethyl-phenyl)-amine | |
| 85. | | [7-(3-Chloro-pyridin-2-yl)-2-(2-methoxy-ethoxymethyl)-pyrido[2,3-d]pyrimidin-4-yl]-(4-isopropyl-phenyl)-amine | MS 464.4 |
| 86. | | [7-(3-Chtoro-pyridin-2-yl)-2-(tetrahydro-pyran-4-yloxymethyl)-quinazolin-4-yl]-(4-trifluoromethyl-phenyl)-amine | MS 515.4 |

TABLE I-continued

Representative Substituted (7-Pyridyl-4-Phenylamino-Quinazolin-2-yl)-Methanol Analogues

| Compound | | Name | MS(M + 1)/¹H NMR |
|---|---|---|---|
| 87. | 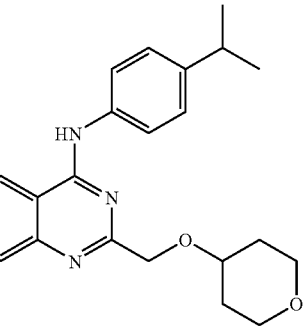 | [7-(3-Chloro-pyridin-2-yl)-2-(tetrahydro-pyran-4-yloxymethyl)-quinazolin-4-yl]-(4-isopropyl-phenyl)-amine | MS 489.4 |
| 88. | 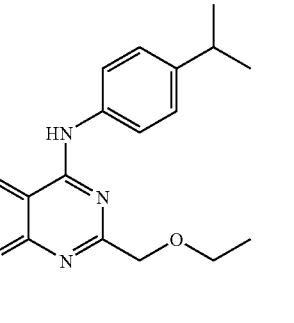 | [7-(3-Chloro-pyridin-2-yl)-2-ethoxymethyl-pyrido[2,3-d]pyrimidin-4-yl]-(4-isopropyl-phenyl)-amine | |
| 89. | 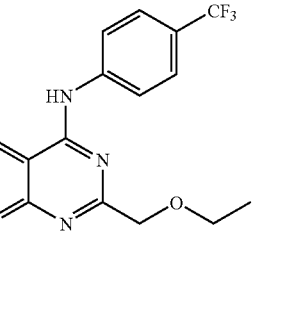 | [7-(3-Chloro-pyridin-2-yl)-2-ethoxymethyl-pyrido[2,3-d]pyrimidin-4-yl]-(4-trifluoromethyl-phenyl)-amine | |
| 90. | 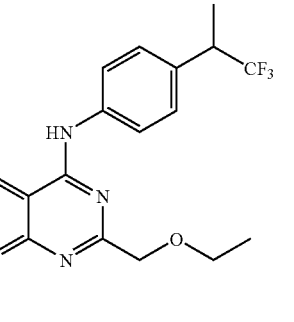 | [7-(3-Chloro-pyridin-2-yl)-2-ethoxymethyl-pyrido[2,3-d]pyrimidin-4-yl]-[4-(2,2,2-trifluoro-1-methyl-ethyl)-phenyl]-amine | |

TABLE I-continued

Representative Substituted (7-Pyridyl-4-Phenylamino-Quinazolin-2-yl)-Methanol Analogues

| | Compound | Name | MS(M + 1)/¹H NMR |
|---|---|---|---|
| 91. | | [7-(3-Chloro-pyridin-2-yl)-2-ethoxymethyl-pyrido[2,3-]pyrimidin-4-yl]-(4-difluoromethyl-phenyl)-amine | MS 442.3 |
| 92. | | [7-(3-Chloro-pyridin-2-yl)-2-ethoxymethyl-pyrido[2,3-d]pyrimidin-4-yl]-(6-trifluoromethyl-pyridin-3-yl)-amine | |
| 93. | | [7-(3-Chloro-pyridin-2-yl)-2-ethoxymethyl-quinazolin-4-yl]-(4-isopropyl-phenyl)-amine | MS 433.4 |
| 94. | | [7-(3-Chloro-pyridin-2-yl)-2-ethoxymethyl-quinazolin-4-yl]-(4-trifluoromethyl-phenyl)-amine | MS 459.3 |

TABLE I-continued

Representative Substituted (7-Pyridyl-4-Phenylamino-Quinazolin-2-yl)-Methanol Analogues

| | Compound | Name | MS(M + 1)/$^1$H NMR |
|---|---|---|---|
| 95. | 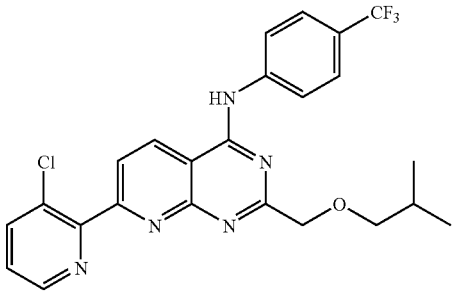 | [7-(3-Chloro-pyridin-2-yl)-2-isobutoxymethyl-pyrido[2,3-d]pyrimidin-4-yl]-(4-trifluoromethyl-phenyl)-amine | MS 488.1 |
| 96. | 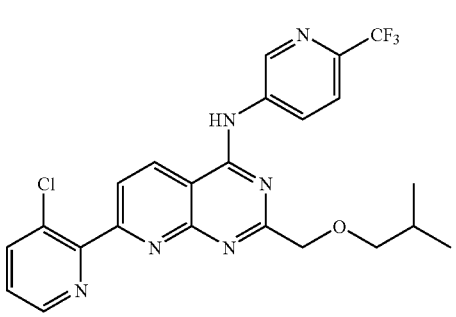 | [7-(3-Chloro-pyridin-2-yl)-2-isobutoxymethyl-pyrido[2,3-d]pyrimidin-4-yl]-(6-trifluoromethyl-pyridin-3-yl)-amine | MS 489.1 |
| 97. | 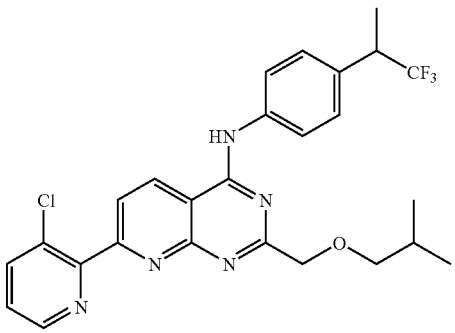 | [7-(3-Chloro-pyridin-2-yl)-2-isobutoxymethyl-pyrido[2,3-d]pyrimidin-4-yl]-[4-(2,2,2-trifluoro-1-methyl-ethyl)-phenyl]-amine | MS 516.2; $^1$H NMR(DMSO-D6): 60.82(6H, d, J=1.7), 1.45 (3H, d, J=1.8), 1.8(1H, m), 3.34(2H, d, J=2.6), 3.85(1H, m), 4.68(2H, s), 7.46(2H, d, J=2.2), 7.63(1H, m), 7.88(2H, d, J=2.1), 8.18 (2H, m), 8.73 (1H, d, J=2.2), 9.66(1H, d, J=2.1) |
| 98. | 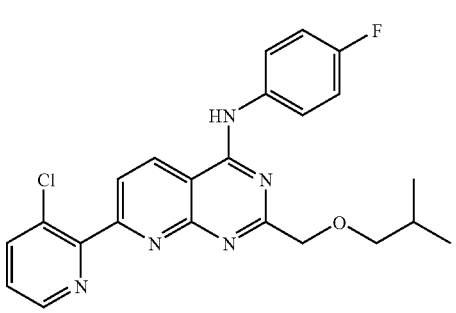 | [7-(3-Chloro-pyridin-2-yl)-2-isobutoxymethyl-pyrido[2,3-d]pyrimidin-4-yl]-(4-fluoro-phenyl)-amine | MS 438.2 |
| 99. | 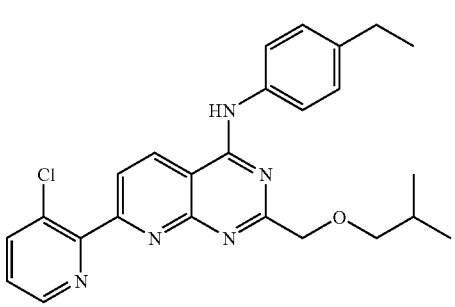 | [7-(3-Chloro-pyridin-2-yl)-2-isobutoxymethyl-pyrido[2,3-d]pyrimidin-4-yl]-(4-ethyl-phenyl)-amine | MS 448.2 |

TABLE I-continued

Representative Substituted (7-Pyridyl-4-Phenylamino-Quinazolin-2-yl)-Methanol Analogues

| Compound | Name | MS(M + 1)/$^1$H NMR |
|---|---|---|
| 100. | [7-(3-Chloro-pyridin-2-yl)-2-isobutoxymethyl-pyrido[2,3-d]pyrimidin-4-yl]-(4-propyl-phenyl)-amine | MS 462.3 |
| 101. | [7-(3-Chloro-pyridin-2-yl)-2-isobutoxymethyl-pyrido[2,3-d]pyrimidin-4-yl]-(4-ethynyl-phenyl)-amine | MS 444.2 |
| 102. | [7-(3-Chloro-pyridin-2-yl)-2-methoxymethyl-pyrido[2,3-d]pyrimidin-4-yl]-(4-isopropyl-phenyl)-amine | MS 420.2 |
| 103. | [7-(3-Chloro-pyridin-2-yl)-2-methoxymethyl-pyrido[2,3-d]pyrimidin-4-yl]-[4-(2-methoxy-1,1-dimethyl-ethyl)-phenyl]-amine | MS 464.2 |

TABLE I-continued

Representative Substituted (7-Pyridyl-4-Phenylamino-Quinazolin-2-yl)-Methanol Analogues

| Compound | | Name | MS(M + 1)/$^1$H NMR |
|---|---|---|---|
| 104. | | [7-(3-Chloro-pyridin-2-yl)-2-methoxymethyl-pyrido[2,3-d]pyrimidin-4-yl]-(4-difluoromethyl-phenyl)-amine | MS 428.3 |
| 105. | | [7-(3-Chloro-pyridin-2-yl)-2-methoxymethyl-quinazolin-4-yl]-(4-isopropyl-phenyl)-amine | MS 419.3 |
| 106. | | [7-(3-Chloro-pyridin-2-yl)-2-methoxymethyl-quinazolin-4-yl]-(4-trifluoromethyl-phenyl)amine | MS 445.3 |
| 107. | | [7-(3-Chloro-pyridin-2-yl)-4-(4-isopropyl-phenylamino)-quinazolin-2-yl]-methanol | MS 405.1 |

TABLE I-continued

Representative Substituted (7-Pyridyl-4-Phenylamino-Quinazolin-2-yl)-Methanol Analogues

| Compound | Name | MS(M + 1)/$^1$H NMR |
|---|---|---|
| 108. | [7-(3-Methyl-pyridin-2-yl)-2-(tetrahydro-pyran-4-yloxymethyl)-quinazolin-4-yl]-(4-trifluoromethyl-phenyl)-amine | MS 495.4 |
| 109. | [7-(3-Methyl-pyridin-2-yl)-4-(4-trifluoromethyl-phenylamino)-pyrido[2,3-d]pyrimidin-2-yl]-methanol | MS 412.3 |
| 110. | 1-{4-[2-Isobutoxymethyl-7-(3-methyl-pyridin-2-yl)-pyrido[2,3-d]pyrimidin-4-ylamino]-phenyl}-cyclobutanecarbonitrile | MS 479.4 |
| 111. | 1-{4-[2-Methoxymethyl-7-(3-methyl-pyridin-2-yl)-pyrido[2,3-d]pyrimidin-4-ylamino]-phenyl}-cyclobutanecarbonitrile | MS 437.2 |

TABLE I-continued

Representative Substituted (7-Pyridyl-4-Phenylamino-Quinazolin-2-yl)-Methanol Analogues

| Compound | | Name | MS(M + 1)/$^1$H NMR |
|---|---|---|---|
| 112. | | 1-{4-[7-(3-Chloro-pyridin-2-yl)-2-ethoxymethyl-pyrido[2,3-d]pyrimidin-4-ylamino]-phenyl}-cyclobutanecarbonitrile | MS 471.2 |
| 113. | | 2-{4-[2-Benzyloxymethyl-7-(3-trifluorometbyl-pyridin-2-yl)-quinazolin-4-ylamino]-phenyl}-2-methyl-propionitrile | MS 554.4 |
| 114. | | 2-{4-[2-Ethoxymethyl-7-(3-trifluoromethylpyridin-2-yl)-pyrido[2,3-d]pyrimidin-4-ylamino]-phenyl}-2-methyl-propionitrile | MS 493.4 |
| 115. | | 2-{4-[2-Isobutoxymethyl-7-(3-methyl-pyridin-2-yl)-pyrido[2,3-d]pyrimidin-4-ylamino]-phenyl}-2-methyl-propionitrile | MS 467.2 |

TABLE I-continued

Representative Substituted (7-Pyridyl-4-Phenylamino-Quinazolin-2-yl)-Methanol Analogues

| Compound | | Name | MS(M + 1)/¹H NMR |
|---|---|---|---|
| 116. | 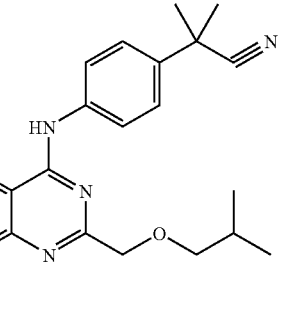 | 2-{4-[2-Isobutoxymethyl-7-(3-trifluoromethyl-pyridin-2-yl)-pyrido[2,3-d]pyrimidin-4-ylamino]-phenyl}-2-methyl-propionitrile | MS 521.4 |
| 117. | 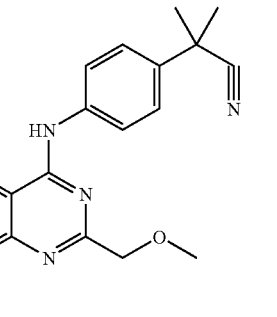 | 2-{4-[2-Methoxymethyl-7-(3-methyl-pyridin-2-yl)-pyrido[2,3-d]pyrimidin-4-ylamino]-phenyl}-2-methyl-propionitrile | MS 425.4 |
| 118. | 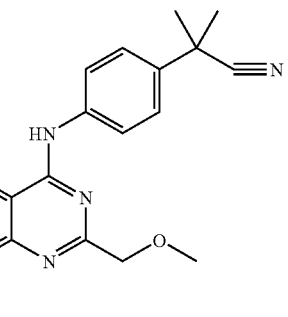 | 2-{4-[2-Methoxymethyl-7-(3-trifluoromethyl-pyridin-2-yl)-pyrido[2,3-d]pyrimidin-4-ylamino]-phenyl}-2-methyl-propionitrile | MS 479.2; ¹H NMR(DMSO-D6): δ 1.72(6H, s), 3.44(3H, s), 4.63(2H, s), 7.62(1H, d, J=2.1), 7.85(1H, m), 7.95(1H, d, J=2.1), 8.15(1H, d, J =2.1), 8.46(1H, d, J 2.0), 9.02(1H, D, J=2.1), 9.64(1H, d, J=2.2), 12.05(1H, bs). |
| 119. | 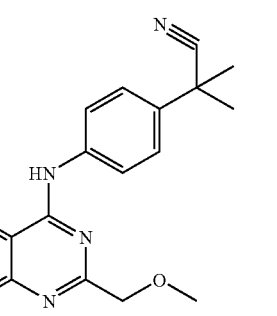 | 2-{4-[2-Methoxymethyl-7-(3-trifluoromethyl-pyridin-2-yl)-quinazolin-4-ylamino]-phenyl}-2-methyl-propionitrile | MS 478.2 |

TABLE I-continued

Representative Substituted (7-Pyridyl-4-Phenylamino-Quinazolin-2-yl)-Methanol Analogues

| | Compound | Name | MS(M + 1)/¹H NMR |
|---|---|---|---|
| 120. | 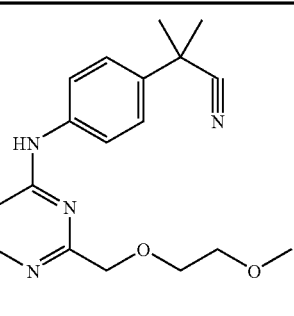 | 2-{4-[7-(3-Chloro-pyridin-2-yl)-2-(2-methoxy-ethoxymethyl)-pyrido[2,3-d]pyrimidin-4-ylamino]-phenyl}-2-methyl-propionitrile | MS 489.4 |
| 121. | 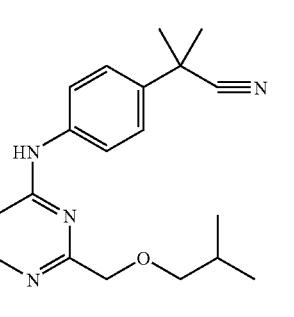 | 2-{4-[7-(3-Chloro-pyridin-2-yl)-2-isobutoxymethyl-pyrido[2,3-d]pyrimidin-4-ylamino]-phenyl}-2-methyl-propionitrile | MS 487.2 |
| 122. | 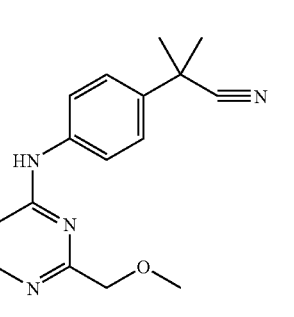 | 2-{4-[7-(3-Chloro-pyridin-2-yl)-2-methoxymethyl-pyrido[2,3-d]pyrimidin-4-ylaminol-phenyl}-2-methyl-propionitrile | MS 445.2 |
| 123. | 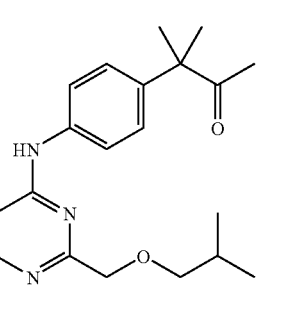 | 3-{4-[2-Isobutoxymethyl-7-(3-methyl-pyridin-2-yl)-pyrido[2,3-d]pyrimidin-4-ylaminol-phenyl}-3-methyl-butan-2-one | MS 484.3 |

TABLE I-continued

Representative Substituted (7-Pyridyl-4-Phenylamino-Quinazolin-2-yl)-Methanol Analogues

| Compound | | Name | MS(M + 1)/¹H NMR |
|---|---|---|---|
| 124. | | 3-{4-[2-Isobutoxymethyl-7-(3-trifluoromethyl-pyridin-2-yl)-pyridol]2,3-d]pyrimidin-4-ylamino]-phenyl}-3-methyl-butan-2-one | MS 538.2 |
| 125. | | 3-{4-[2-Methoxymethyl-7-(3-methyl-pyridin-2-yl)-pyrido[2,3-d]pyrimidin-4-ylamino]-phenyl}-3-methyl-butan-2-one | MS 442.2 |
| 126. | | 3-{4-[2-Methoxymethyl-7-(3-trifluoron3ethyl-pyridin-2-yl)-pyrido[2,3-d]pyrimidin-4-ylamino]-phenyl}-3-methyl-butan-2-one | MS 496.2 |
| 127. | | 3-{4-[7-(3-Chloro-pyridin-2-yl)-2-isobutoxymethyl-pyrido[2,3-d]pyrimidin-4-ylamino]-phenyl}-3-methyl-butan-2-one | MS 504.2 |

TABLE I-continued

Representative Substituted (7-Pyridyl-4-Phenylamino-Quinazolin-2-yl)-Methanol Analogues

| Compound | | Name | MS(M + 1)/$^1$H NMR |
|---|---|---|---|
| 128. | | 3-{4-[7-(3-Chloro-pyridin-2-yl)-2-methoxymethyl-pyrido[2,3-d]pyrimidin-4-ylamino]-phenyl}-3-methyl-butan-2-one | MS 462.2 |
| 129. | | 4-[2-Isobutoxymethyl-7-(3-trifluoromethyl-pyridin-2-yl)-pyrido[2,3-d]pyrimidin-4-ylamino]-benzonitrile | MS 479.3 |
| 130. | | 4-[2-Methoxymethyl-7-(3-trifluoromethyl-pyridin-2-yl)-pyrido[2,3-dipyrimidin-4-ylamino]-benzonitrile | MS 309.0; $^1$H NMR(DMSO-D6): δ 3.45(3H, s), 4.66(2H, s), 7.84(1H, m), 7.93(1H, d, J=2.1), 8.14(1H, d, J=2.1), 8.21(1H, d, J=2.2), 8.46(1H, d, J=2.1), 9.01(1H, d, J=1.1), 9.62(1H, d, J=2.1), 11.9(1H, bs). |
| 131. | | 4-[7-(3-Chloro-pyridin-2-yl)-2-isobutoxymethyl-pyrido[2,3-d]pyrimidin-4-ylamino]-benzonitrile | MS 445.2 |
| 132. | | [2-Isobutoxymethyl-7-(3-trifluoromethyl-pyridin-2-yl)-pyrido[2,3-d]pyrimidin-4-yl]-(5-trifluoromethyl-pyridin-2-yl)-amine | MS 523.2 |

TABLE I-continued

Representative Substituted (7-Pyridyl-4-Phenylamino-Quinazolin-2-yl)-Methanol Analogues

| Compound | Name | MS(M + 1)/$^1$H NMR |
|---|---|---|
| 133. | [2-Methoxymethyl-7-(3-trifluoromethyl-pyridin-2-yl)-pyrido[2,3-d]pyrimidin-4-yl]-(5-trifluoromethyl-pyridin-2-yl)-amine | MS 481.2 |

Example 4

VR1-Transfected Cells and Membrane Preparations

This Example illustrates the preparation of VR1-transfected cells and VR1-containing membrane preparations for use in capsaicin binding assays (Example 5).

A cDNA encoding full length human capsaicin receptor recited in U.S. Pat. No. 6,482,611 was subcloned in the plasmid pBK-CMV (Stratagene, La Jolla, Cailf.) for recombinant expression in mammalian cells.

Human embryonic kidney (HEK293) cells were transfected with the pBK-CMV expression construct encoding the full length human capsaicin receptor using standard methods. The transfected cells were selected for two weeks in media containing G418 (400 µg/ml) to obtain a pool of stably transfected cells. Independent clones were isolated from this pool by limiting dilution to obtain clonal stable cell lines for use in subsequent experiments.

For radioligand binding experiments, cells were seeded in T175 cell culture flasks in media without antibiotics and grown to approximately 90% confluency. The flasks were then washed with PBS and harvested in PBS containing 5 mM EDTA. The cells were pelleted by gentle centrifugation and stored at −80° C. until assayed.

Previously frozen cells were disrupted with the aid of a tissue homogenizer in ice-cold HEPES homogenization buffer (5 mM KCl 5, 5.8 mM NaCl, 0.75 mM $CaCl_2$, 2 mM $MgCl_2$, 320 mM sucrose, and 10 mM HEPES pH 7.4). Tissue homogenates were first centrifuged for 10 minutes at 1000×g (4° C.) to remove the nuclear fraction and debris, and then the supernatant from the first centrifugation is further centrifuged for 30 minutes at 35,000×g (4° C.) to obtain a partially purified membrane fraction. Membranes were resuspended in the HEPES homogenization buffer prior to the assay. An aliquot of this membrane homogenate was used to determine protein concentration via the Bradford method (BIO-RAD Protein Assay Kit, #500-0001, BIO-RAD, Hercules, Calif.).

Example 5

Capsaicin Receptor Binding Assay

This Example illustrates a representative assay of capsaicin receptor binding that may be used to determine the binding affinity of compounds for the capsaicin (VR1) receptor.

Binding studies with [$^3$H] Resiniferatoxin (RTX) are carried out essentially as described by Szallasi and Blumberg (1992) *J. Pharmacol. Exp. Ter.* 262:883-888. In this protocol, non-specific RTX binding is reduced by adding bovine alpha, acid glycoprotein (100 µg per tube) after the binding reaction has been terminated.

[$^3$H] RTX (37 Ci/mmol) is synthesized by and obtained from the Chemical Synthesis and Analysis Laboratory, National Cancer Institute-Frederick Cancer Research and Development Center, Frederick, Md. [$^3$H] RTX may also be obtained from commercial vendors (e.g., Amersham Pharmacia Biotech, Inc.; Piscataway, N.J.).

The membrane homogenate of Example 4 is centrifuged as before and resuspended to a protein concentration of 333 µg/ml in homogenization buffer. Binding assay mixtures are set up on ice and contain [$^3$H]RTX (specific activity 2200 mCi/ml), 2 µl non-radioactive test compound, 0.25 mg/ml bovine serum albumin (Cohn fraction V), and $5\times10^4$-$1\times10^5$ VR1-transfected cells. The final volume is adjusted to 500 µl (for competition binding assays) or 1,000 µl (for saturation binding assays) with the ice-cold HEPES homogenization buffer solution (pH 7.4) described above. Non-specific binding is defined as that occurring in the presence of 1 µM non-radioactive RTX (Alexis Corp.; San Diego, Calif.). For saturation binding, [$^3$H]RTX is added in the concentration range of 7-1,000 pM, using 1 to 2 dilutions. Typically 11 concentration points are collected per saturation binding curve.

Competition binding assays are performed in the presence of 60 pM [$^3$H]RTX and various concentrations of test compound. The binding reactions are initiated by transferring the assay mixtures into a 37° C. water bath and are terminated following a 60 minute incubation period by cooling the tubes on ice. Membrane-bound RTX is separated from free, as well as any alpha,-acid glycoprotein-bound RTX, by filtration onto WALLAC glass fiber filters (PERKN-ELMER, Gaithersburg, Md.) which were pre-soaked with 1.0% PEI (polyethyleneimine) for 2 hours prior to use. Filters are allowed to dry overnight then counted in a WALLAC 1205 BETA PLATE counter after addition of WALLAC BETA SCINT scintillation fluid.

Equilibrium binding parameters are determined by fitting the allosteric Hill equation to the measured values with the aid of the computer program FIT P (Biosoft, Ferguson, Mo.) as described by Szallasi, et al. (1993) *J. Pharmacol. Exp. Ther.* 266:678-683. Compounds provided herein generally exhibit $K_i$ values for capsaicin receptor of less than 1 μM, 100 nM, 50 nM, 25 nM, 10 nM, or 1 nM in this assay.

Example 6

Calcium Mobilization Assay

This Example illustrates representative calcium mobilization assays for use in evaluating test compounds for agonist and antagonist activity.

Cells transfected with expression plasmids (as described in Example 4) and thereby expressing human capsaicin receptor are seeded and grown to 70-90% confluency in FALCON black-walled, clear-bottomed 96-well plates (#3904, BECTON-DICKINSON, Franklin Lakes, N.J.). The culture medium is emptied from the 96 well plates and FLUO-3 AM calcium sensitive dye (Molecular Probes, Eugene, Oreg.) is added to each well (dye solution: 1 mg FLUO-3 AM, 440 μL DMSO and 440 μl 20% pluronic acid in DMSO, diluted 1:250 in Krebs-Ringer HEPES (KRH) buffer (25 mM HEPES, 5 mM KCl, 0.96 mM $NaH_2PO_4$, 1 mM $MgSO_4$, 2 mM $CaCl_2$, 5 mM glucose, 1 mM probenecid, pH 7.4), 50 μl diluted solution per well). Plates are covered with aluminum foil and incubated at 37° C. for 1-2 hours in an environment containing 5% $CO_2$. After the incubation, the dye is emptied from the plates, and the cells are washed once with KRH buffer, and resuspended in KRH buffer.

Determination Capsaicin $EC_{50}$

To measure the ability of a test compound to agonize or antagonize a calcium mobilization response in cells expressing capsaicin receptors to capsaicin or other vanilloid agonist, the $EC_{50}$ of the agonist capsaicin is first determined. An additional 20 μl of KRH buffer and 1 μl DMSO is added to each well of cells, prepared as described above. 100 μl capsaicin in KRH buffer is automatically transferred by the FLIPR instrument to each well. Capsaicin-induced calcium mobilization is monitored using either FLUOROSKAN ASCENT (Labsystems; Franklin, Mass.) or FLIPR (fluorometric imaging plate reader system; Molecular Devices, Sunnyvale, Calif.) instruments. Data obtained between 30 and 60 seconds after agonist application are used to generate an 8-point concentration response curve, with final capsaicin concentrations of 1 nM to 3 μM. KALEIDAGRAPH software (Synergy Software, Reading, Pa.) is used to fit the data to the equation:

$$y=a*(1/(1+(b/x)^c))$$

to determine the 50% excitatory concentration ($EC_{50}$) for the response. In this equation, y is the maximum fluorescence signal, x is the concentration of the agonist or antagonist (in this case, capsaicin), a is the $E_{max}$, b corresponds to the $EC_{50}$ value and c is the Hill coefficient.

Determination of Agonist Activity

Test compounds are dissolved in DMSO, diluted in KRH buffer, and immediately added to cells prepared as described above. 100 nM capsaicin (an approximate $EC_{90}$ concentration) is also added to cells in the same 96-well plate as a positive control. The final concentration of test compounds in the assay wells is between 0.1 nM and 5 μM.

The ability of a test compound to act as an agonist of the capsaicin receptor is determined by measuring the fluorescence response of cells expressing capsaicin receptors elicited by the compound as function of compound concentration. This data is fit as described above to obtain the $EC_{50}$, which is generally less than 1 micromolar, preferably less than 100 nM, and more preferably less than 10 nM. The extent of efficacy of each test compound is also determined by calculating the response elicited by a concentration of test compound (typically 1 μM) relative to the response elicited by 100 nM capsaicin. This value, called Percent of Signal (POS), is calculated by the following equation:

POS=100*test compound response/100 nM capsaicin response

This analysis provides quantitative assessment of both the potency and efficacy of test compounds as human capsaicin receptor agonists. Agonists of the human capsaicin receptor generally elicit detectable responses at concentrations less than 100 μM, or preferably at concentrations less than 1 μM, or most preferably at concentrations less than 10 nM. Extent of efficacy at human capsaicin receptor is preferably greater than 30 POS, more preferably greater than 80 POS at a concentration of 1 μM. Certain agonists are essentially free of antagonist activity as demonstrated by the absence of detectable antagonist activity in the assay described below at compound concentrations below 4 nM, more preferably at concentrations below 10 μM and most preferably at concentrations less than or equal to 100 μM.

Determination of Antagonist Activity

Test compounds are dissolved in DMSO, diluted in 20 μl KRH buffer so that the final concentration of test compounds in the assay well is between 1 μM and 5 μM, and added to cells prepared as described above. The 96 well plates containing prepared cells and test compounds are incubated in the dark, at room temperature for 0.5 to 6 hours. It is important that the incubation not continue beyond 6 hours. Just prior to determining the fluorescence response, 100 μl capsaicin in KRH buffer at twice the $EC_{50}$ concentration determined as described above is automatically added by the FLIPR instrument to each well of the 96 well plate for a final sample volume of 200 μl and a final capsaicin concentration equal to the $EC_{50}$. The final concentration of test compounds in the assay wells is between 1 μM and 5 μM. Antagonists of the capsaicin receptor decrease this response by at least about 20%, preferably by at least about 50%, and most preferably by at least 80%, as compared to matched control (i.e., cells treated with capsaicin at twice the $EC_{50}$ concentration in the absence of test compound), at a concentration of 10 micromolar or less, preferably 1 micromolar or less. The concentration of antagonist required to provide a 50% decrease, relative to the response observed in the presence of capsaicin and without antagonist, is the $IC_{50}$ for the antagonist, and is preferably below 1 micromolar, 100 nanomolar, 10 nanomolar or 1 nanomolar.

Certain preferred VR1 modulators are antagonists that are essentially free of agonist activity as demonstrated by the absence of detectable agonist activity in the assay described above at compound concentrations below 4 nM, more preferably at concentrations below 10 μM and most preferably at concentrations less than or equal to 100 μM.

Example 7

Microsomal in vitro Half-Life

This Example illustrates the evaluation of compound half-life values ($t_{1/2}$ values) using a representative liver microsomal half-life assay.

Pooled human liver microsomes are obtained from Xeno-Tech LLC (Kansas City, Kans.). Such liver microsomes may also be obtained from In Vitro Technologies (Baltimore, Md.) or Tissue Transformation Technologies (Edison, N.J.). Six test reactions are prepared, each containing 25 μl microsomes, 5 μl of a 100 μM solution of test compound, and 399 μl 0.1 M phosphate buffer (19 mL 0.1 M $NaH_2PO_4$, 81 mL 0.1 M $Na_2HPO_4$, adjusted to pH 7.4 with $H_3PO_4$). A seventh reaction is prepared as a positive control containing 25 μl microsomes, 399 μl 0.1 M phosphate buffer, and 5 μl of a 100 μM solution of a compound with known metabolic properties (e.g., DIAZEPAM or CLOZAPINE). Reactions are preincubated at 39° C. for 10 minutes.

CoFactor Mixture is prepared by diluting 16.2 mg NADP and 45.4 mg Glucose-6-phosphate in 4 mL 100 mM $MgCl_2$. Glucose-6-phosphate dehydrogenase solution is prepared by diluting 214.3 μl glucose-6-phosphate dehydrogenase suspension (Roche Molecular Biochemicals; Indianapolis, Ind.) into 1285.7 μl distilled water. 71 μl Starting Reaction Mixture (3 mL CoFactor Mixture; 1.2 mL Glucose-6-phosphate dehydrogenase solution) is added to 5 of the 6 test reactions and to the positive control. 71 μl 100 mM $MgCl_2$ is added to the sixth test reaction, which is used as a negative control. At each time point (0, 1, 3, 5, and 10 minutes), 75 μl of each reaction mix is pipetted into a well of a 96-well deep-well plate containing 75 μl ice-cold acetonitrile. Samples are vortexed and centrifuged 10 minutes at 3500 rpm (Sorval T 6000D centrifuge, H1000B rotor). 75 μl of supernatant from each reaction is transferred to a well of a 96-well plate containing 150 μl of a 0.5 μM solution of a compound with a known LCMS profile (internal standard) per well. LCMS analysis of each sample is carried out and the amount of unmetabolized test compound is measured as AUC, compound concentration vs. time is plotted, and the $t_{1/2}$ value of the test compound is extrapolated.

Preferred compounds provided herein exhibit in vitro $t_{1/2}$ values of greater than 10 minutes and less than 4 hours, preferably between 30 minutes and 1 hour, in human liver microsomes.

Example 8

MDCK Toxicity Assay

This Example illustrates the evaluation of compound toxicity using a Madin Darby canine kidney (MDCK) cell cytotoxicity assay.

1 μL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of $0.1 \times 10^6$ cells/ml with warm (37° C.) medium (VITACELL Minimum Essential Medium Eagle, ATCC catalog # 30-2003). 100 μL of diluted cells is added to each well, except for five standard curve control wells that contain 100 μL of warm medium without cells. The plate is then incubated at 37° C. under 95% $O_2$, 5% $CO_2$ for 2 hours with constant shaking. After incubation, 50 μL of mammalian cell lysis solution (from the PACKARD (Meriden, Conn.) ATP-LITE-M Luminescent ATP detection kit) is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The ATP-LITE-M Luminescent ATP detection kit is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 μL of serially diluted PACKARD standard is added to each of the standard curve control wells to yield a final concentration in each subsequent well of 200 nM, 100 nM, 50 nM, 25 nM and 12.5 nM. PACKARD substrate solution (50 μL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOP-COUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 μM of a preferred test compound exhibit ATP levels that are at least 80%, preferably at least 90%, of the untreated cells. When a 100 μM concentration of the test compound is used, cells treated with preferred test compounds exhibit ATP levels that are at least 50%, preferably at least 80%, of the ATP levels detected in untreated cells.

Example 9

Dorsal Root Ganglion Cell Assay

This Example illustrates a representative dorsal root ganglian cell assay for evaluating VR1 antagonist or agonist activity of a compound.

DRG are dissected from neonatal rats, dissociated and cultured using standard methods (Aguayo and White (1992) *Brain Research* 570:61-67). After 48 hour incubation, cells are washed once and incubated for 30-60 minutes with the calcium sensitive dye Fluo 4 AM (2.5-10 μg/ml; TefLabs, Austin, Tex.). Cells are then washed once. Addition of capsaicin to the cells results in a VR1-dependent increase in intracellular calcium levels which is monitored by a change in Fluo-4 fluorescence with a fluorometer. Data are collected for 60-180 seconds to determine the maximum fluorescent signal.

For antagonist assays, various concentrations of compound are added to the cells. Fluorescent signal is then plotted as a function of compound concentration to identify the concentration required to achieve a 50% inhibition of the capsaicin-activated response, or $IC_{50}$. Antagonists of the capsaicin receptor preferably have an $IC_{50}$ below 1 micromolar, 100 nanomolar, 10 nanomolar or 1 nanomolar.

For agonist assays, various concentrations of compound are added to the cells without the addition of capsaicin. Compounds that are capsaicin receptor agonists result in a VR1-dependent increase in intracellular calcium levels which is monitored by a change in Fluo-4 fluorescence with a fluorometer. The $EC_{50}$, or concentration required to achieve 50% of the maximum signal for a capsaicin-activated response, is preferably below 1 micromolar, below 100 nanomolar or below 10 nanomolar.

Example 10

Animal Models for Determining Pain Relief

This Example illustrates representative methods for assessing the degree of pain relief provided by a compound.

A. Pain Relief Testing

The following methods may be used to assess pain relief.

Mechanical Allodynia

Mechanical allodynia (an abnormal response to an innocuous stimulus) is assessed essentially as described by Chaplan et al. (1994) *J. Neurosci. Methods* 53:55-63 and Tal and Eliav (1998) *Pain* 64(3):511-518. A series of von Frey filaments of varying rigidity (typically 8-14 filaments in a series) are applied to the plantar surface of the hind paw with just enough force to bend the filament. The filaments are held in this position for no more than three seconds or until a positive allodynic response is displayed by the rat. A positive allodynic response consists of lifting the affected paw followed immediately by licking or shaking of the paw. The order and frequency with which the individual filaments are applied are determined by using Dixon up-down method. Testing is initiated with the middle hair of the series with subsequent filaments being applied in consecutive fashion, ascending or descending, depending on whether a negative or positive response, respectively, is obtained with the initial filament.

Compounds are effective in reversing or preventing mechanical allodynia-like symptoms if rats treated with such compounds require stimulation with a Von Frey filament of higher rigidity strength to provoke a positive allodynic response as compared to control untreated or vehicle treated rats. Alternatively, or in addition, testing of an animal in chronic pain may be done before and after compound administration. In such an assay, an effective compound results in an increase in the rigidity of the filament needed to induce a response after treatment, as compared to the filament that induces a response before treatment or in an animal that is also in chronic pain but is left untreated or is treated with vehicle. Test compounds are administered before or after onset of pain. When a test compound is administered after pain onset, testing is performed 10 minutes to three hours after administration.

Mechanical Hyperalgesia

Mechanical hyperalgesia (an exaggerated response to painful stimulus) is tested essentially as described by Koch et al. (1996) *Analgesia* 2(3):157-164. Rats are placed in individual compartments of a cage with a warmed, perforated metal floor. Hind paw withdrawal duration (i.e., the amount of time for which the animal holds its paw up before placing it back on the floor) is measured after a mild pinprick to the plantar surface of either hind paw.

Compounds produce a reduction in mechanical hyperalgesia if there is a statistically significant decrease in the duration of hindpaw withdrawal. Test compound may be administered before or after onset of pain. For compounds administered after pain onset, testing is performed 10 minutes to three hours after administration.

Thermal Hyperalgesia

Thermal hyperalgesia (an exaggerated response to noxious thermal stimulus) is measured essentially as described by Hargreaves et al. (1988) *Pain.* 32(1):77-88. Briefly, a constant radiant heat source is applied the animals' plantar surface of either hind paw. The time to withdrawal (i.e., the amount of time that heat is applied before the animal moves its paw), otherwise described as thermal threshold or latency, determines the animal's hind paw sensitivity to heat.

Compounds produce a reduction in thermal hyperalgesia if there is a statistically significant increase in the time to hindpaw withdrawal (i.e., the thermal threshold to response or latency is increased). Test compound may be administered before or after onset of pain. For compounds administered after pain onset, testing is performed 10 minutes to three hours after administration.

B. Pain Models

Pain may be induced using any of the following methods, to allow testing of analgesic efficacy of a compound. In general, compounds provided herein result in a statistically significant reduction in pain as determined by at least one of the previously described testing methods, using male SD rats and at least one of the following models.

Acute Inflammatory Pain Model

Acute inflammatory pain is induced using the carrageenan model essentially as described by Field et al. (1997) *Br. J. Pharmacol.* 121(8):1513-1522. 100-200 µl of 1-2% carrageenan solution is injected into the rats' hind paw. Three to four hours following injection, the animals' sensitivity to thermal and mechanical stimuli is tested using the methods described above. A test compound (0.01 to 50 mg/kg) is administered to the animal, prior to testing, or prior to injection of carrageenan. The compound can be administered orally or through any parenteral route, or topically on the paw. Compounds that relieve pain in this model result in a statistically significant reduction in mechanical allodynia and/or thermal hyperalgesia.

Chronic Inflammatory Pain Model

Chronic inflammatory pain is induced using one of the following protocols:

1. Essentially as described by Bertorelli et al. (1999) *Br. J. Pharmacol.* 128(6):1252-1258, and Stein et al. (1998) *Pharmacol. Biochem. Behav.* 31(2):455-51, 200 µl Complete Freund's Adjuvant (0.1 mg heat killed and dried *M. Tuberculosis*) is injected to the rats' hind paw: 100 µl into the dorsal surface and 100 µl into the plantar surface.
2. Essentially as described by Abbadie et al. (1994) *J Neurosci.* 14(10):5865-5871 rats are injected with 150 µl of CFA (1.5 mg) in the tibio-tarsal joint.

Prior to injection with CFA in either protocol, an individual baseline sensitivity to mechanical and thermal stimulation of the animals' hind paws is obtained for each experimental animal.

Following injection of CFA, rats are tested for thermal hyperalgesia, mechanical allodynia and mechanical hyperalgesia as described above. To verify the development of symptoms, rats are tested on days 5, 6, and 7 following CFA injection. On day 7, animals are treated with a test compound, morphine or vehicle. An oral dose of morphine of 1-5 mg/kg is suitable as positive control. Typically, a dose of 0.01-50 mg/kg of test compound is used. Compounds can be administered as a single bolus prior to testing or once or twice or three times daily, for several days prior to testing. Drugs are administered orally or through any parenteral route, or applied topically to the animal.

Results are expressed as Percent Maximum Potential Efficacy (MPE). 0% MPE is defined as analgesic effect of vehicle, 100% MPE is defined as an animal's return to pre-CFA baseline sensitivity. Compounds that relieve pain in this model result in a MPE of at least 30%.

Chronic Neuropathic Pain Model

Chronic neuropathic pain is induced using the chronic constriction injury (CCI) to the rat's sciatic nerve essentially as described by Bennett and Xie (1988) *Pain* 33:87-107. Rats are anesthetized (e.g. with an intraperitoneal dose of 50-65 mg/kg pentobarbital with additional doses administered as needed). The lateral aspect of each hind limb is shaved and disinfected. Using aseptic technique, an incision is made on the lateral aspect of the hind limb at the mid thigh level. The biceps femoris is bluntly dissected and the sciatic nerve is exposed. On one hind limb of each animal, four loosely tied ligatures are made around the sciatic nerve approximately 1-2 mm apart. On the other side the sciatic nerve is not ligated and is not manipulated. The muscle is closed with continuous pattern and the skin is closed with wound clips or sutures. Rats are assessed for mechanical allodynia, mechanical hyperalgesia and thermal hyperalgesia as described above.

Compounds that relieve pain in this model result in a statistically significant reduction in mechanical allodynia, mechanical hyperalgesia and/or thermal hyperalgesia when administered (0.01-50 mg/kg, orally, parenterally or topically) immediately prior to testing as a single bolus, or for several days: once or twice or three times daily prior to testing.

What is claimed is:

1. A compound or a pharmaceutically acceptable salt thereof, wherein the compound is selected from:
   (4-Cyclopropyl-phenyl)-[2-methoxymethyl-7-(3-trifluoromethyl-pyridin-2-yl)-quinazolin-4-yl]-amine;
   (4-Isopropyl-phenyl)-[2-(tetrahydro-pyran-4-yloxymethyl)-7-(3-trifluoromethyl-pyridin-2-yl)-quinazolin-4-yl]-amine;
   (4-Isopropyl-phenyl)-[2-methoxymethyl-7-(3-methyl-pyridin-2-yl)-quinazolin-4yl]-amine;
   (4-Isopropyl-phenyl)-[2-methoxymethyl-7-(3-trifluoromethyl-pyridin-2-yl)-quinazolin-4-yl]-amine;
   (4-tert-Butyl-phenyl)-[2-methoxymethyl-7-(3-trifluoromethyl-pyridin-2-yl)-quinazolin-4-yl]-amine;
   (4-Isopropyl-phenyl)-[7-(3-methyl-pyridin-2-yl)-2-(tetrahydro-pyran-4-yloxymethyl)-quinazolin-4-yl]-amine;
   (4-tert-Butyl-phenyl)-[7-(3-chloro-pyridin-2-yl)-2-ethoxymethyl-quinazolin-4-yl]-amine;
   (4-tert-Butyl-phenyl)-[7-(3-chloro-pyridin-2-yl)-2-methoxymethyl-quinazolin-4-yl]-amine;
   [2-(Tetrahydro-pyran-4-yloxymethyl)-7-(3-trifluoromethyl-pyridin-2-yl)-quinazolin-4-yl]-(4-trifluoromethyl-phenyl)-amine;
   [2-Benzyloxymethyl-7-(3-trifluoromethyl-pyridin-2-yl)-quinazolin-4-yl]-[4-(2,2,2-trifluoro-1-methyl-ethyl)-phenyl]-amine;
   [2-Benzyloxymethyl-7-(3-trifluoromethyl-pyridin-2-yl)-quinazolin-4-yl]-(4-trifluoromethyl-phenyl)-amine;
   [2-Benzyloxymethyl-7-(3-trifluoromethyl-pyridin-2-yl)-quinazolin-4-yl]-[4-(2-methoxy-1,1-dimethyl-ethyl)-phenyl]-amine;
   [2-Benzyloxymethyl-7-(3-trifluoromethyl-pyridin-2-yl)-quinazolin-4-yl]-(4-tert-butyl-phenyl)-amine;
   [2-Ethoxymethyl-7-(3-methyl-pyridin-2-yl)-quinazolin-4-yl]-(4-isopropyl-phenyl)-amine;
   [2-Ethoxymethyl-7-(3-methyl-pyridin-2-yl)-quinazolin-4-yl]-(4-trifluoromethyl-phenyl)-amine;
   [2-Ethoxymethyl-7-(3-trifluoromethyl-pyridin-2-yl)-quinazolin-4-yl]-(4-trifluoromethyl-phenyl)-amine;
   [2-Isopropoxymethyl-7-(3-methyl-pyridin-2-yl)-quinazolin-4-yl]-(4-trifluoromethyl-phenyl)-amine;
   [2-Isopropoxymethyl-7-(3-methyl-pyridin-2-yl)-quinazolin-4-yl]-(4-isopropyl-phenyl)-amine;
   [2-Isopropoxymethyl-7-(3-trifluoromethyl-pyridin-2-yl)-quinazolin-4-yl]-(4-trifluoromethyl-phenyl)-amine;
   [2-Methoxymethyl-7-(3-methylpyridin-2-yl)-quinazolin-4-yl]-(4-trifluoromethylphenyl)-amine;
   [2-Methoxyethyl-7-(3-trifluoromethyl-pyridin-2-yl)-quinazolin-4-yl]-(4-trifluoromethyl-phenyl)-amine;
   [4-(2-Methoxy-1,1-dimethyl-ethyl)-phenyl]-[2-methoxymethyl-7-(3-trifluoromethyl-pyridin-2-yl)-quinazolin-4-yl]-amine;
   [4-(4-Isopropyl-phenylamino)-7-(3-trifluoromethyl-pyridin-2-yl)-quinazolin-2-yl]-methanol;
   [4-(4-tert-Butyl-phenylamino)-7-(3-chloro-pyridin-2-yl)-quinazolin-2-yl]-methanol;
   [4-(4-tert-Butyl-phenylamino)-7-(3-trifluoromethyl-pyridin-2-yl)-quinazolin-2-yl]-methanol;
   [4-(4-Trifluoromethyl-phenylamino)-7-(3-trifluoromethyl-pyridin-2-yl)-quinazolin-2-yl]-methanol;
   [7-(3-Chloro-pyridin-2-yl)-2-(tetrahydro-pyran-4-yloxymethyl)-quinazolin-4-yl]-(4-trifluoromethyl-phenyl)-amine;
   [7-(3-Chloro-pyridin-2-yl)-2-(tetrahydro-pyran-4-yloxymethyl)-quinazolin-4-yl]-(4-isopropyl-phenyl)-amine;
   [7-(3-Chloro-pyridin-2-yl)-2-ethoxymethyl-quinazolin-4-yl]-(4-isopropyl-phenyl)-amine;
   [7-(3-Chloro-pyridin-2-yl)-2-ethoxymethyl-quinazolin-4-yl]-(4-trifluoromethyl-phenyl)-amine;
   [7-(3-Chloro-pyridin-2-yl)-2-methoxymethyl-quinazolin-4-yl]-(4-isopropyl-phenyl)-amine;
   [7-(3-Chloro-pyridin-2-yl)-2-methoxymethyl-quinazolin-4-yl]-(4-trifluoromethyl-phenyl)-amine;
   [7-(3-Chloro-pyridin-2-yl)-4-(4-isopropyl-phenylamino)-quinazolin-2-yl]-methanol;
   [7-(3-Methyl-pyridin-2-yl)-2-(tetrahydro-pyran-4-yloxymethyl)-quinazolin-4-yl]-(4-trifluoromethyl-phenyl)-amine;
   2-{4-[2-Benzyloxymethyl-7-(3-trifluoromethyl-pyridin-2-yl)-quinazolin-4-ylamino]-phenyl}-2-methyl-propionitrile; and
   2-{4-[2-Methoxymethyl-7-(3-trifluoromethyl-pyridin-2-yl)-quinazolin-4-ylamino]-phenyl}-2-methyl-propionitrile.

2. A compound or pharmaceutically acceptable salt thereof according to claim 1, wherein the compound is (4-isopropyl-phenyl)-[2-(tetrahydro-pyran-4-yloxymethyl)-7-(3-trifluoromethyl-pyridin-2-yl)-quinazolin-4-yl]-amine.

3. A compound or pharmaceutically acceptable salt thereof according to claim 1, wherein the compound is [2-isopropoxymethyl-7-(3-trifluoromethyl-pyridin-2-yl)-quinazolin-4-yl]-(4-trifluoromethyl-phenyl)-amine.

4. A compound or pharmaceutically acceptable salt thereof according to claim 1, wherein the compound is [7-(3-chloro-pyridin-2-yl)-2-methoxymethyl-quinazolin-4-yl]-(4-isopropyl-phenyl)-amine.

5. A compound or pharmaceutically acceptable salt thereof according to claim 1, wherein the compound is 2-{4-[2-benzyloxymethyl-7-(3-trifluoromethyl-pyridin-2-yl)-quinazolin-4-ylamino]-phenyl}-2-methyl-propionitrile.

6. A compound or a pharmaceutically acceptable salt thereof, wherein the compound is selected from:
   (6-tert-Butyl-pyridin-3-yl)-[2-methoxymethyl-7-(3-trifluoromethyl-pyridin-2-yl)-quinazolin-4-yl]-amine;
   (6-tert-Butyl-pyridin-3-yl)-[7-(3-chloro-pyridin-2-yl)-2-ethoxymethyl-quinazolin-4-yl]-amine;

(6-tert-Butyl-pyridin-3-yl)-[7-(3-chloro-pyridin-2-yl)-2-methoxymethyl-quinazolin-4-yl]-amine;
[2-(Tetrahydro-pyran-4-yloxymethyl)-7-(3-trifluoromethyl-pyridin-2-yl)-quinazolin-4-yl]-(6-trifluoromethyl-pyridin-3-yl)-amine;
[2-Benzyloxymethyl-7-(3-trifluoromethyl-pyridin-2-yl)-quinazolin-4-yl]-(6-trifluoromethyl-pyridin-3-yl)-amine;
[2-Benzyloxymethyl-7-(3-trifluoromethyl-pyridin-2-yl)-quinazolin-4-yl]-(5-trifluoromethyl-pyridin-2-yl)-amine;
[2-Ethoxymethyl-7-(3-trifluoromethyl-pyridin-2-yl)-quinazolin-4-yl]-(6-trifluoromethyl-pyridin-3-yl)-amine;
[2-Isopropoxymethyl-7-(3-trifluoromethyl-pyridin-2-yl)-quinazolin-4-yl]-(6-trifluoromethyl-pyridin-3-yl)-amine;
[2-Methoxymethyl-7-(3-trifluoromethyl-pyridin-2-yl)-quinazolin-4-yl]-(5-trifluoromethyl-pyridin-2-yl)-amine; and
[2-Methoxymethyl-7-(3-trifluoromethyl-pyridin-2-yl)-quinazolin-4-yl]-(6-trifluoromethyl-pyridin-3-yl)-amine.

7. A compound or pharmaceutically acceptable salt thereof according to claim 6, wherein the compound is (6-tert-butyl-pyridin-3-yl)-[7-(3-chloro-pyridin-2-yl)-2-ethoxymethyl-quinazolin-4-yl]-amine.

8. A compound or pharmaceutically acceptable salt thereof according to claim 6, wherein the compound is [2-benzyloxymethyl-7-(3-trifluoromethyl-pyridin-2-yl)-quinazolin-4-yl]-(5-trifluoromethyl-pyridin-2-yl)-amine.

9. A compound or pharmaceutically acceptable salt thereof according to claim 6, wherein the compound is [2-ethoxymethyl-7-(3-trifluoromethyl-pyridin-2-yl)-quinazolin-4-yl]-(6-trifluoromethyl-pyridin-3-yl)-amine.

10. A compound or pharmaceutically acceptable salt thereof according to claim 6, wherein the compound is [2-methoxymethyl-7-(3-trifluoromethyl-pyridin-2-yl)-quinazolin-4-yl]-(6-trifluoromethyl-pyridin-3-yl)-amine.

11. A compound or a pharmaceutically acceptable salt thereof, wherein the compound is selected from:
(4-Chloro-phenyl)-[2-isobutoxymethyl-7-(3-trifluoromethyl-pyridin-2-yl)-pyrido[2,3-d]pyrimidin-4-yl]-amine;
(4-Chloro-phenyl)-[2-methoxymethyl-7-(3-trifluoromethyl-pyridin-2-yl)-pyrido[2,3-d]pyrimidin-4-yl]-amine;
(4-Chloro-phenyl)-[7-(3-chloro-pyridin-2-yl)-2-isobutoxymethyl-pyrido[2,3-d]pyrimidin-4-yl]-amine;
(4-Difluoromethyl-phenyl)-[2-ethoxymethyl-7-(3-trifluoromethyl-pyridin-2-yl)-pyrido[2,3-d]pyrimidin-4-yl]-amine;
(4-Difluoromethyl-phenyl)-[2-isobutoxymethyl-7-(3-trifluoromethyl-pyridin-2-yl)-pyrido[2,3-d]pyrimidin-4-yl]-amine;
(4-Difluoromethyl-phenyl)-[2-methoxymethyl-7-(3-trifluoromethyl-pyridin-2-yl)-pyrido[2,3-d]pyrimidin-4-yl]-amine;
(4-Fluoro-phenyl)-[2-isobutoxymethyl-7-(3-trifluoromethyl-pyridin-2-yl)-pyrido[2,3-d]pyrimidin-4-yl]-amine;
(4-Isopropyl-phenyl)-[2-methoxymethyl-7-(3-methyl-pyridin-2-yl)-pyrido[2,3-d]pyrimidin-4-yl]-amine;
(4-Isopropyl-phenyl)-[2-methoxymethyl-7-(3-trifluoromethyl-pyridin-2-yl)-pyrido[2,3-d]pyrimidin-4-yl]-amine;
(4-sec-Butyl-phenyl)-[2-methoxymethyl-7-(3-methyl-pyridin-2-yl)-pyrido[2,3-d]pyrimidin-4-yl]-amine;
(4-sec-Butyl-phenyl)-[2-methoxymethyl-7-(3-trifluoromethyl-pyridin-2-yl)-pyrido[2,3-d]pyrimidin-4-yl]-amine;
(4-sec-Butyl-phenyl)-[7-(3-chloro-pyridin-2-yl)-2-(2-methoxy-ethoxymethyl)-pyrido[2,3-d]pyrimidin-4-yl]-amine;
(4-sec-Butyl-phenyl)-[7-(3-chloro-pyridin-2-yl)-2-methoxymethyl-pyrido[2,3-d]pyrimidin-4-yl]-amine;
(4-tert-Butyl-phenyl)-[2-isobutoxymethyl-7-(3-methyl-pyridin-2-yl)-pyrido[2,3-d]pyrimidin-4-yl]-amine;
(4-tert-Butyl-phenyl)-[2-isobutoxymethyl-7-(3-trifluoromethyl-pyridin-2-yl)-pyrido[2,3-d]pyrimidin-4-yl]-amine;
(4-tert-Butyl-phenyl)-[2-methoxymethyl-7-(3-methyl-pyridin-2-yl)-pyrido[2,3-d]pyrimidin-4-yl]-amine;
(4-tert-Butyl-phenyl)-[2-methoxymethyl-7-(3-trifluoromethyl-pyridin-2-yl)-pyrido[2,3-d]pyrimidin-4-yl]-amine;
(4-tert-Butyl-phenyl)-[7-(3-chloro-pyridin-2-yl)-2-(2-methoxy-ethoxymethyl)-pyrido[2,3-d]pyrimidin-4-yl]-amine;
(4-tert-Butyl-phenyl)-[7-(3-chloro-pyridin-2-yl)-2-ethoxymethyl-pyrido[2,3-d]pyrimidin-4-yl]-amine;
(4-tert-Butyl-phenyl)-[7-(3-chloro-pyridin-2-yl)-2-methoxymethyl-pyrido[2,3-d]pyrimidin-4-yl]-amine;
[2-Ethoxymethyl-7-(3-methyl-pyridin-2-yl)-pyrido[2,3-d]pyrimidin-4-yl]-(4-trifluoromethyl-phenyl)-amine;
[2-Ethoxymethyl-7-(3-methyl-pyridin-2-yl)-pyrido[2,3-d]pyrimidin-4-yl]-(4-isopropyl-phenyl)-amine;
[2-Ethoxymethyl-7-(3-trifluoromethyl-pyridin-2-yl)-pyrido[2,3-d]pyrimidin-4-yl]-(4-trifluoromethyl-phenyl)-amine;
[2-Ethoxymethyl-7-(3-trifluoromethyl-pyridin-2-yl)-pyrido[2,3-d]pyrimidin-4-yl]-[4-(2,2,2-trifluoro-1-methyl-ethyl)-phenyl]-amine;
[2-Isobutoxymethyl-7-(3-methyl-pyridin-2-yl)-pyrido[2,3-d]pyrimidin-4-yl]-(4-isopropyl-phenyl)-amine;
[2-Isobutoxymethyl-7-(3-methyl-pyridin-2-yl)-pyrido[2,3-d]pyrimidin-4-yl]-(4-trifluoromethyl-phenyl)-amine;
[2-Isobutoxymethyl-7-(3-methyl-pyridin-2-yl)-pyrido[2,3-d]pyrimidin-4-yl]-[4-(2-methoxy-1,1-dimethyl-ethyl)-phenyl]-amine;
[2-Isobutoxymethyl-7-(3-trifluoromethyl-pyridin-2-yl)-pyrido[2,3-d]pyrimidin-4-yl]-(4-isopropyl-phenyl)-amine;
[2-Isobutoxymethyl-7-(3-trifluoromethyl-pyridin-2-yl)-pyrido[2,3-d]pyrimidin-4-yl]-(4-trifluoromethyl-phenyl)-amine;
[2-Isobutoxymethyl-7-(3-trifluoromethyl-pyridin-2-yl)-pyrido[2,3-d]pyrimidin-4-yl]-[4-(2,2,2-trifluoro-1-methyl-ethyl)-phenyl]-amine;
[2-Methoxymethyl-7-(3-methyl-pyridin-2-yl)-pyrido[2,3-d]pyrimidin-4-yl]-(4-trifluoromethyl-phenyl)-amine;
[2-Methoxymethyl-7-(3-trifluoromethyl-pyridin-2-yl)-pyrido[2,3-d]pyrimidin-4-yl]-[4-(2,2,-trifluoro-1-methyl-ethyl)-phenyl]-amine;
[2-Methoxymethyl-7-(3-trifluoromethyl-pyridin-2-yl)-pyrido[2,3-d]pyrimidin-4-yl]-(4-trifluoromethyl-phenyl)-amine;
[4-(4-tert-Butyl-phenylamino)-7-(3-methyl-pyridin-2-yl)-pyrido[2,3-d]pyrimidin-2-yl]-methanol;
[4-(4-Trifluoromethyl-phenylamino)-7-(3-trifluoromethyl-pyridin-2-yl)-pyrido[2,3-d]pyrimidin-2-yl]-methanol;

[7-(3-Chloro-pyridin-2-yl)-2-(1-methoxy-ethyl)-pyrido[2,3-d]pyrimidin4-yl]-(4-trifluoromethyl-phenyl)-amine;
[7-(3-Chloro-pyridin-2-yl)-2-(2-methoxy-ethoxymethyl)-pyrido[2,3-d]pyrimidin-4-yl]-(4-trifluoromethyl-phenyl)-amine;
[7-(3-Chloro-pyridin-2-yl)-2-(2-methoxy-ethoxymethyl)-pyrido[2,3-d]pyrimidin-4-yl]-(4-isopropyl-phenyl)-amine;
[7-(3-Chloro-pyridin-2-yl)-2-ethoxymethyl-pyrido[2,3-d]pyrimidin-4-yl]-(4-isopropyl-phenyl)amine;
[7-(3-Chloro-pyridin-2-yl)-2-ethoxymethyl-pyrido[2,3-d]pyrimidin-4-yl]-(4-trifluoromethyl-phenyl)-amine;
[7-(3-Chloro-pyridin-2-yl)-2-ethoxymethyl-pyrido[2,3-d]pyrimidin-4-yl]-[4-(2,2,2-trifluoro-1-methyl-ethyl)-phenyl]-amine;
[7-(3-Chloro-pyridin-2-yl)-2-ethoxymethyl-pyrido[2,3-d]pyrimidin-4-yl]-(4-difluoromethyl-phenyl)-amine;
[7-(3-Chloro-pyridin-2-yl)-2-isobutoxymethyl-pyrido[2,3-d]pyrimidin-4-yl]-(4-trifluoromethyl-phenyl)-amine;
[7-(3-Chloro-pyridin-2-yl)-2-isobutoxymethyl-pyrido[2,3-d]pyrimidin-4-yl]-[4-(2,2,2-trifluoro-1-methyl-ethyl)-phenyl]-amine;
[7-(3-Chloro-pyridin-2-yl)-2-isobutoxymethyl-pyrido[2,3-d]pyrimidin-4-yl]-(4-fluoro-phenyl)-amine;
[7-(3-Chloro-pyridin-2-yl)-2-isobutoxymethyl-pyrido[2,3-d]pyrimidin-4-yl]-(4-ethyl-phenyl)-amine;
[7-(3-Chloro-pyridin-2-yl)-2-isobutoxymethyl-pyrido[2,3-d]pyrimidin-4-yl]-(4-propyl-phenyl)-amine;
[7-(3-Chloro-pyridin-2-yl)-2-isobutoxymethyl-pyrido[2,3-d]pyrimidin-4-yl]-(4-ethynyl-phenyl)-amine;
[7-(3-Chloro-pyridin-2-yl)-2-methoxymethyl-pyrido[2,3-d]pyrimidin-4-yl]-(4-isopropyl-phenyl)-amine;
[7-(3-Chloro-pyridin-2-yl)-2-methoxymethyl-pyrido[2,3-d]pyrimidin-4-yl]-[4-(2-methoxy-1,1-dimethyl-ethyl)-phenyl]-amine;
[7-(3-Chloro-pyridin-2-yl)-2-methoxymethyl-pyrido[2,3-d]pyrimidin-4-yl]-(4-difluoromethyl-phenyl)-amine;
[7-(3-Chloro-pyridin-2-yl)-2-methoxymethyl-pyrido[2,3-d]pyrimidin-4-yl]-(4-trifluoromethyl-phenyl)-amine;
[7-(3-Methyl-pyridin-2-yl)-4-(4-trifluoromethyl-phenylamino)-pyrido[2,3-d]pyridin-2-yl]-methanol;
1-{4-[2-Isobutoxymethyl-7-(3-methyl-pyridin-2-yl)-pyrido[2,3-d]pyrimidin-4-ylamino]-phenyl}-cyclobutanecarbonitrile;
1-{4-[2-Methoxymethyl-7-(3-methyl-pyridin-2-yl)-pyrido[2,3-d]pyrimidin-4-ylamino]-phenyl}-cyclobutanecarbonitrile;
1-{4-[7-(3-Chloro-pyridin-2-yl)-2-ethoxymethyl-pyrido[2,3-d]pyrimidin-4-ylamino]-phenyl}-cyclobutanecarbonitrile;
2-{4-[2-Ethoxymethyl-7-(3-trifluoromethyl-pyridin-2-yl)-pyrido[2,3-d]pyrimidin-4-ylamino]-phenyl}-2-methyl-propionitrile;
2-{4-[2-Isobutoxymethyl-7-(3-methyl-pyridin-2-yl)-pyrido[2,3-d]pyrimidin-4-ylamino]-phenyl}-2-methyl-propionitrile;
2-{4-[2-Isobutoxymethyl-7-(3-trifluoromethyl-pyridin-2-yl)-pyrido[2,3-d]pyrimidin-4-ylamino]-phenyl}-2-methyl-propionitrile;
2-{4-[2-Methoxymethyl-7-(3-methyl-pyridin-2-yl)-pyrido[2,3-d]pyrimidin-4-ylamino]-phenyl}-2-methyl-propionitrile;
2-{4-[2-Methoxymethyl-7-(3-trifluoromethyl-pyridin-2-yl)-pyrido[2,3-d]pyrimidin-4-ylamino]-phenyl}-2-methyl-propionitrile;
2-{4-[7-(3-Chloro-pyridin-2-yl)-2-(2-methoxy-ethoxymethyl)-pyrido[2,3-d]pyrimidin-4-ylamino]-phenyl}-2-methyl-propionitrile;
2-{4-[7-(3-Chloro-pyridin-2-yl)-2-isobutoxymethyl-pyrido[2,3-d]pyrimidin-4-ylamino]-phenyl}-2-methyl-propionitrile;
2-{4-[7-(3-Chloro-pyridin-2-yl)-2-methoxymethyl-pyrido[2,3-d]pyrimidin-4-ylamino]-phenyl}-2-methyl-propionitrile;
3-{4-[2-Isobutoxymethyl-7-(3-methyl-pyridin-2-yl)-pyrido[2,3-d]pyrimidin-4-ylamino]-phenyl}-3-methyl-butan-2-one;
3-{4-[2-Isobutoxymethyl-7-(3-trifluoromethyl-pyridin-2-yl)-pyrido[2,3-d]pyrimidin-4-ylamino]-phenyl}-3-methyl-butan-2-one;
3-{4-[2-Methoxymethyl-7-(3-methyl-pyridin-2-yl)-pyrido[2,3-d]pyrimidin-4-ylamino]-phenyl}-3-methyl-butan-2-one;
3-{4-[2-Methoxymethyl-7-(3-trifluoromethyl-pyridin-2-yl)-pyrido[2,3-d]pyrimidin-4-ylamino]-phenyl}-3-methyl-butan-2-one;
3-{4-[7-(3-Chloro-pyridin-2-yl)-2-isobutoxymethyl-pyrido[2,3-d]pyrimidin-4-ylamino]-phenyl}-3-methyl-butan-2-one;
3-{4-[7-(3-Chloro-pyridin-2-yl)-2-methoxymethyl-pyrido[2,3-d]pyrimidin-4-ylamino]-phenyl}-3-methyl-butan-2-one;
4-[2-Isobutoxymethyl-7-(3-trifluoromethyl-pyridin-2-yl)-pyrido[2,3-d]pyrimidin-4-ylamino]-benzonitrile;
4-[2-Methoxymethyl-7-(3-trifluoromethyl-pyridin-2-yl)-pyrido[2,3-d]pyrimidin-4-ylamino]-benzonitrile; and
4-[7-(3-Chloro-pyridin-2-yl)-2-isobutoxymethyl-pyrido[2,3-d]pyrimidin-4-ylamino]-benzonitrile.

12. A compound or pharmaceutically acceptable salt thereof according to claim 11, wherein the compound is (4-chloro-phenyl)-[2-isobutoxymethyl-7-(3-trifluoromethyl-pyridin-2-yl)-pyrido[2,3-d]pyrimidin-4-yl]-amine.

13. A compound or pharmaceutically acceptable salt thereof according to claim 11, wherein the compound is (4-tert-butyl-phenyl)-[2-isobutoxymethyl-7-(3-methyl-pyridin-2-yl)-pyrido[2,3-d]pyrimidin-4-yl]-amine.

14. A compound or pharmaceutically acceptable salt thereof according to claim 11, wherein the compound is [2-isobutoxymethyl-7-(3-methyl-pyridin-2-yl)-pyrido[2,3-d]pyrimidin-4-yl]-[4-(2-methoxy-1,1-dimethyl-ethyl)-phenyl]-amine.

15. A compound or pharmaceutically acceptable salt thereof according to claim 11, wherein the compound is 4-[2-isobutoxymethyl-7-(3-trifluoromethyl-pyridin-2-yl)-pyrido[2,3-d]pyrimidin-4-ylamino]-benzonitrile.

16. A compound or a pharmaceutically acceptable salt thereof, wherein the compound is selected from:
(6-tert-Butyl-pyridin-3-yl)-[2-isobutoxymethyl-7-(3-methyl-pyridin-2-yl)-pyrido[2,3-d]pyrimidin-4-yl]-amine;
(6-tert-Butyl-pyridin-3-yl)-[2-isobutoxymethyl-7-(3-trifluoromethyl-pyridin-2-yl)-pyrido[2,3-d]pyrimidin-4-yl]-amine;
(6-tert-Butyl-pyridin-3-yl)-[2-methoxymethyl-7-(3-methyl-pyridin-2-yl)-pyrido[2,3-d]pyrimidin-4-yl]-amine;
(6-tert-Butyl-pyridin-3-yl)-[2-methoxymethyl-7-(3-trifluoromethyl-pyridin-2-yl)-pyrido[2,3-d]pyrimidin-4-yl]-amine;
(6-tert-Butyl-pyridin-3-yl)-[7-(3-chloro-pyridin-2-yl)-2-isobutoxymethyl-pyrido[2,3-d]pyrimidin-4-yl]-amine;

(6-tert-Butyl-pyridin-3-yl)-[7-(3-chloro-pyridin-2-yl)-2-methoxymethyl-pyrido[2,3-d]pyrimidin-4-yl]-amine;

[2-Ethoxymethyl-7-(3-trifluoromethyl-pyridin-2-yl)-pyrido[2,3-d]pyrimidin-4-yl]-(6-trifluoromethyl-pyridin-3-yl)-amine;

[2-Isobutoxymethyl-7-(3-trifluoromethyl-pyridin-2-yl)-pyrido[2,3-d]pyrimidin-4-yl]-(5-trifluoromethyl-pyridin-2-yl)-amine;

[2-Isobutoxymethyl-7-(3-trifluoromethyl-pyridin-2-yl)-pyrido[2,3-d]pyrimidin-4-yl]-(6-trifluoromethyl-pyridin-3-yl)-amine;

[2-Methoxymethyl-7-(3-trifluoromethyl-pyridin-2-yl)-pyrido[2,3-d]pyrimidin-4-yl]-(5-trifluoromethyl-pyridin-2-yl)-amine;

[2-Methoxymethyl-7-(3-methyl-pyridin-2-yl)-pyrido[2,3-d]pyrimidin-4-yl]-(6-trifluoromethyl-pyridin-3-yl)-amine;

[2-Methoxymethyl-7-(3-trifluoromethyl-pyridin-2-yl)-pyrido[2,3-d]pyrimidin-4-yl]-(6-trifluoromethyl-pyridin-3-yl)-amine;

[7-(3-Chloro-pyridin-2-yl)-2-ethoxymethyl-pyrido[2,3-d]pyrimidin-4-yl]-(6-trifluoromethyl-pyridin-3-yl)-amine; and

[7-(3-Chloro-pyridin-2-yl)-2-isobutoxymethyl-pyrido[2,3-d]pyrimidin-4-yl]-(6-trifluoromethyl-pyridin-3-yl)-amine.

17. A compound or pharmaceutically acceptable salt thereof according to claim 16, wherein the compound is (6-tert-Butyl-pyridin-3-yl)-[2-isobutoxymethyl-7-(3-methyl-pyridin-2-yl)-pyrido[2,3-d]pyrimidin-4-yl]-amine.

18. A compound or pharmaceutically acceptable salt thereof according to claim 16, wherein the compound is (6-tert-butyl-pyridin-3-yl)-[7-(3-chloro-pyridin-2-yl)-2-methoxymethyl-pyrido[2,3-d]pyrimidin-4-yl]-amine.

19. A compound or pharmaceutically acceptable salt thereof according to claim 16, wherein the compound is [2-methoxymethyl-7-(3-methyl-pyridin-2-yl)-pyrido[2,3-d]pyrimidin-4-yl]-(6-trifluoromethyl-pyridin-3-yl)-amine.

20. A compound or pharmaceutically acceptable salt thereof according to claim 16, wherein the compound is [2-methoxymethyl-7-(3-trifluoromethyl-pyridin-2-yl)-pyrido[2,3-d]pyrimidin-4-yl]-(5-trifluoromethyl-pyridin-2-yl)-amine.

21. A compound or pharmaceutically acceptable salt thereof according to claim 1, wherein the compound is (4-tert-Butyl-phenyl)[7-(3-chloro-pyridin-2yl)-2-ethoxymethyl-quinazolin-4-yl]-amine.

22. A compound or pharmaceutically acceptable salt thereof according to claim 1, wherein the compound is [2-Benzyloxymethyl-7-(3-trifluoromethyl-pyridin-2-yl)-quinazolin-4-yl]-[4-(2-methoxy-1, 1-dimethyl-ethyl)-phenyl]amine.

23. A compound or pharmaceutically acceptable salt thereof according to claim 1, wherein the compound is [2-Ethoxymethyl-7-(3-methyl-pyridin-2-yl)-quinazolin-4-yl[-(4-trifluoromethyl-phenyl)-amine.

24. A compound or pharmaceutically acceptable salt thereof according to claim 1, wherein the compound is [2-Methoxymethyl-7-(3-trifluoromethyl-pyridin-2-yl)-quinazolin-4-yl]-(4-trifluoromethyl-phenyl)-amine.

25. A compound or pharmaceutically acceptable salt thereof according to claim 1, wherein the compound is [4-(2-Methoxy-1, 1-dimethyl-ethyl)-phenyl]-[2-methoxymethyl-7-(3-trifluoromethyl-pyridin-2-yl)-quinazolin-4-yl]-amine.

26. A compound or pharmaceutically acceptable salt thereof according to claim 1, wherein the compound is [4-(4-tert-Butyl-phenylamino)-7-(3-trifluoromethyl-pyridin-2-yl)-quinazolin-2-yl]-methanol.

27. A compound or pharmaceutically acceptable salt thereof according to claim 1, wherein the compound is [7-(3-Chloro-pyridin-2-yl)-2-(1-methoxy-ethyl)-pyrido[2,3-d]pyrimidin-4-yl]-(4-trifluoromethyl-phenyl)-amine.

28. A compound or pharmaceutically acceptable salt thereof according to claim 1, wherein the compound is [7-(3-Chloro-pyridin-2-yl)-2-(tetrahydro-pyran-4-yloxymethyl)-quinazolin-4-yl]-(4-trifuoromethyl-phenyl)-amine.

29. A compound or pharmaceutically acceptable salt thereof according to claim 1, wherein the compound is 7-(3-Chloro-pyridin-2-yl)-2-ethoxymethyl-quinazolin-4-yl]-(4-trifluoromethyl-phenyl)-amine.

30. A compound or pharmaceutically acceptable salt thereof according to claim 11, wherein the compound is 2-1sobutoxymethyl-7-(3-trifluoromethyl-pyridin-2yl)-pyrido[2,3d]pyrimidin-4-yl]-(4-trifluoromethyl-phenyl)-amine.

31. A compound or pharmaceutically acceptable salt thereof according to claim 11, wherein the compound is [2-Methoxymethyl-7-(3-methyl-pyridin-2-yl)-pyrido[2,3-d]pyrimidin-4-yl]-(4-trifluoromethyl-phenyl)-amine.

32. A compound or pharmaceutically acceptable salt thereof according to claim 11, wherein the compound is [2-Methoxymethyl-7-(3-trifluoromethyl-pyridin-2-yl)-pyrido[2,3-d]pyrimidin-4-yl]-(4-trifluoromethyl-phenyl)-amine.

33. A compound or pharmaceutically acceptable salt thereof according to claim 11, wherein the compound is (4-Difluoromethyl-phenyl)-[2-methoxymethyl-7-(3-trifluoromethyl-pyridin-2-yl)-pyrido[2,3-d]pyrimidin-4-yl]-amine.

34. A compound or pharmaceutically acceptable salt thereof according to claim 11, wherein the compound is [7-(3-Chloro-pyridin-2-yl)-2-isobutoxymethyl-pyrido[2,3-d]pyrimidin-4-yl]-(4-fluoro-phenyl)-amine.

35. A compound or pharmaceutically acceptable salt thereof according to claim 11, wherein the compound is 1-{4-[2-Isobutoxymethyl-7-(3-methyl-pyridin-2-yl)-pyrido[2,3-d]pyrimidin-4-ylamino]-phenyl}-cyclobutanecarbonitrile.

36. A compound or pharmaceutically acceptable salt thereof according to claim 11, wherein the compound is 2-{4-[7-(3-Chloro-pyridin-2-yl)-2-isobutoxymethyl-pyrido[2,3-d]pyrimidin-4-ylamino]-phenyl}-2-methyl-propionitrile.

37. A compound or pharmaceutically acceptable salt thereof according to claim 11, wherein the compound is 3-{4-[2-Methoxymethyl-7-(3-trifluoromethyl-pyridin-2-yl)-pyrido[2,3-d]pyrimidin-4-ylamino]-phenyl}-3-methyl-butan-2-one.

38. A compound or pharmaceutically acceptable salt thereof according to claim 11, wherein the compound is 4-[2-Methoxymethyl-7-(3-trifluoromethyl-pyridin-2-yl)-pyrido[2,3-d]pyrimidin-4-ylamino]-benzonitrile.

39. A compound or pharmaceutically acceptable salt thereof according to claim 16, wherein the compound is [2-Isobutoxymethyl-7-(3-trifluoromethyl-pyridin-2-yl)-pyrido[2,3-d]pyrimidin-4-yl]-(5-trifluoromethyl-pyridin-2-yl)-amine.

* * * * *